US012115337B2

(12) United States Patent
Day et al.

(10) Patent No.: US 12,115,337 B2
(45) Date of Patent: Oct. 15, 2024

(54) INFUSION SYSTEM, DEVICE, AND METHOD HAVING ADVANCED INFUSION FEATURES

(71) Applicant: ICU Medical, Inc., San Clemente, CA (US)

(72) Inventors: William Kenneth Day, Hoffman Estates, IL (US); Justin Joseph Schmidt, Grayslake, IL (US); Steve Joseph Lindo, Chicago, IL (US); Paul John Foryt, Oakland, CA (US)

(73) Assignee: ICU Medical, Inc., San Clemente, CA (US)

( * ) Notice: Subject to any disclaimer, the term of this patent is extended or adjusted under 35 U.S.C. 154(b) by 426 days.

(21) Appl. No.: 17/106,875

(22) Filed: Nov. 30, 2020

(65) Prior Publication Data
US 2021/0146036 A1 May 20, 2021

Related U.S. Application Data

(62) Division of application No. 15/057,250, filed on Mar. 1, 2016, now Pat. No. 10,850,024.
(Continued)

(51) Int. Cl.
A61M 5/14 (2006.01)
A61M 5/168 (2006.01)
(Continued)

(52) U.S. Cl.
CPC ...... A61M 5/1407 (2013.01); A61M 5/16827 (2013.01); A61M 5/172 (2013.01);
(Continued)

(58) Field of Classification Search
CPC ............ A61M 5/1407; A61M 5/16827; A61M 205/3561; A61M 2205/3592; A61M 2205/52; G16H 20/17
See application file for complete search history.

(56) References Cited

U.S. PATENT DOCUMENTS 3,401,337 A 9/1968 Beusman et al.
3,484,681 A 12/1969 Grady, Jr. et al.
(Continued)

FOREIGN PATENT DOCUMENTS

AU 2013216679 9/2013
BR PI0704229-9 11/2009
(Continued)

OTHER PUBLICATIONS

Abbott Laboratories, "LifeCare® 5000, Plum®: Concurrent Flow Infusion System with DataPort™", System Operating Manual, Version 1.6, Jul. 1998, pp. 76.
(Continued)

Primary Examiner — James D Ponton
Assistant Examiner — Hong-Van N Trinh
(74) Attorney, Agent, or Firm — Knobbe Martens Olson & Bear LLP

(57) ABSTRACT

Aspects of the present disclosure provide systems, devices, and methods for delivering substances such as fluids, solutions, medications, and drugs to patients using infusion devices having a set of advanced features. These advanced features include aspects related to the programming of infusion devices, the configuration of infusion sequences performed by the infusion devices, and the interconnection of multiple infusion devices for interoperation during an infusion having a sequence of infusion steps.

12 Claims, 65 Drawing Sheets

Related U.S. Application Data

(60) Provisional application No. 62/127,076, filed on Mar. 2, 2015.

(51) Int. Cl.
*A61M 5/172* (2006.01)
*G16H 20/17* (2018.01)

(52) U.S. Cl.
CPC ..... *G16H 20/17* (2018.01); *A61M 2205/3561* (2013.01); *A61M 2205/3592* (2013.01); *A61M 2205/52* (2013.01)

(56) References Cited

U.S. PATENT DOCUMENTS

| | | |
|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,854,038 A | 12/1974 | McKinley |
| 3,886,459 A | 5/1975 | Hufford et al. |
| 3,890,554 A | 6/1975 | Yoshitake et al. |
| 3,894,431 A | 7/1975 | Muston et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,057,228 A | 11/1977 | Völker et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,515,584 A | 5/1985 | Abe et al. |
| 4,519,792 A | 5/1985 | Dawe |
| 4,521,212 A | 6/1985 | Ruschke |
| 4,525,163 A | 6/1985 | Slavik et al. |
| 4,526,568 A | 7/1985 | Clemens et al. |
| 4,526,574 A | 7/1985 | Pekkarinen |
| 4,529,401 A | 7/1985 | Leslie et al. |
| 4,533,350 A | 8/1985 | Danby et al. |
| 4,543,955 A | 10/1985 | Schroeppel |

(56) References Cited

U.S. PATENT DOCUMENTS

| | | |
|---|---|---|
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalute et al. |
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | Kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Blomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald et al. |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,769,001 A | 9/1988 | Prince |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,908,019 A | 3/1990 | Urquhart et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Pastrone et al. |
| 4,930,358 A | 6/1990 | Motegi et al. |
| 4,936,820 A | 6/1990 | Dennehey |
| 4,936,828 A | 6/1990 | Chiang |
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,014,798 A | 5/1991 | Glynn |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,040,699 A | 8/1991 | Gangemi |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |
| 5,064,412 A | 11/1991 | Henke et al. |
| 5,078,683 A | 1/1992 | Sancoff et al. |
| 5,084,663 A | 1/1992 | Olsson |

(56) References Cited

U.S. PATENT DOCUMENTS

| | | |
|---|---|---|
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,260,665 A | 11/1993 | Goldberg |
| 5,257,206 A | 12/1993 | Hanson |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,304,216 A | 4/1994 | Wallace |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,749 A | 6/1995 | Merte et al. |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |
| 5,537,853 A | 7/1996 | Finburgh et al. |
| 5,542,040 A | 7/1996 | Chang et al. |
| 5,545,140 A | 8/1996 | Conero et al. |

(56) References Cited

U.S. PATENT DOCUMENTS

| | | |
|---|---|---|
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,685,866 A | 11/1997 | Lopez |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,734,464 A | 3/1998 | Gibbs |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,066 A | 8/1999 | Harris |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |

(56) References Cited

U.S. PATENT DOCUMENTS

| | | |
|---|---|---|
| 5,954,696 A | 9/1999 | Ryan et al. |
| 5,956,023 A | 9/1999 | Lyle et al. |
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |
| 6,027,441 A | 2/2000 | Cantu |
| 6,028,412 A | 2/2000 | Shine et al. |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| RE36,871 E | 9/2000 | Epstein et al. |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,336,053 B1 | 1/2002 | Beatty |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Eiden et al. |
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| 6,540,672 B1 | 4/2003 | Simonsen et al. |
| 6,544,212 B2 | 4/2003 | Galley et al. |
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |
| 6,564,825 B2 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |
| 6,572,545 B2 | 6/2003 | Knobbe et al. |
| 6,572,576 B2 | 6/2003 | Brugger et al. |
| 6,578,422 B2 | 6/2003 | Lam et al. |
| 6,578,435 B2 | 6/2003 | Gould et al. |
| 6,581,117 B1 | 6/2003 | Klein et al. |
| RE38,189 E | 7/2003 | Walker et al. |
| 6,585,675 B1 | 7/2003 | O'Mahony et al. |
| 6,589,229 B1 | 7/2003 | Connelly et al. |
| 6,589,792 B1 | 7/2003 | Malachowski |
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |

(56) References Cited

U.S. PATENT DOCUMENTS

| | | |
|---|---|---|
| 6,606,047 B1 | 8/2003 | Börjesson et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouda et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,171,992 B2 | 2/2007 | DiGianfilippo et al. |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |

(56) References Cited

U.S. PATENT DOCUMENTS

| | | |
|---|---|---|
| 7,291,123 B2 | 11/2007 | Baraldi et al. |
| 7,293,461 B1 | 11/2007 | Gimdt |
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |
| 7,338,470 B2 | 3/2008 | Katz |
| 7,343,224 B2 | 3/2008 | DiGianfilippo et al. |
| 7,347,836 B2 | 3/2008 | Peterson et al. |
| 7,347,854 B2 | 3/2008 | Shelton et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,477,997 B2 | 1/2009 | Kaplit |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| 7,545,075 B2 | 6/2009 | Huang et al. |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,605,730 B2 | 10/2009 | Tomioka et al. |
| 7,614,310 B2 | 11/2009 | Konzelmann |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenskow et al. |
| 7,699,806 B2 | 4/2010 | Ware et al. |
| 7,705,727 B2 | 4/2010 | Pestotnik |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de la Huerga |
| 7,945,452 B2 | 5/2011 | Fathallah et al. |
| 7,976,508 B2 | 7/2011 | Hoag |
| 7,981,073 B2 | 7/2011 | Mollstam |
| 7,981,082 B2 | 7/2011 | Wang et al. |
| 7,998,134 B2 | 8/2011 | Fangrow |
| 8,002,736 B2 | 8/2011 | Patrick et al. |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,514 B2 | 12/2011 | Butterfield et al. |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blomquist |
| 8,175,668 B1 | 5/2012 | Nabutovsky et al. |
| 8,177,739 B2 | 5/2012 | Cartledge et al. |
| 8,180,440 B2 | 5/2012 | McCombie et al. |
| 8,185,322 B2 | 5/2012 | Schroeder et al. |
| 8,197,444 B1 | 6/2012 | Bazargan et al. |
| 8,219,413 B2 | 7/2012 | Martinez et al. |
| 8,221,395 B2 | 7/2012 | Shelton et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| 8,409,164 B2 | 4/2013 | Fangrow |
| 8,449,524 B2 | 5/2013 | Braig et al. |
| 8,469,942 B2 | 6/2013 | Kow et al. |
| 8,477,307 B1 | 7/2013 | Yufa et al. |
| 8,494,879 B2 | 7/2013 | Davis et al. |
| 8,504,179 B2 | 8/2013 | Blomquist |
| 8,506,552 B2 | 8/2013 | Rebours |
| 8,517,990 B2 | 8/2013 | Teel et al. |
| 8,518,021 B2 | 8/2013 | Stewart et al. |
| 8,522,832 B2 | 9/2013 | Lopez et al. |
| 8,523,797 B2 | 9/2013 | Lowery et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| 8,721,584 B2 | 5/2014 | Braithwaite et al. |
| 8,728,020 B2 | 5/2014 | Caleffi et al. |
| 8,758,306 B2 | 6/2014 | Lopez et al. |
| 8,761,906 B2 | 6/2014 | Condurso et al. |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,905,965 B2 | 12/2014 | Mandro et al. |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |

(56) References Cited

U.S. PATENT DOCUMENTS

| | | |
|---|---|---|
| 9,190,010 B2 | 11/2015 | Vik et al. |
| 9,240,002 B2 | 1/2016 | Hume et al. |
| 9,272,089 B2 | 3/2016 | Jacobson et al. |
| 9,316,216 B1 | 4/2016 | Cook et al. |
| 9,333,291 B2 | 5/2016 | Jacobson et al. |
| 9,381,296 B2 | 7/2016 | Arrizza et al. |
| 9,393,362 B2 | 7/2016 | Cozmi et al. |
| 9,468,718 B2 | 10/2016 | Hung et al. |
| 9,498,583 B2 | 11/2016 | Sur et al. |
| 9,545,475 B2 | 1/2017 | Borges et al. |
| 9,545,476 B2 | 1/2017 | Qi et al. |
| 9,707,341 B2 | 7/2017 | Dumas, III et al. |
| 9,764,087 B2 | 9/2017 | Peterfreund et al. |
| 9,852,265 B1 | 12/2017 | Treacy et al. |
| 9,883,987 B2 | 2/2018 | Lopez et al. |
| 9,943,269 B2 | 4/2018 | Muhsin et al. |
| 9,995,611 B2 | 6/2018 | Ruchti et al. |
| 10,022,498 B2 | 7/2018 | Ruchti et al. |
| 10,046,112 B2 | 8/2018 | Oruklu et al. |
| 10,089,055 B1 | 10/2018 | Fryman |
| 10,099,009 B1 | 10/2018 | Anderson et al. |
| 10,166,328 B2 | 1/2019 | Oruklu et al. |
| 10,342,917 B2 | 7/2019 | Shubinsky et al. |
| 10,430,761 B2 | 10/2019 | Hume et al. |
| 10,463,788 B2 | 11/2019 | Day |
| 10,549,248 B2 | 2/2020 | Brown et al. |
| 10,578,474 B2 | 3/2020 | Ruchti et al. |
| 10,596,316 B2 | 3/2020 | Dumas, III et al. |
| 10,635,784 B2 | 4/2020 | Rubalcaba, Jr. et al. |
| 10,656,894 B2 | 5/2020 | Fryman |
| 10,682,102 B2 | 6/2020 | Declerck |
| 10,709,885 B2 | 7/2020 | Janders et al. |
| 10,850,024 B2 | 12/2020 | Day et al. |
| 10,874,793 B2 | 12/2020 | Oruklu et al. |
| 11,004,035 B2 | 5/2021 | Hume et al. |
| 11,007,119 B2 | 5/2021 | Lopez et al. |
| D922,432 S | 6/2021 | Kataoka et al. |
| D923,050 S | 6/2021 | Kataoka et al. |
| 11,029,911 B2 | 6/2021 | Fryman |
| D926,201 S | 7/2021 | Bryant et al. |
| D928,813 S | 8/2021 | Nurutdinov et al. |
| D928,840 S | 8/2021 | Amit et al. |
| 11,090,431 B2 | 8/2021 | Dumas, III et al. |
| D931,884 S | 9/2021 | Bryant et al. |
| 11,135,360 B1 | 10/2021 | Jacobson et al. |
| 11,246,985 B2 | 2/2022 | Gylland et al. |
| 11,278,671 B2 | 3/2022 | Cavendish, Jr. et al. |
| 11,298,456 B2 | 4/2022 | Shubinsky et al. |
| 11,324,888 B2 | 5/2022 | Shubinsky et al. |
| 11,344,668 B2 | 5/2022 | Sileika et al. |
| 11,344,673 B2 | 5/2022 | Lindo et al. |
| 11,376,361 B2 | 7/2022 | Ruchti et al. |
| 11,378,430 B2 | 7/2022 | Ruchti et al. |
| 11,395,875 B2 | 7/2022 | Rubalcaba, Jr. et al. |
| 11,433,177 B2 | 9/2022 | Oruklu et al. |
| 11,439,570 B2 | 9/2022 | Lopez et al. |
| 11,596,737 B2 | 3/2023 | Dumas, III et al. |
| 11,599,854 B2 | 3/2023 | Hume et al. |
| 11,623,042 B2 | 4/2023 | Day |
| 11,868,161 B2 | 1/2024 | Fryman |
| 11,883,361 B2 | 1/2024 | Janssen |
| 11,933,650 B2 | 3/2024 | Ruchti et al. |
| 11,972,395 B2 | 4/2024 | Hume et al. |
| 2001/0007636 A1 | 7/2001 | Butterfield |
| 2001/0014769 A1 | 8/2001 | Bufe et al. |
| 2001/0015099 A1 | 8/2001 | Blaine |
| 2001/0016056 A1 | 8/2001 | Westphal et al. |
| 2001/0032099 A1 | 10/2001 | Joao |
| 2001/0037060 A1 | 11/2001 | Thompson et al. |
| 2001/0041869 A1 | 11/2001 | Causey et al. |
| 2001/0044731 A1 | 11/2001 | Coffman et al. |
| 2002/0003892 A1 | 1/2002 | Iwanaga |
| 2002/0007116 A1 | 1/2002 | Zatezalo et al. |
| 2002/0013545 A1 | 1/2002 | Soltanpour et al. |
| 2002/0013551 A1 | 1/2002 | Zaitsu et al. |
| 2002/0015018 A1 | 2/2002 | Shimazu et al. |
| 2002/0018720 A1 | 2/2002 | Carlisle et al. |
| 2002/0029776 A1 | 3/2002 | Blomquist |
| 2002/0031838 A1 | 3/2002 | Meinhart et al. |
| 2002/0032583 A1 | 3/2002 | Joao |
| 2002/0038392 A1* | 3/2002 | De La Huerga ....... G16H 20/17 710/8 |
| 2002/0040208 A1 | 4/2002 | Flaherty et al. |
| 2002/0044059 A1 | 4/2002 | Reeder et al. |
| 2002/0045806 A1 | 4/2002 | Baker, Jr. et al. |
| 2002/0082728 A1 | 6/2002 | Mueller et al. |
| 2002/0083771 A1 | 7/2002 | Khuri-Yakub et al. |
| 2002/0085952 A1 | 7/2002 | Ellingboe et al. |
| 2002/0087115 A1 | 7/2002 | Hartlaub |
| 2002/0093641 A1 | 7/2002 | Ortyn et al. |
| 2002/0095486 A1 | 7/2002 | Bahl |
| 2002/0099282 A1 | 7/2002 | Knobbe et al. |
| 2002/0099334 A1 | 7/2002 | Hanson et al. |
| 2002/0143580 A1 | 10/2002 | Bristol et al. |
| 2002/0147389 A1 | 10/2002 | Cavallaro et al. |
| 2002/0152239 A1 | 10/2002 | Bautista-Lloyd et al. |
| 2002/0158919 A1 | 10/2002 | Nacey |
| 2002/0168278 A1 | 11/2002 | Jeon et al. |
| 2002/0173703 A1 | 11/2002 | Lebel et al. |
| 2002/0183693 A1 | 12/2002 | Peterson et al. |
| 2003/0009244 A1 | 1/2003 | Engleson |
| 2003/0013959 A1 | 1/2003 | Grunwald et al. |
| 2003/0018289 A1 | 1/2003 | Ng et al. |
| 2003/0018308 A1 | 1/2003 | Tsai |
| 2003/0025602 A1 | 2/2003 | Medema et al. |
| 2003/0028082 A1 | 2/2003 | Thompson |
| 2003/0030001 A1 | 2/2003 | Cooper et al. |
| 2003/0045840 A1 | 3/2003 | Burko |
| 2003/0050621 A1 | 3/2003 | Lebel et al. |
| 2003/0060688 A1 | 3/2003 | Ciarniello et al. |
| 2003/0060765 A1 | 3/2003 | Campbell et al. |
| 2003/0065537 A1 | 4/2003 | Evans |
| 2003/0065589 A1 | 4/2003 | Giacchetti |
| 2003/0073954 A1 | 4/2003 | Moberg et al. |
| 2003/0079746 A1 | 5/2003 | Hickle |
| 2003/0083583 A1 | 5/2003 | Kovtun et al. |
| 2003/0091442 A1 | 5/2003 | Bush et al. |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0135087 A1 | 7/2003 | Hickle et al. |
| 2003/0136193 A1 | 7/2003 | Fujimoto |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158508 A1 | 8/2003 | DiGianfilippo |
| 2003/0159741 A1 | 8/2003 | Sparks |
| 2003/0160683 A1 | 8/2003 | Blomquist |
| 2003/0163789 A1 | 8/2003 | Blomquist |
| 2003/0173408 A1 | 9/2003 | Mosher, Jr. et al. |
| 2003/0186833 A1 | 10/2003 | Huff et al. |
| 2003/0187338 A1 | 10/2003 | Say et al. |
| 2003/0200116 A1 | 10/2003 | Forrester |
| 2003/0204274 A1 | 10/2003 | Ullestad et al. |
| 2003/0204416 A1 | 10/2003 | Acharya |
| 2003/0212364 A1 | 11/2003 | Mann et al. |
| 2003/0212379 A1 | 11/2003 | Bylund et al. |
| 2003/0216682 A1 | 11/2003 | Junker |
| 2003/0217962 A1 | 11/2003 | Childers et al. |
| 2003/0233071 A1 | 12/2003 | Gillespie, Jr. et al. |
| 2004/0030277 A1 | 2/2004 | O'Mahony et al. |
| 2004/0047736 A1 | 3/2004 | Nose et al. |
| 2004/0057226 A1 | 3/2004 | Berthou et al. |
| 2004/0064342 A1 | 4/2004 | Browne et al. |
| 2004/0073125 A1 | 4/2004 | Lovett et al. |
| 2004/0073161 A1 | 4/2004 | Tachibana |
| 2004/0077996 A1 | 4/2004 | Jasperson et al. |
| 2004/0082908 A1 | 4/2004 | Whitehurst |
| 2004/0082918 A1 | 4/2004 | Evans et al. |
| 2004/0104271 A1 | 6/2004 | Martucci et al. |

(56) References Cited

U.S. PATENT DOCUMENTS

| | | |
|---|---|---|
| 2004/0119753 A1 | 6/2004 | Zencke |
| 2004/0120825 A1 | 6/2004 | Bouton et al. |
| 2004/0128162 A1 | 7/2004 | Schlotterbeck et al. |
| 2004/0128163 A1 | 7/2004 | Goodman et al. |
| 2004/0133166 A1 | 7/2004 | Moberg et al. |
| 2004/0145114 A1 | 7/2004 | Ippolito et al. |
| 2004/0147034 A1 | 7/2004 | Gore et al. |
| 2004/0149823 A1 | 8/2004 | Aptekar |
| 2004/0152970 A1 | 8/2004 | Hunter et al. |
| 2004/0158193 A1 | 8/2004 | Bui et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172289 A1 | 9/2004 | Kozic et al. |
| 2004/0172301 A1 | 9/2004 | Mihai et al. |
| 2004/0172302 A1 | 9/2004 | Martucci et al. |
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1 | 1/2005 | Campbell et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0108057 A1 | 5/2005 | Cohen et al. |
| 2005/0119597 A1 | 6/2005 | O'Mahony et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0143864 A1 | 6/2005 | Blomquist |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136095 A1 | 6/2006 | Rob et al. |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0180916 A1 | 8/2006 | Wyland |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229918 A1 | 10/2006 | Fotsch et al. |
| 2006/0235353 A1 | 10/2006 | Gelfand et al. |
| 2006/0255149 A1 | 11/2006 | Retter et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0265246 A1 | 11/2006 | Hoag |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060869 A1 | 3/2007 | Tolle et al. |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084286 A1 | 4/2007 | Ajay et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0094045 A1 | 4/2007 | Cobbs et al. |
| 2007/0094046 A1 | 4/2007 | Cobbs et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0156456 A1 | 7/2007 | McGillin et al. |
| 2007/0179436 A1 | 8/2007 | Braig et al. |
| 2007/0180916 A1 | 8/2007 | Tian et al. |
| 2007/0191770 A1 | 8/2007 | Moberg et al. |
| 2007/0191817 A1 | 8/2007 | Martin |
| 2007/0197963 A1 | 8/2007 | Griffiths et al. |

(56) References Cited

U.S. PATENT DOCUMENTS

| | | |
|---|---|---|
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0250339 A1 | 10/2007 | Mallett et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0077116 A1 | 3/2008 | Dailey et al. |
| 2008/0086087 A1 | 4/2008 | Spohn et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0169044 A1 | 7/2008 | Osborne et al. |
| 2008/0172030 A1 | 7/2008 | Blomquist et al. |
| 2008/0177254 A1 | 7/2008 | Shelton et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0099866 A1 | 4/2009 | Newman |
| 2009/0105636 A1 | 4/2009 | Hayter et al. |
| 2009/0112155 A1 | 4/2009 | Zhao |
| 2009/0114037 A1 | 5/2009 | Smith |
| 2009/0119330 A1 | 5/2009 | Sampath et al. |
| 2009/0124963 A1 | 5/2009 | Hogard et al. |
| 2009/0124964 A1 | 5/2009 | Leach et al. |
| 2009/0126825 A1 | 5/2009 | Eliuk et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0171289 A1 | 7/2009 | Davis et al. |
| 2009/0177146 A1 | 7/2009 | Nesbitt et al. |
| 2009/0177180 A1 | 7/2009 | Rubalcaba et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0177992 A1 | 7/2009 | Rubalcaba et al. |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0198347 A1 | 8/2009 | Kirzinger |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2010/0022988 A1 | 1/2010 | Wochner |
| 2010/0280430 A1 | 1/2010 | Caleffi et al. |
| 2010/0036310 A1 | 2/2010 | Hillman |
| 2010/0056992 A1 | 3/2010 | Hayter |
| 2010/0057042 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1 | 5/2010 | Jacobson et al. |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0185182 A1 | 7/2010 | Alme et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0217154 A1 | 8/2010 | Deshmukh et al. |
| 2010/0217621 A1 | 8/2010 | Schoenberg |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0312039 A1 | 12/2010 | Quirico et al. |
| 2010/0317093 A1 | 12/2010 | Turewicz et al. |
| 2010/0317952 A1 | 12/2010 | Budiman et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0040247 A1 | 2/2011 | Mandro et al. |
| 2011/0046558 A1 | 2/2011 | Gravesen et al. |
| 2011/0054311 A1 | 3/2011 | Williams et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |

(56) References Cited

U.S. PATENT DOCUMENTS

| | | |
|---|---|---|
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0107251 A1 | 5/2011 | Guaitoli et al. |
| 2011/0137241 A1 | 6/2011 | DelCastillo et al. |
| 2011/0144595 A1 | 6/2011 | Cheng |
| 2011/0152770 A1 | 6/2011 | Diperna et al. |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0218514 A1 | 9/2011 | Rebours |
| 2011/0238032 A1* | 9/2011 | McTaggart ............ G16H 20/17 700/282 |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0313390 A1 | 12/2011 | Roy et al. |
| 2011/0319728 A1 | 12/2011 | Petisce et al. |
| 2011/0320049 A1 | 12/2011 | Chossat et al. |
| 2012/0016215 A1 | 1/2012 | Condurso et al. |
| 2012/0025995 A1 | 2/2012 | Moberg et al. |
| 2012/0059234 A1 | 3/2012 | Barrett et al. |
| 2012/0068001 A1 | 3/2012 | Pushkarsky et al. |
| 2012/0083760 A1 | 4/2012 | Ledford et al. |
| 2012/0089411 A1 | 4/2012 | Srnka et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0222774 A1 | 9/2012 | Husnu et al. |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2012/0310204 A1 | 12/2012 | Krogh et al. |
| 2012/0323212 A1 | 12/2012 | Murphy |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0032634 A1 | 2/2013 | McKirdy |
| 2013/0041342 A1 | 2/2013 | Bernini et al. |
| 2013/0044111 A1 | 2/2013 | VanGilder et al. |
| 2013/0110538 A1 | 5/2013 | Butterfield et al. |
| 2013/0150766 A1 | 6/2013 | Olde et al. |
| 2013/0150821 A1 | 6/2013 | Bollish et al. |
| 2013/0177455 A1* | 7/2013 | Kamen ................ F04B 43/12 417/313 |
| 2013/0184676 A1 | 7/2013 | Kamen et al. |
| 2013/0197930 A1 | 8/2013 | Garibaldi et al. |
| 2013/0201482 A1 | 8/2013 | Munro |
| 2013/0218080 A1 | 8/2013 | Peterfreund et al. |
| 2013/0116649 A1 | 9/2013 | Kouyoumjian et al. |
| 2013/0253430 A1 | 9/2013 | Kouyoumjian et al. |
| 2013/0253946 A1 | 9/2013 | Broselow |
| 2013/0274576 A1 | 10/2013 | Amirouche et al. |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0322201 A1 | 12/2013 | Hitchcock et al. |
| 2013/0345658 A1 | 12/2013 | Browne et al. |
| 2013/0345666 A1 | 12/2013 | Panduro et al. |
| 2014/0039446 A1 | 2/2014 | Day |
| 2014/0067425 A1 | 3/2014 | Dudar et al. |
| 2014/0145915 A1 | 5/2014 | Ribble et al. |
| 2014/0180711 A1 | 6/2014 | Kamen et al. |
| 2014/0224829 A1 | 8/2014 | Capone et al. |
| 2014/0267563 A1 | 9/2014 | Baca et al. |
| 2014/0303754 A1 | 10/2014 | Nixon et al. |
| 2014/0358077 A1 | 12/2014 | Oruklu et al. |
| 2015/0025453 A1 | 1/2015 | Ledford et al. |
| 2015/0033073 A1 | 1/2015 | Yang et al. |
| 2015/0051458 A1 | 2/2015 | Chen |
| 2015/0065988 A1 | 3/2015 | Holderle et al. |
| 2015/0114515 A1 | 4/2015 | Phallen |
| 2015/0141921 A1 | 5/2015 | Stewart et al. |
| 2015/0168958 A1 | 6/2015 | Downie et al. |
| 2015/0224252 A1 | 8/2015 | Borges et al. |
| 2015/0246175 A1 | 9/2015 | Shubinsky et al. |
| 2015/0265765 A1 | 9/2015 | Yavorsky et al. |
| 2015/0338340 A1 | 11/2015 | Jiang et al. |
| 2015/0343141 A1 | 12/2015 | Lindo et al. |
| 2015/0371004 A1 | 12/2015 | Jones |
| 2016/0042264 A1 | 2/2016 | Borges et al. |
| 2016/0051750 A1 | 2/2016 | Tsoukalis |
| 2016/0103960 A1 | 4/2016 | Hume et al. |
| 2016/0110088 A1 | 4/2016 | Vik et al. |
| 2016/0144101 A1 | 5/2016 | Pananen |
| 2016/0151560 A1 | 6/2016 | Toro et al. |
| 2016/0151562 A1 | 6/2016 | Magers et al. |
| 2016/0151601 A1 | 6/2016 | Cardelius et al. |
| 2016/0158437 A1 | 6/2016 | Biasi et al. |
| 2016/0175517 A1 | 6/2016 | Sileika et al. |
| 2016/0193604 A1 | 7/2016 | McFarland et al. |
| 2016/0253460 A1 | 9/2016 | Kanada |
| 2016/0339167 A1 | 11/2016 | Ledford et al. |
| 2017/0043089 A1 | 2/2017 | Handler |
| 2017/0132867 A1 | 5/2017 | Berg et al. |
| 2017/0354941 A1 | 12/2017 | Brown et al. |
| 2018/0018440 A1 | 1/2018 | Sugawara |
| 2018/0028749 A1 | 2/2018 | Dumas, III et al. |
| 2018/0300994 A1 | 10/2018 | Nelson et al. |
| 2019/0091401 A1 | 3/2019 | Ruchti et al. |
| 2019/0101425 A1 | 4/2019 | Ruchti et al. |
| 2019/0117890 A1 | 4/2019 | Oruklu et al. |
| 2019/0196770 A1 | 6/2019 | Fryman |
| 2019/0262535 A1 | 8/2019 | Shubinsky et al. |
| 2019/0282757 A1 | 9/2019 | Gylland et al. |
| 2019/0351131 A1 | 11/2019 | Butterfield et al. |
| 2020/0069864 A1 | 3/2020 | Shubinsky et al. |
| 2020/0113784 A1 | 4/2020 | Lopez et al. |
| 2020/0238007 A1 | 7/2020 | Day |
| 2020/0271499 A1 | 8/2020 | Ruchti et al. |
| 2020/0282137 A1 | 9/2020 | Dumas, III et al. |
| 2020/0324044 A1 | 10/2020 | Gylland et al. |
| 2020/0330689 A1 | 10/2020 | Nemoto et al. |
| 2020/0357500 A1 | 11/2020 | Rubalcaba, Jr. et al. |
| 2021/0162115 A1 | 6/2021 | Surine |
| 2021/0170101 A1 | 6/2021 | Cavendish, Jr. et al. |
| 2021/0260283 A1 | 8/2021 | Oruklu et al. |
| 2021/0304864 A1 | 9/2021 | Kamen et al. |
| 2021/0397396 A1 | 12/2021 | Fryman |
| 2022/0142865 A1 | 5/2022 | Janssen |
| 2022/0176037 A1 | 6/2022 | Jacobson et al. |
| 2022/0184302 A1 | 6/2022 | Cavendish, Jr. et al. |
| 2022/0296806 A1 | 9/2022 | Shubinsky et al. |
| 2022/0305200 A1 | 9/2022 | Gylland et al. |
| 2022/0331518 A1 | 10/2022 | Shubinsky et al. |
| 2022/0362463 A1 | 11/2022 | Lindo et al. |
| 2023/0010290 A1 | 1/2023 | Oruklu et al. |
| 2023/0010638 A1 | 1/2023 | Rubalcaba, Jr. et al. |
| 2023/0017117 A1 | 1/2023 | Sileika et al. |
| 2023/0058662 A1 | 2/2023 | Ruchti et al. |
| 2023/0058894 A1 | 2/2023 | Ruchti et al. |
| 2023/0112979 A1 | 4/2023 | Xavier |
| 2023/0115595 A1 | 4/2023 | Cousineau et al. |
| 2023/0181419 A1 | 6/2023 | Fister |
| 2023/0270938 A1 | 8/2023 | Dumas, III et al. |
| 2023/0285669 A1 | 9/2023 | Day |
| 2023/0310735 A1 | 10/2023 | Cousineau |
| 2023/0325772 A1 | 10/2023 | Hume et al. |

(56) References Cited

U.S. PATENT DOCUMENTS

FOREIGN PATENT DOCUMENTS

| | | |
|---|---|---|
| CA | 2 113 473 | 3/1993 |
| CA | 2 551 817 | 7/2005 |
| CA | 2 554 407 | 8/2005 |
| CN | 107106042 | 8/2017 |
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 814 864 | 1/1998 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 1 490 131 | 12/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-518471 | 7/2007 |
| JP | 2007-520270 | 7/2007 |
| JP | 2007-275106 | 10/2007 |
| JP | 2008-249400 | 10/2008 |
| JP | 4322661 | 6/2009 |
| JP | 2009-148592 | 7/2009 |
| JP | 2010-063767 | 3/2010 |
| JP | 5716879 | 3/2015 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/010029 | 3/1999 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/061745 | 7/2004 |
| WO | WO 2004/070556 | 8/2004 |
| WO | WO 2004/070994 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2006/026270 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |

(56) References Cited

FOREIGN PATENT DOCUMENTS

| | | |
|---|---|---|
| WO | WO 2009/023407 | 2/2009 |
| WO | WO 2009/023634 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/036854 | 3/2013 |
| WO | WO 2013/096769 | 6/2013 |
| WO | WO 2015/134478 | 9/2015 |
| WO | WO 2017/051271 | 3/2017 |
| WO | WO 2017/144366 | 8/2017 |
| WO | WO 2017/197024 | 11/2017 |
| WO | WO 2019/092680 | 5/2019 |
| WO | WO 2020/214717 | 10/2020 |
| WO | WO 2022/020184 | 1/2022 |
| WO | WO 2022/125471 | 6/2022 |
| WO | WO 2023/064662 | 4/2023 |
| WO | WO 2023/108030 | 6/2023 |
| WO | WO 2023/192791 | 10/2023 |
| WO | WO 2023/244922 | 12/2023 |

OTHER PUBLICATIONS

Daimiwal et al., "Wireless Transfusion Supervision and Analysis Using Embedded System", IEEE, 2010 International Conference ICBBT, China, Apr. 2010, pp. 56-60.
Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.
ALARIS® Medical Systems, "Signature Edition® GOLD—Single & Dual Channel Infusion System", San Diego, CA, USA, date unknown, but believed to be at least as early as Nov. 29, 2008, pp. 2-88 & 2-91.
Allegro, "3955—Full-Bridge PWM Microstepping Motor Drive", Datasheet, 1997, pp. 16.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
Baxter, "Baxter Receives 510(k) Clearance for Next-Generation SIGMA Spectrum Infusion Pump with Master Drug Library" Press Release, May 8, 2014, pp. 2. http://web.archive.org/web/20160403140025/http://www.baxter.com/news-media/newsroom/press-releases/2014/05_08_14_sigma.page.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.
Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.
Buhrdorf et al., "Capacitive Micromachined Ultrasonic Transducers and their Application", Proceedings of the IEEE Ultrasonics Symposium, Feb. 2001, vol. 2, pp. 933-940.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
Cheung et al., "Hyperglycemia is Associated with Adverse Outcomes in Patients Receiving Total Parenteral Nutrition", Diabetes Care, Oct. 2005, vol. 28, No. 10, pp. 2367-2371.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", https://web.archive.org/web/20090813092423/http://www.diffen.com/difference/Continually_vs_Continuously, as accessed Aug. 13, 2009 in 4 pages.
"CritiCore® Monitor: Critical Fluid Output and Core Bladder Temperature Monitor", BARD Urological Catheter Systems, Advertisement, 2005, pp. 2.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. http://archive.epo.org/epo/pubs/oj013/11_13/11_5033.pdf.
"Decision of the Administrative Council of Oct. 27, 2009 Amending the Implementing Regulations to the European Patent Convention (CA/D 20/09)", Official Journal EPO Dec. 2009, Dec. 2009, pp. 582-584. http://archive.epo.org/epo/pubs/oj009/12_09/12_5829.pdf.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
"Froth", http://www.merriam-webster.com/dictionary/froth, as accessed May 13, 2015 in 1 page.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. www.hospira.com/products_and_services/infusion_pumps/plum/index.
Hospira, "Plum XL™ Series Infusion System" Technical Service Manual, Feb. 2005, Lake Forest, Illinois, USA, pp. i-vii, 5-14, 8-3.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.

(56) References Cited

OTHER PUBLICATIONS

Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
JMS Co., Ltd., "Infusion Pump: OT-701", Tokyo, Japan, 2002, pp. 4.
Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.
Kutcher et al., "The Effect of Lighting Conditions on Caries Interpretation with a Laptop Computer in a Clinical Setting", Elsevier, Oct. 2006, vol. 102, No. 4, pp. 537-543.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Merry et al., "A New, Safety-Oriented, Integrated Drug Administration and Automated Anesthesia Record System", Anesthesia & Analgesia, Aug. 2001, vol. 93, No. 2 pp. 385-390.
Microchip Technology Inc., "MTA11200B; TrueGauge™ Intelligent Battery Management I.C.", https://www.elektronik.ropla.eu/pdf/stock/mcp/mta11200b.pdf, 1995, pp. 44.
Moghissi, Etie, MD, FACP, FACE, "Hyperglycemia in Hospitalized Patients", A Supplement to ACP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS-Thomson Microelectronics, "L6219—Stepper Motor Drive", Datasheet, Dec. 1996, pp. 10.
SGS-Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.
Tang et al., "Linear Dimensionality Reduction Using Relevance Weighted LDA", Pattern Recognition, 2005, vol. 38, pp. 485-493, http://staff.ustc.edu.cn/~ketang/papers/TangSuganYaoQin_PR04.pdf.
Thomas et al., "Implementation of a Tight Glycaemic Control Protocol Using a Web-Based Insulin Dose Calculator", Anaesthesia, 2005, vol. 60, pp. 1093-1100.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Westbrook et al., "Errors in the Administration of Intravenous Medications in Hospital and the Role of Correct Procedures and Nurse Experience", BMJ Quality & Safety, 2011, vol. 20, pp. 1027-1034.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
International Search Report and Written Opinion received in PCT Application No. PCT/US2016/020355, dated Jul. 26, 2016 in 15 pages.
International Preliminary Report on Patentability and Written Opinion received in PCT Application No. PCT/US2016/020355, dated Sep. 14, 2017 in 12 pages.
Junda, Lin, "Global development trends of green bonds", Jul. 10, 2018, pp. 9.
Notice of Opposition in European Patent Application No. 16759381.3 (Patent No. EP3285827), dated May 31, 2023 in 48 pages.
Response to Notice of Opposition in European Patent Application No. 16759381.3 (Patent No. EP3285827), dated Oct. 23, 2023 in 63 pages.
Response from the Opposer to patentee's submission in European Patent Application No. 16759381.3 (Patent No. EP3285827), dated Apr. 25, 2024 in 54 pages.
Summons to attend oral proceedings and preliminary opinion of Opposition Division submission in European Patent Application No. 16759381.3 (Patent No. EP3285827), dated May 23, 2024 in 18 pages.

* cited by examiner

```
CURRENTLY SPECIFIED STEPS IN THIS INFUSION
① CURRENT INFUSER - LINE A        SALINE
                RATE:100 mL/hr       VTBI:100 mL         TIME: 1hr 00 min
② CURRENT INFUSER - LINE A        HEPARIN (25,000 UNITS / 250 mL)
   DOSE: 1,200 UNITS/HR  RATE:12 mL/hr   VTBI:100 mL     TIME: 20 hrs 50 min
③ CURRENT INFUSER - LINE A        SALINE
                RATE:100 mL/hr       VTBI:100 mL         TIME: 1hr 00 min
④ CURRENT INFUSER - LINE C        DOPAMINE (400 mg/250 mL)
   DOSE: 5 mcg/kg/hr HR  RATE:15.3 mL/hr  VTBI:250 mL    TIME: 15hrs 43 min
⑤ CURRENT INFUSER - LINE A        SALINE
                RATE:100 mL/hr       VTBI:100 mL         TIME: 1hr 00 min

ADD STEP  CLEAR   CLEAR  OPTIONS  STEPS
```

FIG. 30

```
SELECTED LINE  >  LINE A - PRIMARY (STEP 2 OF 5)
INFUSION  >  HEPARIN
             (25,000 units/250 mL)
DOSE      >  1,200   units/hr
WEIGHT & BSA
RATE      >  12      mL/hr
VTBI      >  250     mL  INFINIFLOW
TIME      >  20:50   hh:mm

[+]      [+]     [🗑]    [...]   [88]   CONFIRM
ADD STEP CLONE  CLEAR  OPTIONS  STEPS
```

FIG. 31

CURRENTLY SPECIFIED STEPS IN THIS INFUSION

① CURRENT INFUSER – LINE A        SALINE
                    RATE:100 mL/hr        VTBI:100 mL        TIME: 1hr 00 min ② CURRENT INFUSER – LINE A        HEPARIN (25,000 UNITS / 250 mL)
DOSE: 1,200 UNITS/HR  RATE:12 mL/hr        VTBI:250 mL        TIME: 20 hrs 50 min

③ CURRENT INFUSER – LINE A        SALINE

④ CURRENT INFUSER – LINE C        DOPAMINE (400 mg/250 mL)
DOSE: 5 mcg/kg/hr HR  RATE:15.3 mL/hr   VTBI:250 mL        TIME: 15hrs 43 min ⑤ CURRENT INFUSER – LINE A        SALINE
                    RATE:100 mL/hr        VTBI:100 mL        TIME: 1hr 00 min

ADD STEP  CLEAR   CLEAR  OPTIONS  STEPS

CURRENTLY SPECIFIED STEPS IN THIS INFUSION

① CURRENT INFUSER – LINE A        SALINE
                    RATE:100 mL/hr        VTBI:100 mL        TIME: 1hr 00 min ② CURRENT INFUSER – LINE A        HEPARIN (25,000 UNITS / 250 mL)
DOSE: 1,200 UNITS/HR  RATE:12 mL/hr        VTBI:250 mL        TIME: 20 hrs 50 min ③ CURRENT INFUSER – LINE A        SALINE
                    RATE:100 mL/hr        VTBI:100 mL        TIME: 1hr 00 min ④ CURRENT INFUSER – LINE C        DOPAMINE (400 mg/250 mL)
DOSE: 5 mcg/kg/hr HR  RATE:15.3 mL/hr  VTBI:250 mL        TIME: 15hr ⑤ CURRE  FUSER – LINE A        SALINE
                    RATE:100 mL/hr        VTBI:100 mL        TIME: 1hr 00 min

ADD STEP  CLEAR   CLEAR  OPTIONS  STEPS

AFTER SWIPE → | STEP DELETED           ↻ TAP TO UNDO |

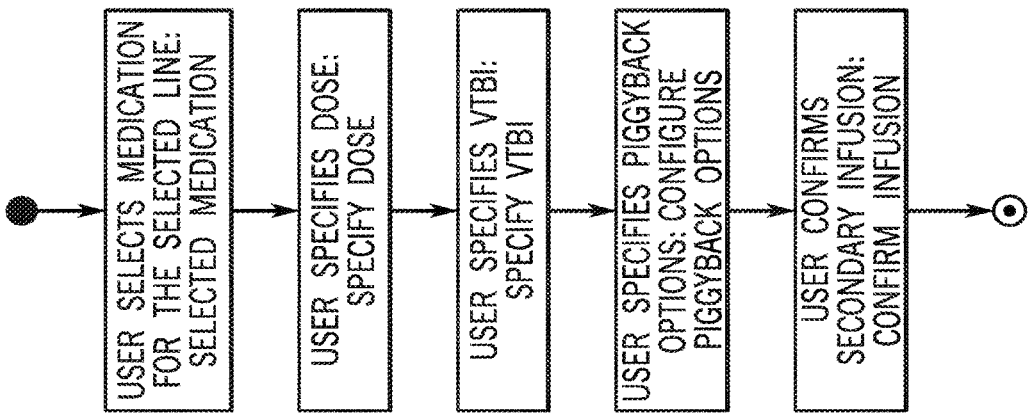
FIG. 62
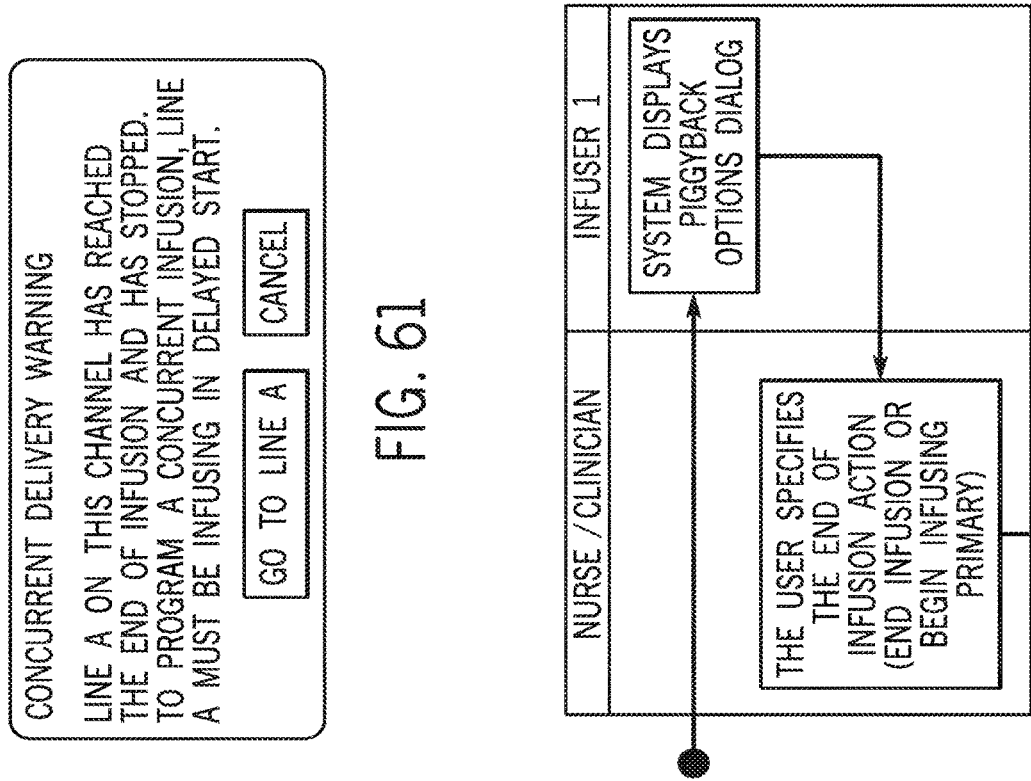
FIG. 61
FIG. 63

INFUSION SYSTEM, DEVICE, AND METHOD HAVING ADVANCED INFUSION FEATURES

TECHNICAL FIELD

The present application is generally related to the automated administration of a medication therapy. More particularly, the present application is directed toward configuring and managing delivery of medications in systems and methods that include infusion devices.

BACKGROUND

Modern medical devices, including infusion devices, are increasingly being controlled by microprocessor based systems to deliver substances such as fluids, solutions, medications, and drugs to patients. A typical control for an infusion device includes a user interface enabling a medical practitioner to enter a dosage of fluid to be delivered, the rate of fluid delivery, the duration, and the volume of a fluid to be infused into a patient. To deliver medications to the patient, an infusion device typically includes a pump and a fluid delivery device such as a syringe, tubing, section of tubing, or cassette.

Existing infusion devices, however, might be limited in various ways. As one example, while multi-channel infusion devices might be able to deliver multiple medications to a patient, these infusion devices might be limited in the number of medications they can deliver and in their ability to interoperate with other infusion devices of different types. As a result, existing infusion devices might not be suitable or even capable of providing complex medication therapies involving multiple medications delivered in particular sequences. Therefore a need exists for advanced systems and devices for delivering substances to patients.

BRIEF DESCRIPTION OF THE DRAWINGS

Aspects of the disclosure may be implemented in certain parts, steps, and embodiments that will be described in detail in the following description and illustrated in the accompanying drawings in which like reference numerals indicate similar elements. It will be appreciated with the benefit of this disclosure that the steps illustrated in the accompanying figures may be performed in other than the recited order and that one or more of the steps may be optional. It will also be appreciated with the benefit of this disclosure that one or more components illustrated in the accompanying figures may be positioned in other than the disclosed arrangement and that one or more of the components illustrated may be optional. Furthermore a set of elements is intended to include one or more elements.

FIG. 30 depicts an example user interface displaying a list of infusion sequence steps for an infusion to be delivered by an infusion device.

FIG. 31 depicts an example user interface of an infusion device for displaying the parameters associated with a step the caregiver has selected in the list of infusion steps.

FIG. 32 depicts the user interface of FIG. 30 in which the caregiver has selected one of the steps (step no. 4) in the list of infusion steps.

FIG. 33 depicts the user interface of FIG. 32 in which the caregiver has dragged the selected step to the right to remove it from the list.

FIG. 36 depicts an example user interface for cloning a current step of an intermittent infusion.

FIG. 59 depicts a user interface for configuring the first delivery of the second step of an inter-channel sequencing infusion.

FIG. 60 depicts a user interface for configuring the second delivery of the sixth step of an inter-channel sequencing infusion.

FIG. 61 depicts an example user interface of an infusion device for notifying or warning a caregiver regarding a non-delivery condition.

FIG. 62 depicts a flowchart of example method steps for configuring a piggyback infusion at an infusion device.

FIG. 63 depicts a flowchart of example method steps for configuring piggyback infusion options including selecting or specifying an action to perform at the end of the piggyback infusion.

DETAILED DESCRIPTION

Figure 1:
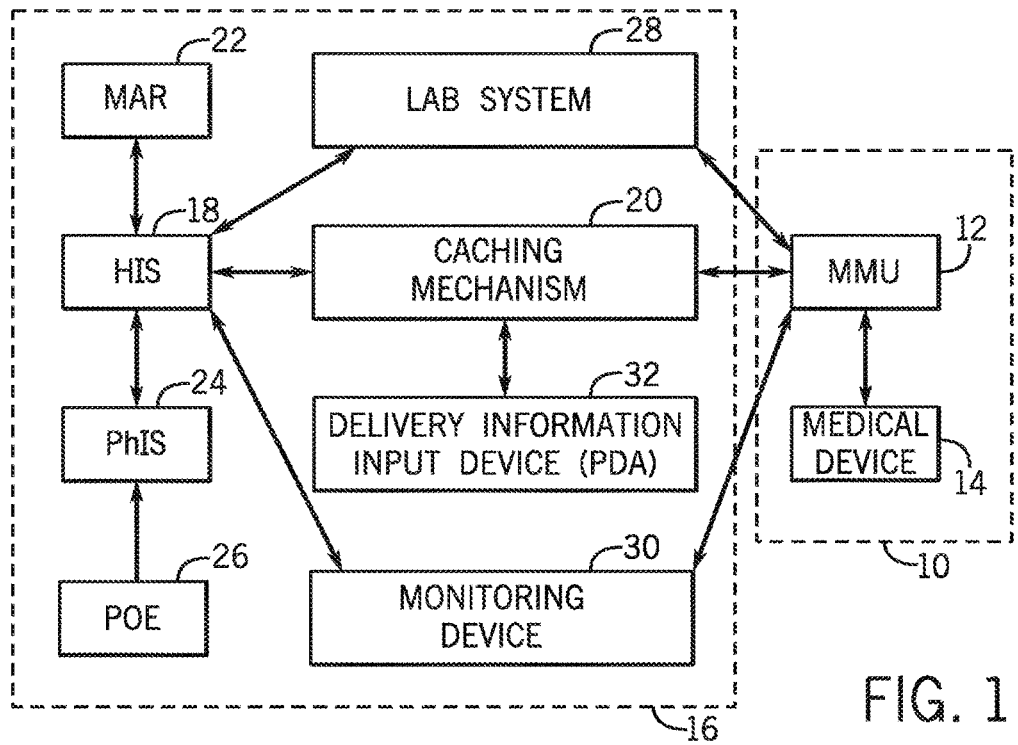
FIG. 1 depicts a schematic diagram of an example medication management system including an example medical management unit and an example medical device.

In general the present disclosure provides systems, devices, and methods for delivering substances such as fluids, solutions, medications, and drugs to patients using infusion devices having a set of advanced features. These advanced features include aspects related to the programming of infusion devices, the configuration of infusion sequences performed by the infusion devices, and the interconnection of multiple infusion devices for interoperation during an infusion having a sequence of infusion steps.

The aspects described herein may be employed using infusion products available from Hospira Worldwide, Inc. ("Hospira") headquartered in Lake Forest, Ill. Examples of infusion systems that may be utilized include the Plum A+™ Infusion System and the Plum A+3™ Infusion System available from Hospira. The infusion systems may utilize the PlumSet™ cassette also available from Hospira. The cassette may be a dual-input cassette with two input ports from respective delivery sources and one output port to the patient. The deliver source may be, e.g., a bottle, bag, or other type of container suitable for infusion procedures. The dual-input cassette thus provides the ability to deliver two infusions to the patient via the same infusion channel. The dual-input cassette thus provides opportunities to provide infusion systems, devices, and methods with advanced infusion features.

As described in further detail below, infusion systems, devices, and methods may include the following advanced infusion features. One advanced infusion feature allows a caregiver to dynamically configure the parameters of a current ongoing infusion as well as add steps to a current ongoing infusion. This advanced infusion feature advantageously allows the caregiver to convert the current infusion type to another type of infusion. This advanced infusion feature also advantageously allows the caregiver to initiate the first step of an infusion while configuring the subsequent steps of the infusion. As described in further detail below, an infusion device may provide a user interface that allows a caregiver to select and configure infusion steps, e.g., selecting the infusion type and infusion parameters, arranging the sequence of infusion steps, and confirming individual infusion steps and the overall infusion sequence.

Another advanced infusion feature interconnects multiple infusion devices via a network in a master/slave configuration. This feature provides protocols for discovering interconnected infusion devices available for selection, designating an infusion device as the master infusion device, and selecting one or more slave infusion devices. As described in further detail below, different techniques may be employed to designate the master infusion device and select the slave infusion devices depending on whether the infusion devices are interconnected via a physical or wireless connection. This feature also provides protocols for designating a new master infusion device if the slave infusion devices lose the connection with the current master infusion device.

The master/slave configuration of the infusion devices allows for advanced infusion features related to inter-channel and inter-device sequencing of infusion steps. As also described in further detail below, a caregiver may program infusion steps between different types of infusion devices may program infusion steps with multiple deliveries via multiple channels per step. In this way, the advanced infusion features allow the caregiver to configure complex sequences of infusion steps involving multiple delivery sources, multiple infusion devices, and multiple channels.

Interconnecting the infusion devices also provides various safety features. As one example, the total infusion rate across all infusion devices associated with a patient may be limited. As another example, the total amount of air accumulated across all infusion devices associated with the patient may be tracked, and an alarm may be provided to a caregiver if the total amount of accumulated air reaches a predetermined threshold. In a further example, duplication and compatibility safety checks for multiple infusion devices connected to the same access site, and a notification indicating duplicate or incompatible substances may be provided to a caregiver who may have the ability to review and override any conflicts.

These and additional aspects will be appreciated with the benefit of the disclosures provided in further detail below.

Medication Management Systems, Medical Managements Units, and Medical Devices

As a brief introduction to the aspects discussed in further detail below, the following description of medication management systems, medical management units and medical devices is provided.

FIG. 1 depicts an example medication management system including an example medical management unit and an example medical device. The medication management system (MMS) 10 includes a medication management unit (MMU) 12 and a medical device 14, typically operating in conjunction with one or more information systems or components of a hospital environment 16. The term hospital environment should be construed broadly herein to mean any medical care facility, including but not limited to a hospital, treatment center, clinic, doctor's office, day surgery center, hospice, nursing home, and any of the above associated with a home care environment. There can be a variety of information systems in a hospital environment. As shown in FIG. 1, the MMU 12 communicates to a hospital information system (HIS) 18 via a caching mechanism 20 that is part of the hospital environment 16.

The caching mechanism 20 is primarily a pass through device for facilitating communication with the HIS 18 and its functions can be eliminated or incorporated into the MMU 12 and/or the medical device 14 and/or the HIS 18 and/or other information systems or components within the hospital environment 16. The caching mechanism 20 provides temporary storage of hospital information data separate from the HIS 18, the medication administration record system (MAR) 22, pharmacy information system (PhIS) 24, physician order entry (POE) 26, and/or Lab System 28. The caching mechanism 20 provides information storage accessible to the MMS 10 to support scenarios where direct access to data within the hospital environment 16 is not available or not desired. For example, the caching mechanism 20 provides continued flow of information in and out of the MMU 12 in instances where the HIS 18 is down or the connectivity between the MMU 12 and an electronic network is down.

The HIS 18 communicates with a MAR 22 for maintaining medication records and a PhIS 24 for delivering drug orders to the HIS. A POE device 26 permits a healthcare provider to deliver a medication order prescribed for a patient to the hospital information system directly or indirectly via the PhIS 24. A medication order can be sent to the MMU 12 directly from the PhIS 24 or POE device 26. As used herein the term medication order is defined as an order to administer something that has a physiological impact on a person or animal, including but not limited to liquid or gaseous fluids, drugs or medicines, liquid nutritional products and combinations thereof.

Lab system 28 and monitoring device 30 also communicate with the MMU 12 to deliver updated patient-specific information to the MMU 12. As shown, the MMU 12 communicates directly to the lab system 28 and monitoring device 30. However the MMU 12 can communicate to the lab system 28 and monitoring device 30 indirectly via the HIS 18, the caching mechanism 20, the medical device 14 or some other intermediary device or system.

Delivery information input device 32 also communicates with the MMU 12 to assist in processing drug orders for delivery through the MMU 12. The delivery information input device 32 can be any sort of data input means, including those adapted to read machine readable indicia such as barcode labels; for example a personal digital assistant (PDA) with a barcode scanner. Hereinafter the delivery information input device 32 will be referred to as input device 32. Alternatively, the machine readable indicia may be in other known forms, such as radio frequency identification (RFID) tag, two-dimensional bar code, ID matrix, transmitted radio ID code, human biometric data such as fingerprints, etc. and the input device 32 adapted to "read" or recognize such indicia. The input device 32 is shown as a separate device from the medical device 14; alternatively, the input device 32 communicates directly with the medical device 14 or may be integrated wholly or in part with the medical device.

Figure 2:
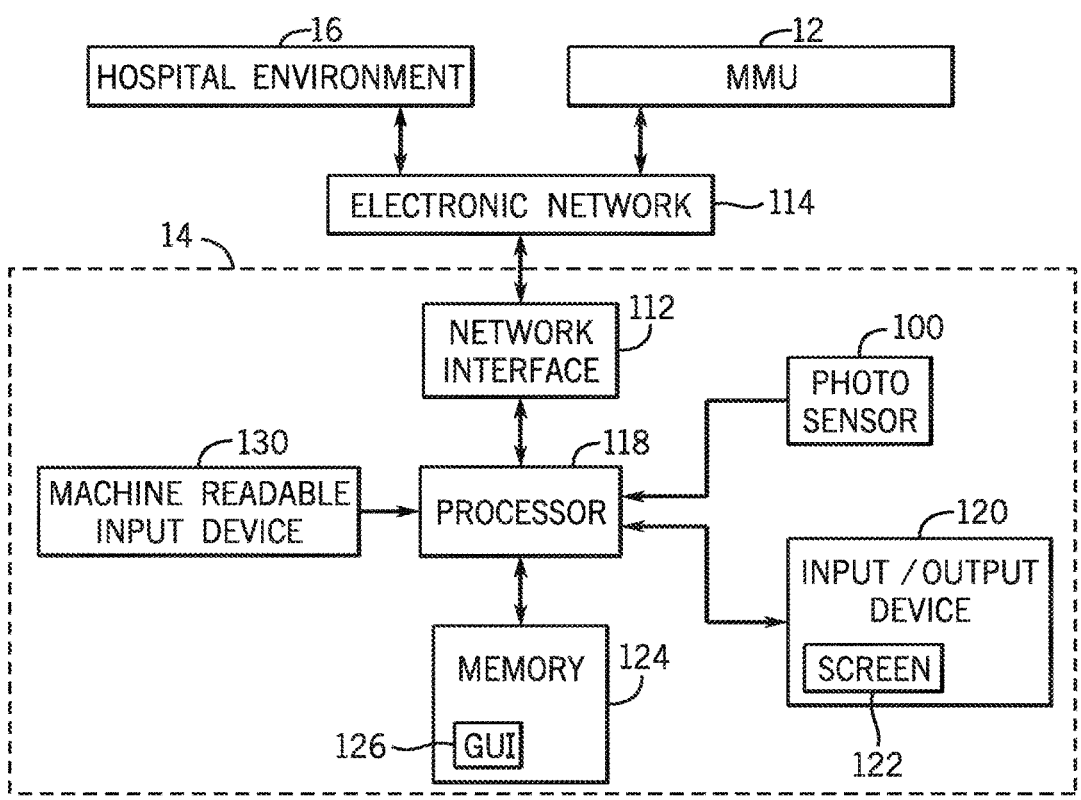
FIG. 2 depicts a schematic diagram of an example medical device.

With reference to FIG. 2, an electronic network 114 connects the MMU 12, medical device 14, and hospital environment 16 for electronic communication. The electronic network 114 can be a completely wireless network, a completely hard wired network, or some combination thereof.

FIG. 2 is a schematic diagram illustrating several functional components of a medical device 14 for implementing aspects of the present disclosure. The device 14 includes many more components than those shown in FIG. 4. However, it is not necessary that all these components be shown in order to disclose an illustrative embodiment for practicing aspects of the present disclosure.

In the context of the present disclosure, the term "medical device" includes without limitation a device that acts upon a cassette, reservoir, vial, syringe, or tubing to convey medication or fluid to or from a patient (for example, an enteral pump, a parenteral infusion pump, a patient controlled analgesia (PCA) or pain management medication pump, or a suction pump), a monitor for monitoring patient vital signs or other parameters, or a diagnostic, testing or sampling device.

For the purpose of exemplary illustration only, the medical device 14 is disclosed as an infusion pump. More particularly, the medical device 14 can be a single channel infusion pump, a multi-channel infusion pump (as shown), or some combination thereof.

The medical device 14 in FIG. 2 is a pump-style medical device and includes a network interface 112 for connecting the medical device 14 to electronic network 114. Where a wireless connection to the electronic network 114 is desired, network interface 112 operates an antenna for wireless connection to the electronic network 114. The antenna can project outside the device 14 or be enclosed within the housing of the device.

A processor 118 is included in the medical device 14 and performs various operations described in greater detail below. The input/output device 120 allows the caregiver to receive output from the medical device 14 and/or input information into the medical device 14. The input/output device 120 may be provided as a single device such as a touch screen 122, or as a separate display device and a separate input device. The display screen 122 of the medical pump 14 may be a thin film transistor active matrix color liquid crystal display with a multi-wire touch screen. A membrane generally impermeable to fluids may overlay the display screen 122 so the caregiver can press on images of keys or buttons on the underlying screen with wet gloves, dry gloves or without gloves to trigger an input.

A memory 124 communicates with the processor 118 and stores code and data necessary for the processor 118 to perform the functions of the medical device 14. More specifically, the memory 124 stores multiple programs formed in accordance with the present disclosure for various functions of the medical device 14 including a graphical user interface program 126 with multiple subparts described in greater detail below.

Infusion and Infusion Devices

Infusion devices may be programmed to carry out various types of infusion sequences. Types of infusion sequences include continuous infusion, intermittent infusion, multi-step infusion, inter-channel sequencing infusion, "infinite" (i.e., uninterrupted) flow infusion, and total parenteral nutrition (TPN) infusion.

Continuous infusion refers to infusion that occurs at a defined infusion rate until the infusion device has delivered the Volume-to-be-Infused (VTBI). The infusion device may then perform a user-selectable action which may include, e.g., keeping the vein open (KVO), continuing the infusion rate, or stopping the infusion.

Intermittent infusion refers to infusion that occurs until the infusion device has delivered the VTBI, at which point the infusion device performs a user-selectable action and then resumes the infusion until infusion device has again delivered the VTBI. The infusion device may repeat an intermittent infusion a user-specified number of times.

Multi-step infusion is similar to intermittent infusion as multi-step infusion involves multiple sequential infusions of the same medication. In contrast to intermittent infusion, however, subsequent infusions in multi-step infusion may be configured to deliver the medication at a different dose, rate, VTBI, or duration. A subsequent infusion in a multi-step infusion may also be configured such that a different action is performed when the subsequent infusion is complete.

Inter-channel sequencing infusion refers to infusion that involves multiple sequential infusions that can be delivered via different lines and thus from different sources containing different substances. The infusion devices used for inter-channel sequencing may include a single-channel large volume pump (LVP), a dual-channel LVP, a syringe pump, or a patient-controlled analgesia (PCA) pump. Inter-channel sequencing infusion may also be performed using multiple infusion devices in which a channel of a first infusion device infuses a first substance and a channel of a second infusion device infuses a second substance. Inter-channel sequencing infusion that uses multiple infusion devices may be referred to as inter-device infusion.

"Infinite" flow infusion refers to infusion that utilizes two delivery lines on a single cassette channel wherein the infusion device automatically switches to the other line when the current line completes its infusion such that there is no interruption in the delivery. A caregiver may then replace the depleted delivery source without having to stop or otherwise interrupt the current infusion.

Total parenteral nutrition infusion refers to infusion that delivers nutrition intravenously according to a pre-defined protocol.

As noted above, multi-channel infusion devices may include both a primary and a secondary line. A caregiver may program the infusion device to deliver a primary infusion via either the primary or the secondary line. When an infusion device has been programmed with a primary infusion, the caregiver may program the other line (either the primary line or the secondary line) to deliver a secondary infusion. The secondary infusion may be a concurrent infusion or a piggyback infusion. A concurrent infusion refers to simultaneous delivery from two delivery sources and independent infusion rates. Piggyback infusion refers to infusion that will stop infusion on one line, complete infusion on another line, and then restart infusion on the stopped line.

As also noted above a medical device can be a single channel infusion pump, a multi-channel infusion pump, or some combination thereof.

Figure 3:
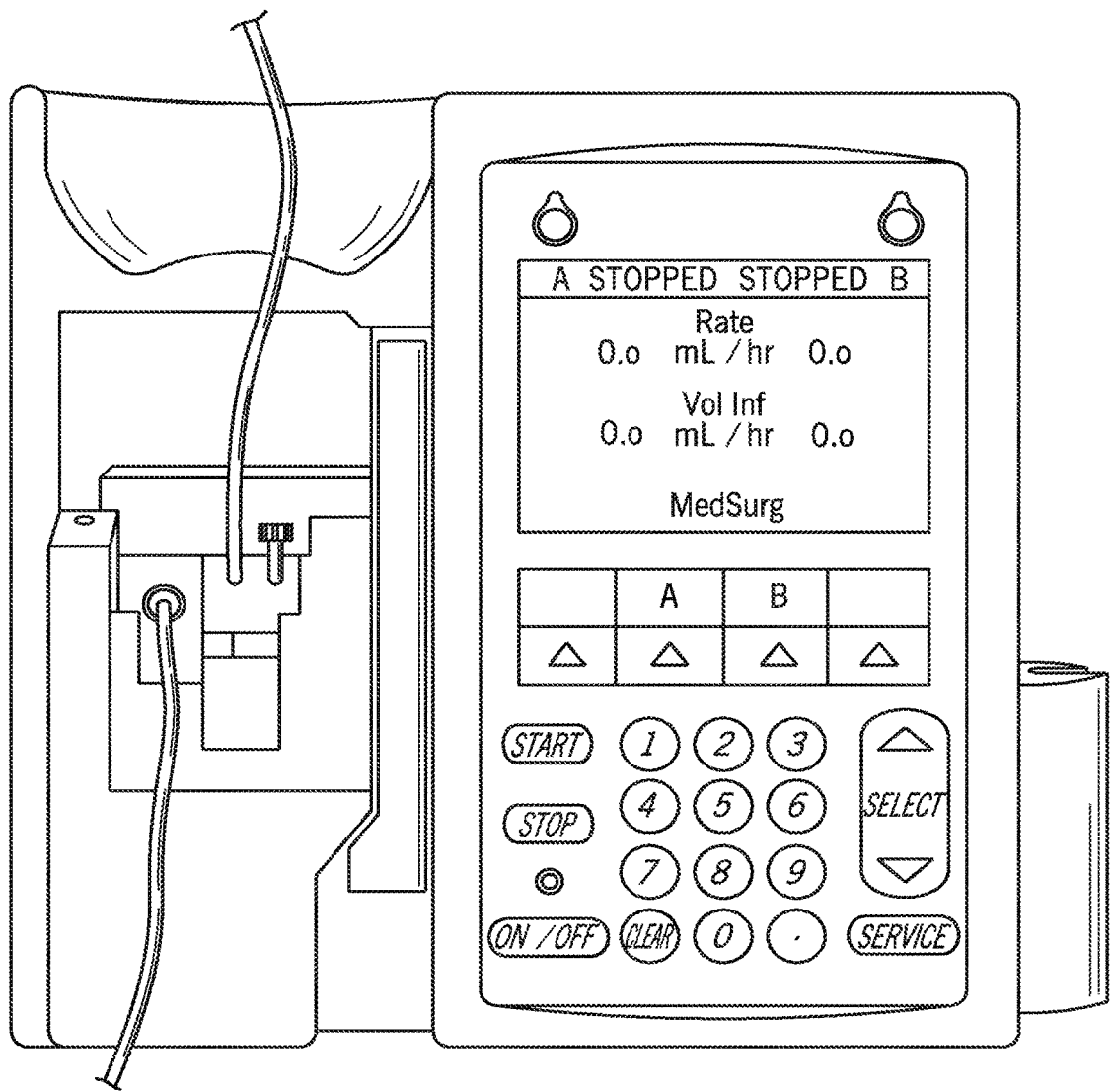
FIG. 3 depicts an example of a single-channel infusion device.

FIG. 3 depicts an example of a medical device that is a single channel infusion device. The infusion device may include a display screen that may display error messages, error codes, and suggested actions. The infusion device may comprise a memory, a processor, a clock (real time or otherwise) and other components. The memory may store computer-executable instructions the processor may execute to cause the infusion device to perform one or more steps described in further detail below.

Figure 4:
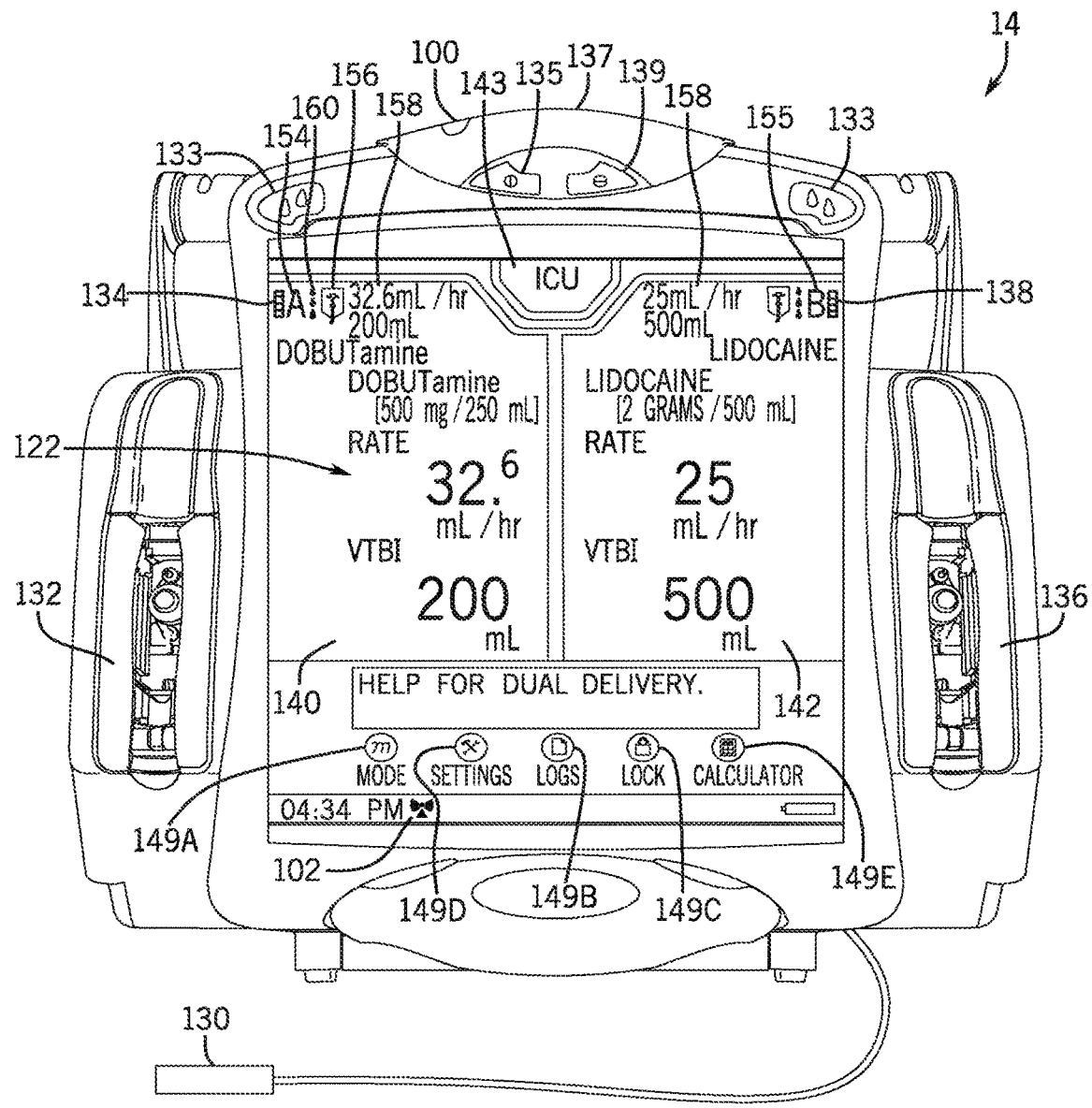
FIG. 4 depicts an example of a multi-channel infusion device.

FIG. 4 depicts an example of a medical device 14 that is a multi-channel infusion device having a first channel 132 with first channel machine-readable label 134 and a second channel 136 with a second channel machine-readable label 138. A user of the medical device 14 operates the machine-readable input device 130 to select a channel from one or more channels 132 and 136, by scanning in the associated machine-readable label 134 or 138.

The caregiver selects the desired channel 132 or 136 by using the machine-readable input device 130 to scan a factory or hospital programmed, unique, machine-readable label 134 or 138 that is electronically generated and presented on the screen 122, which may be juxtapositioned near the respective channel 132 or 136. Alternatively, the machine-readable labels 134 and 138 are physically affixed to the medical device 14, which may be on or juxtapositioned near the channel 132 and 136, respectively. Since the machine-readable labels 134 and 138 are generated and/or can be stored in memory 124 by the medical device 14, the medical device 14 can associate the machine-readable labels 134 and 138 to the channels 132 or 136. The medical device 14 then allows the caregiver to program and activate the selected channel 132 or 136. The caregiver may also manually select the desired channel by touching an appropriate folder tab on the touch screen. The folder tabs are labeled and/or physically arranged on the screen so as to be proximate to the corresponding channel 132 or 136.

In a further aspect of the wireless embodiment, the medical devices can periodically broadcast a unique wireless device/channel IP address and/or a self-generated unique machine-readable label (for example, a barcode) 134 or 138 that can also be presented on the screen 122. Alternatively, the machine-readable labels 134 and 138 are physically affixed to or posted on the medical device 14. Each medical device may correlate such broadcasted or posted device/channel IP addresses and/or barcodes with a particular patient, who is also identified by a unique machine readable label (not shown) or patient IP address. The caregiver associates the desired pump(s) or channel(s) 132, 136 with the patient by using the machine-readable input device 130 to scan the unique machine-readable labels 134, 138 and the patient's machine readable label. This causes the appropriate pump processor(s) 118 to associate the appropriate pump channel(s) 132, 136 with the patient. Then the pumps or channels can associate communicate, and coordinate with each other wirelessly.

The medical device 14 includes a split touch screen 122 having a first channel screen portion 140 associated with first channel 132 and a second channel screen portion 142 associated with the second channel 136. Each channel screen portion 140 and 142 presents a subset of the delivery information regarding the respective channels 132 or 136, including without limitation therapeutic agent name, concentration, dose rate, VTBI, and alarm information, in a font size that it is easily readable by a caregiver from a distance such as, for example, from approximately fifteen to twenty feet (4.6-6.2 meters) away. This is what is referred to as a "far view" delivery screen. The far view delivery screens display subsets of the information found on the relevant "near view" delivery screens. The near view delivery screen displays drug name, concentration, dose rate, time remaining, VTBI, volume remaining, and alarm name for the highest priority alarm if in an alarm state. The near view delivery screen will switch to the far view delivery screen after a defined period of time that is predetermined by the manufacturer, configurable by the facility via the drug library, and/or set by the caregiver at the device, for example after 20 seconds.

Upon a caregiver touching one of the tabs "A" or "B" or anywhere on the channel screen portions 140 or 142 of the far view delivery screen, a "near view" delivery screen is presented on the screen 122. The channel screen portion 140 or 142 selected or corresponding to the tab selected expands in area but the size of at least some of the text therein is shrunk.

The shrinkage of one of the channel screen portions 140 and 142 and enlargement of its counterpart provides additional space for one or more data display or data entry fields to be placed on screen 122. As discussed below, data displays or data entry fields are placed on screen 122 in space previously occupied by portions of the channel screen portion 140 or 142. This reallocation of space on screen 122 permits the caregiver to enter inputs more easily since the data entry field can be large, preferably at least as large or, more preferably, larger in area than the original channel screen portions 140 and 142 were in the delivery screen mode. Additionally, the reallocation of space on screen 122 provides greater space for presenting information on the channel being adjusted or monitored.

Referring again to FIG. 4, the medical device 14 includes dedicated or fixed tactile infuser buttons, and images of buttons on the LCD-touch screen 122. The fixed tactile buttons 133, 135, 137, and 139 provide the following functions: LOAD/EJECT button 133—opens and closes the cassette carriage; ON/OFF button 135—turns power on and off; ALARM SILENCE button 137—silences a silenceable alarm for a specified period of time, for example two minutes; and EMERGENCY STOP button 139—stops all channels.

The LCD color touch screen 122 allows the caregiver to access and use on-screen button images, for example 3D button images, and data entry fields. The touch screen 122 uses a membrane over the LCD display so a single keypress does not cause significant infusion pole movement nor is it mistaken for a double keypress. The touch screen also accommodates a keypress whether the caregiver is wearing wet gloves, dry gloves, or no gloves.

Figure 5:
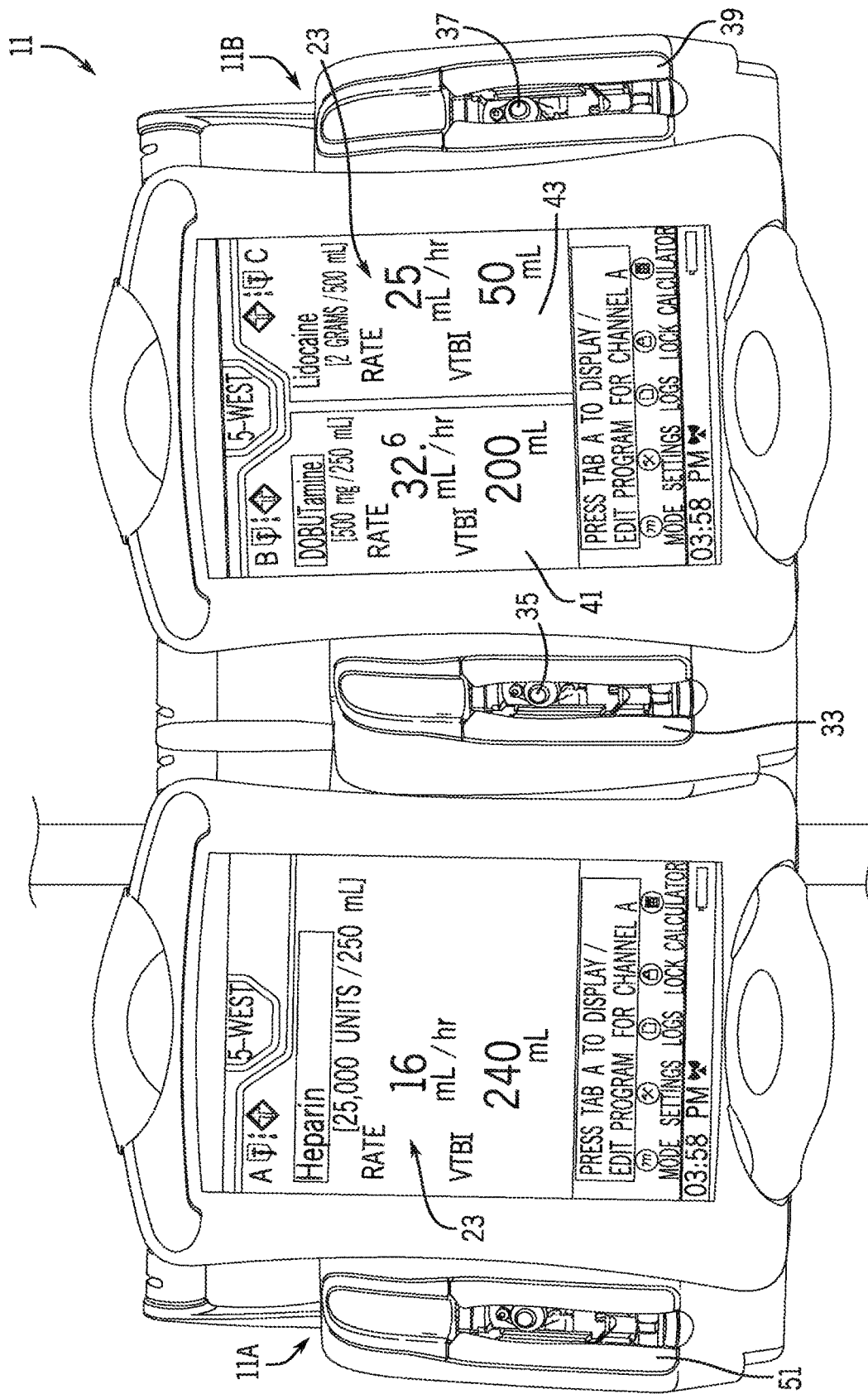
FIG. 5 depicts an example of a medical device including two infusion devices that are associated with one another.

FIG. 5 depicts an example medical device 11 that includes a single-channel infusion device 11A and a multi-channel infusion device 11B. The single-channel infusion device 11A has a single channel 51 (i.e., an "A" channel). The multi-channel infusion device has a first channel 33 (i.e., a "B" channel) and a second channel 39 (i.e., a "C" channel). The single channel infusion device 11A and the multi-channel infusion device 11B are physically and communicatively connected to each other for programming and operation in a coordinated manner. In one example, the single channel infusion device 11A and the multi-channel infusion device 11B are detachably coupled together. Although FIG. 5 illustrates a single channel medical device 11A associated with a multi-channel medical device 11B, is it noted that this is for illustrative purposes only, and other various combinations of various types of infusion devices may be made without departing from the present disclosure. Additionally, while the infusion devices 11A and 11B are shown as being physically associated, it is contemplated that they may alternatively be wirelessly associated.

The infusion device 11B of the medical device 11 has a first channel 33 and a second channel 39. A first tube set may be operably coupled to the first channel 33 to deliver a fluid from the first channel 33 and a second tube set may be operably coupled to the second channel 39 to deliver a fluid from the second channel 39. Each of the channels 33, 39 includes a respective pumping mechanism 35, 37 for acting upon a tube set to pump fluid. Various pumping mechanisms may be utilized without detracting from the present invention. The tube set may be made of soft, kink-resistant medical grade tubing and may include a medicinal dispensing pump cassette that is acted upon by the pumping mechanism. The first channel 33 may also include a first channel machine-readable label (134 in FIG. 4) and the second channel 39 may also include a second channel machine-readable label (138 in FIG. 4). A user of the medical device 10 may operate a machine-readable input device (130 in FIG. 4) to select a channel from one or more channels 33 and 39, by scanning in the associated machine-readable label.

The user may select the desired channel 33 or 39 by using the machine-readable input device to scan a factory or hospital programmed, unique, machine-readable label that is electronically generated and presented on the screen 23, which may be juxtapositioned near the respective channel 33 or 39. Alternatively, the machine-readable labels may be physically affixed to the medical device 11, which may be on or juxtapositioned near the channel 33 and 39 respectively. Since the machine-readable labels are generated and/or can be stored in memory by the infusion device 11B, the infusion device 11B can associate the machine-readable labels to the channels 33 or 39. The infusion device 11B then allows the user to program and activate the selected channel 33 or 39. The user may also manually select the desired channel by touching an appropriate folder tab on the touch screen. The folder tabs are labeled and/or physically arranged on the screen so as to be proximate to the corresponding channel 33 or 39. That is, the "B" tab is juxtapositioned near or adjacent to the "B" channel 33 and the "C" tab is juxtapositioned near or adjacent to the "C" channel 39.

A graphical user interface program may reallocate the screen 23 for one of the infusion devices 11A or 11B of the medical device 11. The infusion device 11B includes a split touch screen 23 having a first channel screen portion 41 associated with first channel 33 and a second channel screen portion 43 associated with the second channel 39. Each channel screen portion 41 and 43 presents a subset of the delivery information regarding the respective channels 33 or 39, including without limitation therapeutic agent name, concentration, dose rate, VTBI, and alarm information, in a font size of at least twenty-eight points so that it is easily readable by a user from approximately fifteen to twenty feet (4.6-6.2 meters) away. This is what is referred to as a "far view" delivery screen.

When a user touches one of the tabs "B" or "C," or any part of the channel screen portions 41 or 43 of the far view delivery screen, a "near view" delivery screen is presented on the screen 23. The channel screen portion 41 or 43 selected or corresponding to the tab selected expands in area but the size of at least some of its text is reduced. The font size for rate and VTBI information on the near view delivery screen is substantially less than twenty-eight points. The other channel screen portion 41 or 43 (if present) is reduced in size, hidden or moved to the background to limit its space on the screen 23. Preferably, if the "B" tab of the first channel screen portion 41 is selected, the "C" tab of the second channel screen portion 43 remains exposed, but is grayed or colored differently to indicate it is not the channel of interest. Thus, the second channel screen portion 43 becomes smaller than the first channel screen portion 41, as the first channel screen portion 41 is currently being viewed and adjusted by the user and is therefore of primary concern. The second or C channel can be selected in a similar manner, whereupon the first channel portion 41 of the screen 23 will become smaller and the second channel portion 43 will become larger. Since the screens for the respective channels are substantially identical, except for the position of their tabs, features shown in the drawings and described below relative to the B channel also apply to the C channel, and vice versa.

As described above, the memory stores multiple programs formed in accordance with the present invention, including an infuser program that allows for inter-channel sequencing infusions. Inter-channel sequencing infusions allows for the sequential delivery of separate substances from two or more channels. In particular, the infuser program can be programmed by a caregiver to sequence dispensation of substances between channels such that a patient can receive substances from two or more channels without having to reprogram the infusion device.

Figure 6:
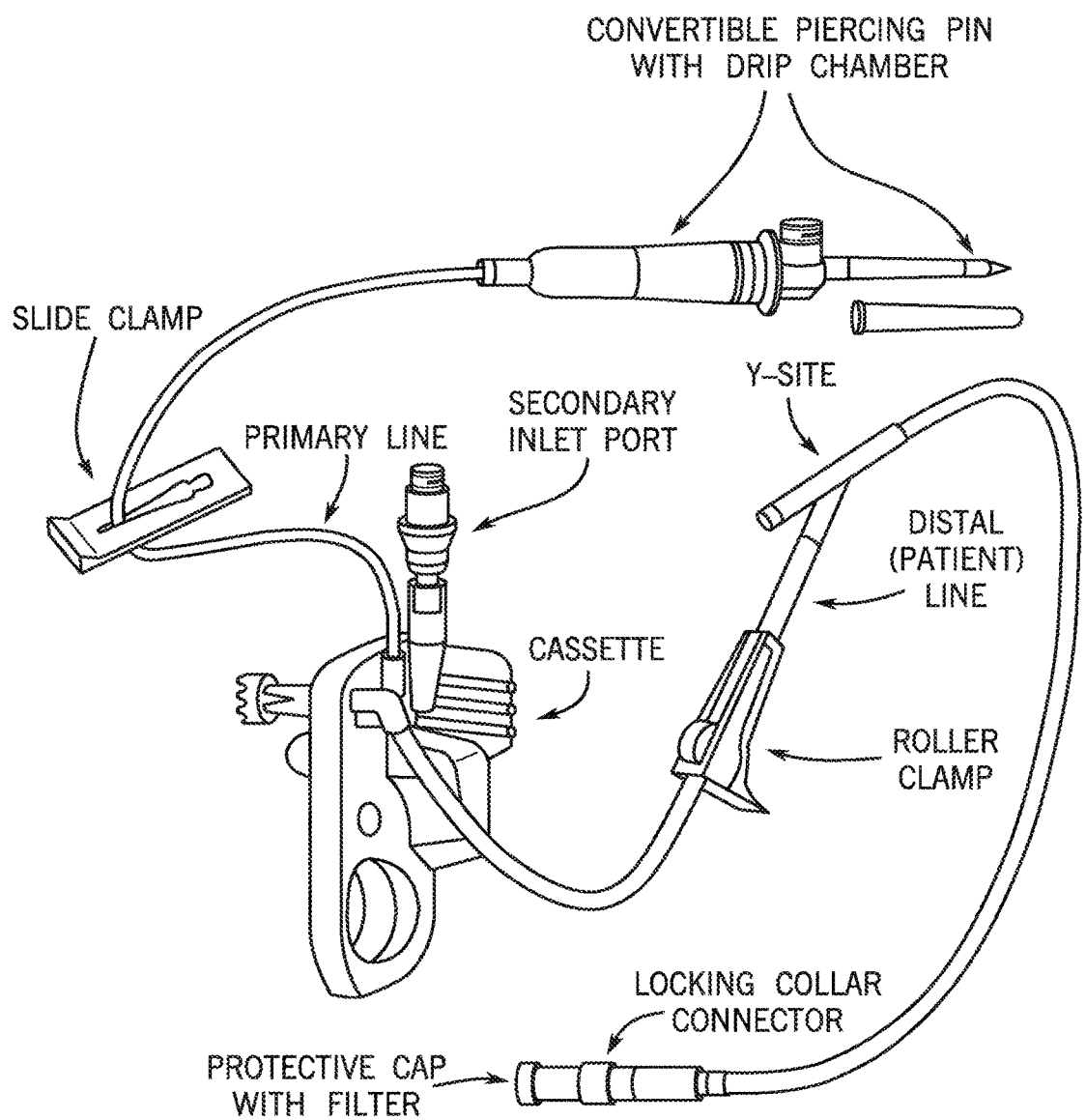
FIG. 6 depicts an example of a cassette kit for an infusion device.

FIG. 6 depicts an example of a cassette kit that may be used in a single-channel or multi-channel infusion device. As seen in FIG. 6, the cassette kit includes a cassette connected to a convertible piercing pin with drip chamber via a primary line along which a slide clamp may be positioned. The cassette is also connected to a patient line that includes a Y-site connector along its length and a protective cap with filter at one end. A roller clamp may also be positioned along the length of the patient line. The cassette in FIG. 6 also includes a secondary inlet port at which a secondary line may be connected.

The cassette in FIG. 6 may advantageously allow two deliver two infusions using the same infusion channel from delivery sources respectively connected to each of its two input ports. The cassette may route the substance received from the delivery sources at the input ports to the output line connected to the patient. As described in further detail below, the use of this type of cassette advantageously presents new opportunities for configuring infusions at an infusion device.

Dynamic Infusion Programming

As noted above, aspects of the disclosure are directed toward advanced infusion features that allow a caregiver to dynamically configure the parameters of a current ongoing infusion of add steps to a current ongoing infusion.

Figure 7:
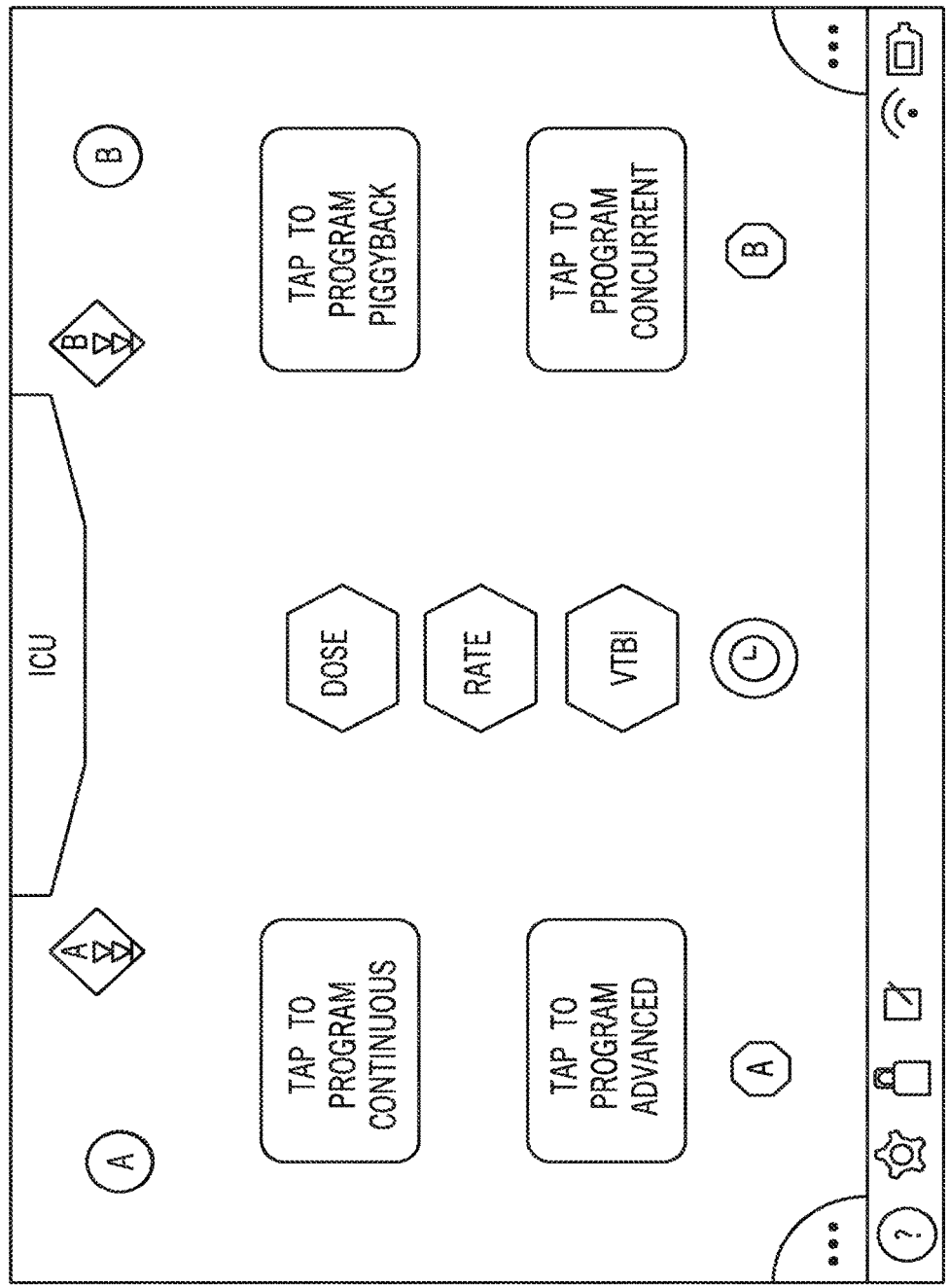
FIG. 7 depicts an example user interface of an infusion device having multiple lines.

FIG. 7 depicts an example user interface of an infusion device having multiple lines, in this case a primary line (Line A) and a secondary line (Line B). As seen in FIG. 7, the interface includes input elements for selecting a type of infusion to program for the primary line, in this case a continuous infusion or an advanced infusion. Advanced infusions may include, e.g., an intermittent infusion, a multi-step infusion, an inter-channel sequencing infusion, an "infinite" infusion, and a TPN infusion. The interface also includes input elements for selecting a type of infusion to program for the secondary line, in this case a concurrent infusion or a piggyback infusion.

Figure 8:
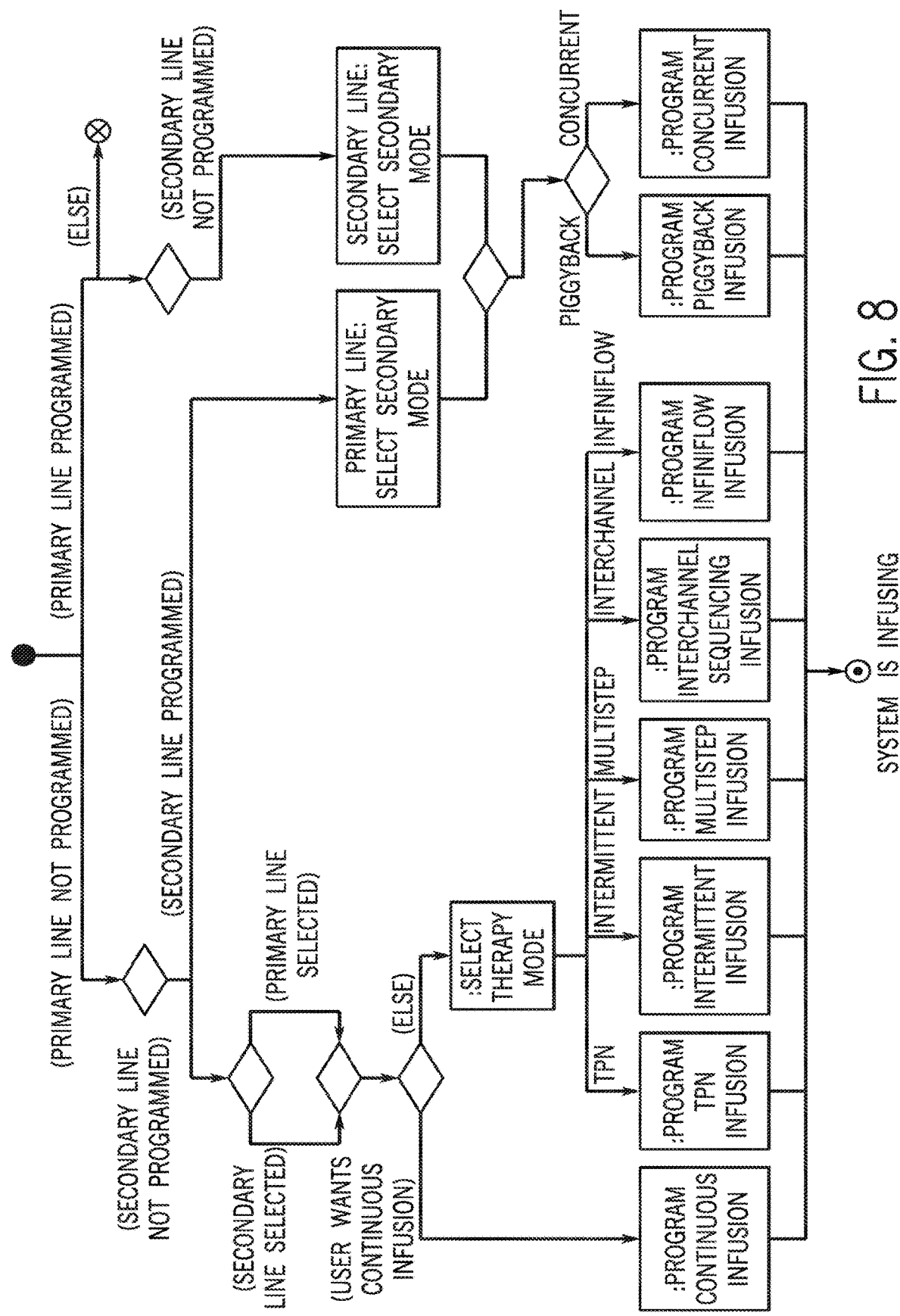
FIG. 8 depicts a flowchart of example method steps for programming an infusion to be delivered by an infusion device having multiple lines.

FIG. 8 depicts a flowchart of example method steps for programming an infusion to be delivered by an infusion device having multiple lines. As seen in FIG. 8, if the primary line and the secondary line have not yet been programmed, the caregiver may select either the primary line or the secondary line to program for the primary infusion. For the primary infusion, the caregiver may select either a continuous infusion or an advanced infusion as noted above with reference to FIG. 7. If the caregiver selects to provide an advanced type of infusion, the caregiver may select the particular type of advance infusion desired (e.g., intermittent, multi-step, inter-channel sequencing, "infinite," or TPN). The caregiver may configure the parameters of the selected infusion type, and, once programmed, the infusion device may initiate the primary infusion.

If either the primary line or the secondary line is already programmed, the caregiver may select the non-programmed line for a secondary infusion. As seen in FIG. 8, if the primary line has been programmed for the primary infusion, then the caregiver may select the secondary line for the secondary infusion. If, however, the secondary line has been programmed for the primary infusion, the caregiver may select the primary line for the secondary infusion. As also seen in FIG. 8, the caregiver may select either a concurrent infusion or a piggyback infusion for the secondary infusion. The caregiver may likewise configure the parameters of the selected infusion type and, once programmed, the infusion device may initiate the secondary infusion.

Figure 9:
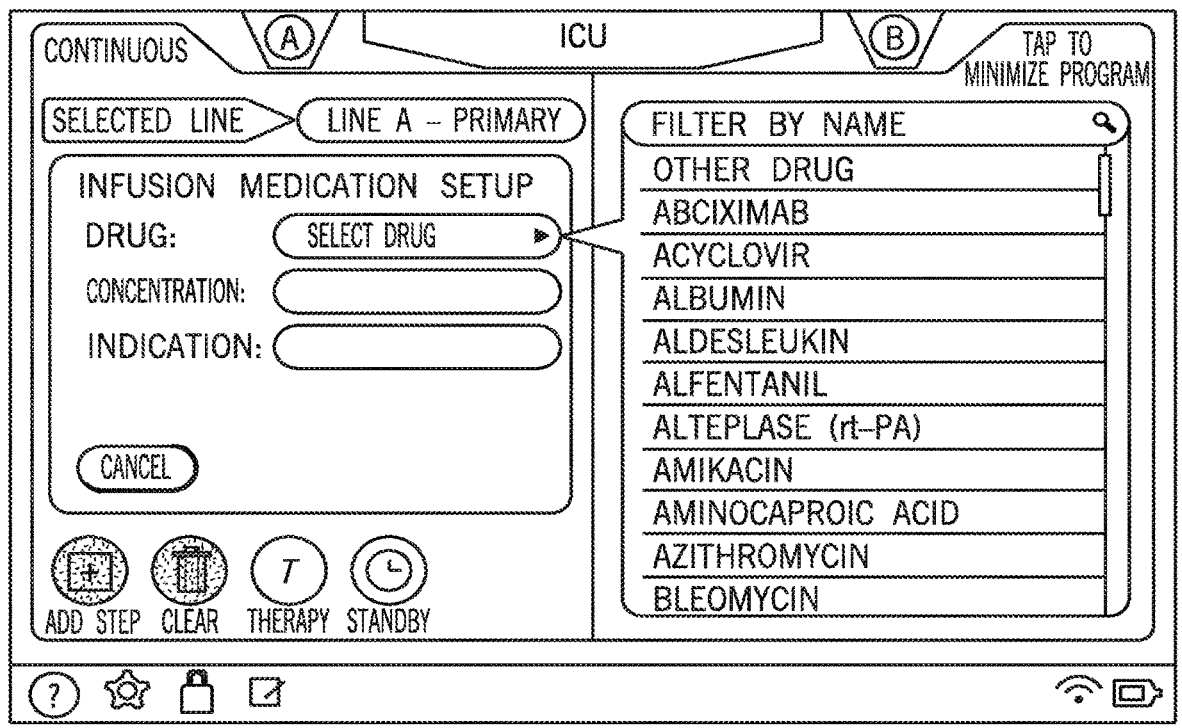
FIG. 9 depicts an example user interface at which the caregiver selects the substance to be delivered during the continuous infusion.
Figure 10:
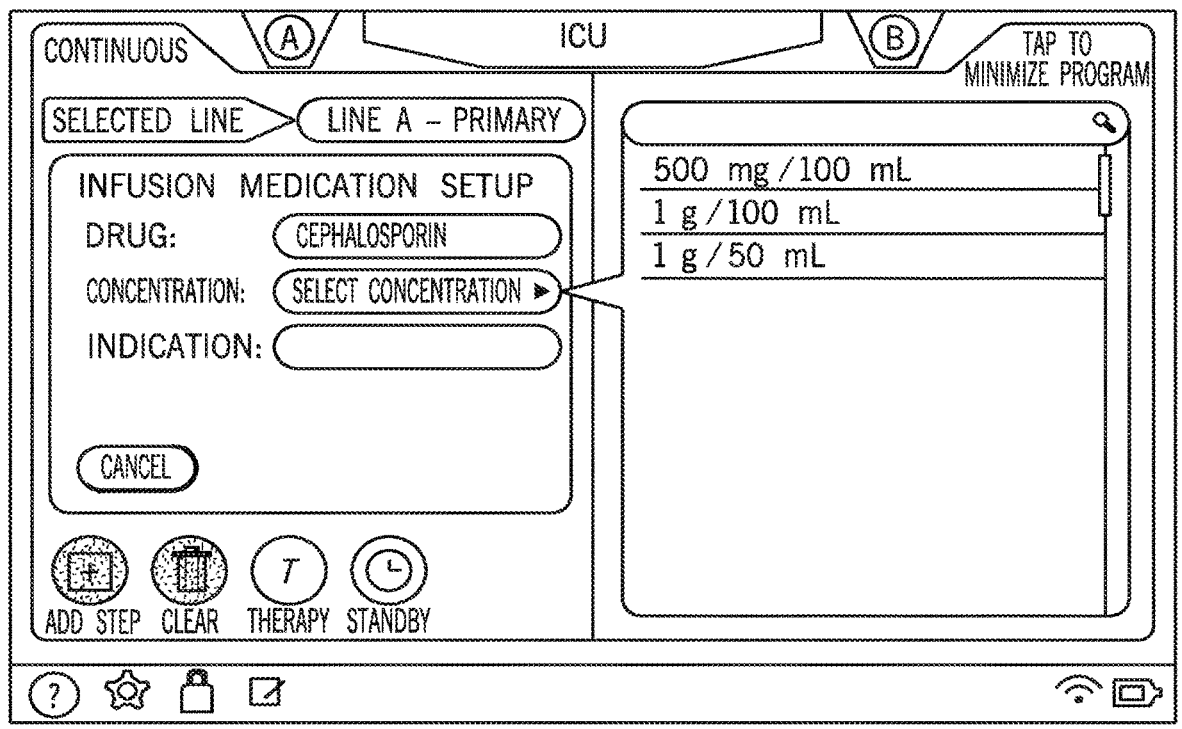
FIG. 10 depicts an example user interface at which the caregiver selects the concentration at which the selected substance should be delivered during the continuous infusion.
Figure 11:
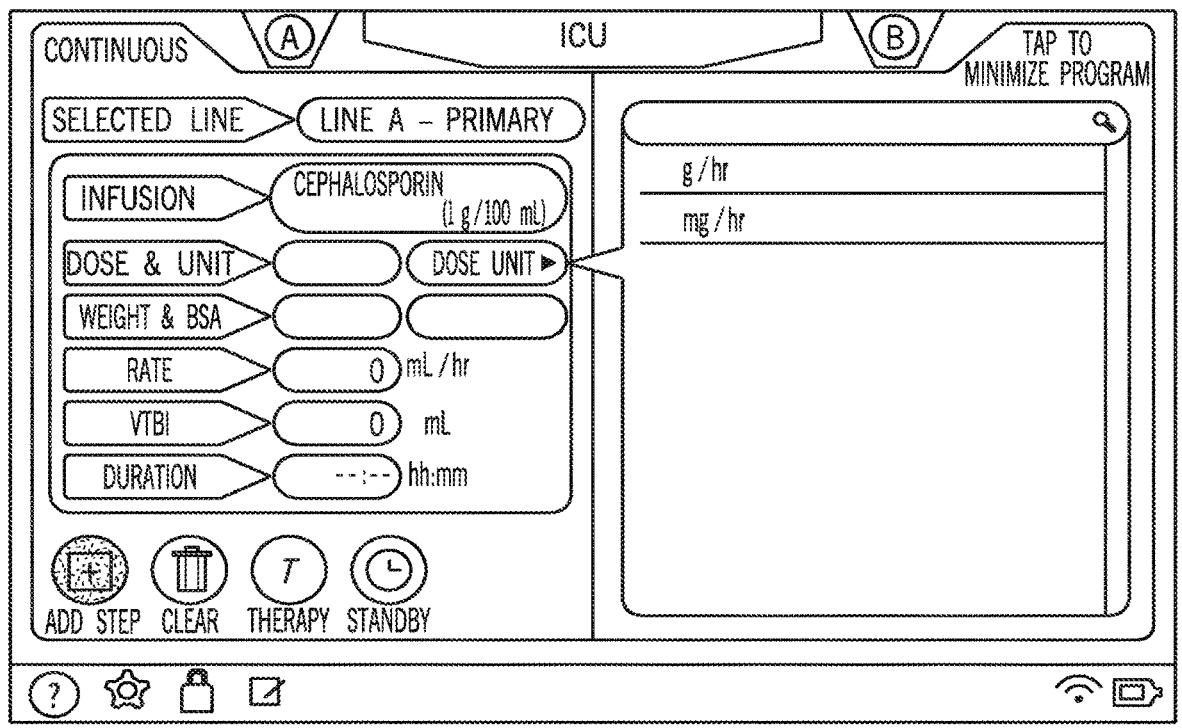
FIG. 11 depicts an example user interface at which the caregiver selects the dose and unit for the continuous infusion.
Figure 12:
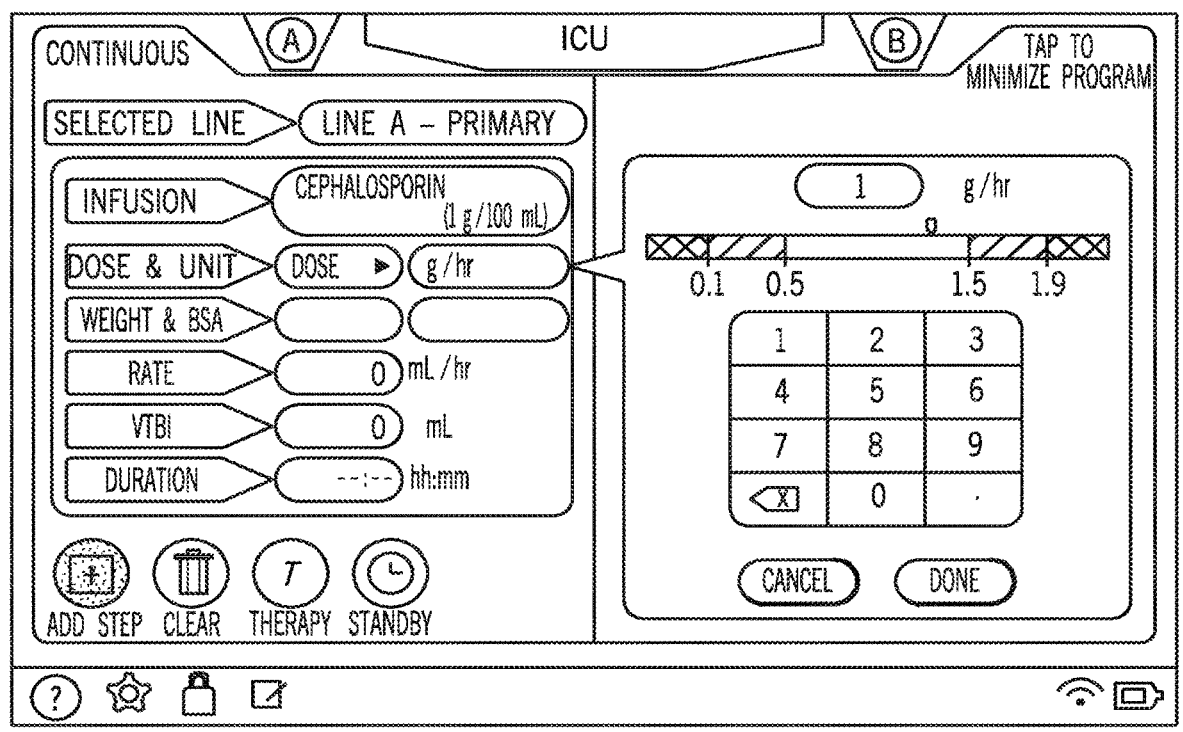
FIG. 12 depicts an example user interface at which the caregiver specifies the value of the dose per unit for the continuous infusion.

FIGS. 9-15 depict example user interfaces of an infusion device for configuring the parameters of a continuous infusion on the primary line (e.g., Line A). FIG. 9 depicts an example user interface at which the caregiver selects the substance to be delivered during the continuous infusion. The user interface includes a list of substances available for selection which is filterable by substance name. FIG. 10 depicts an example user interface at which the caregiver selects the concentration at which the selected substance should be delivered during the continuous infusion. The interface includes a list of concentrations available for selection. FIG. 11 depicts an example user interface at which the caregiver selects the dose and unit for the continuous infusion. This interface includes a list of doses per unit available for selection. FIG. 12 depicts an example user interface at which the caregiver specifies the value of the dose per unit for the continuous infusion. This interface includes input elements, in this case a keypad and a slider, at which the caregiver may specify the desired value for the dose per unit.

Figure 13:
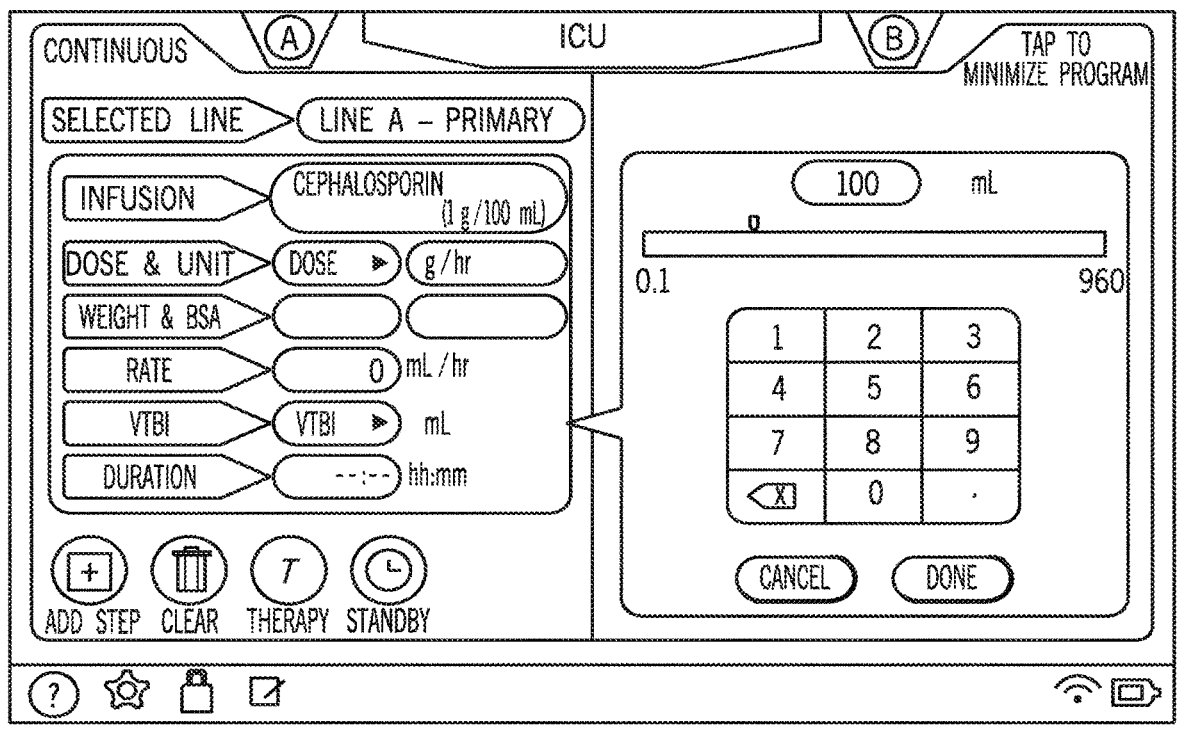
FIG. 13 depicts an example user interface where the caregiver has selected to specify a VTBI.

For a continuous infusion, the caregiver may specify a desired VTBI or a desired duration. If the caregiver specifies a VTBI, then the infusion rate and duration may be automatically calculated based on the selected concentration, dose per unit, and VTBI. If the caregiver specifies an infusion duration, then the VTBI and infusion rate may be automatically calculated based on the selected concentration, dose per unit and infusion duration. FIG. 13 depicts an example user interface where the caregiver has selected to specify a VTBI. This interface likewise includes input elements (e.g., a keypad and slider) at which the caregiver may specify the desired value for the VTBI. Similar input elements may be provided to specify a value for the infusion duration where the caregiver opts to specify the infusion duration rather than the VTBI. In some circumstances, the caregiver may skip certain configuration steps, e.g., where the delivery substance does not have a dose (e.g., saline).

Figure 14:
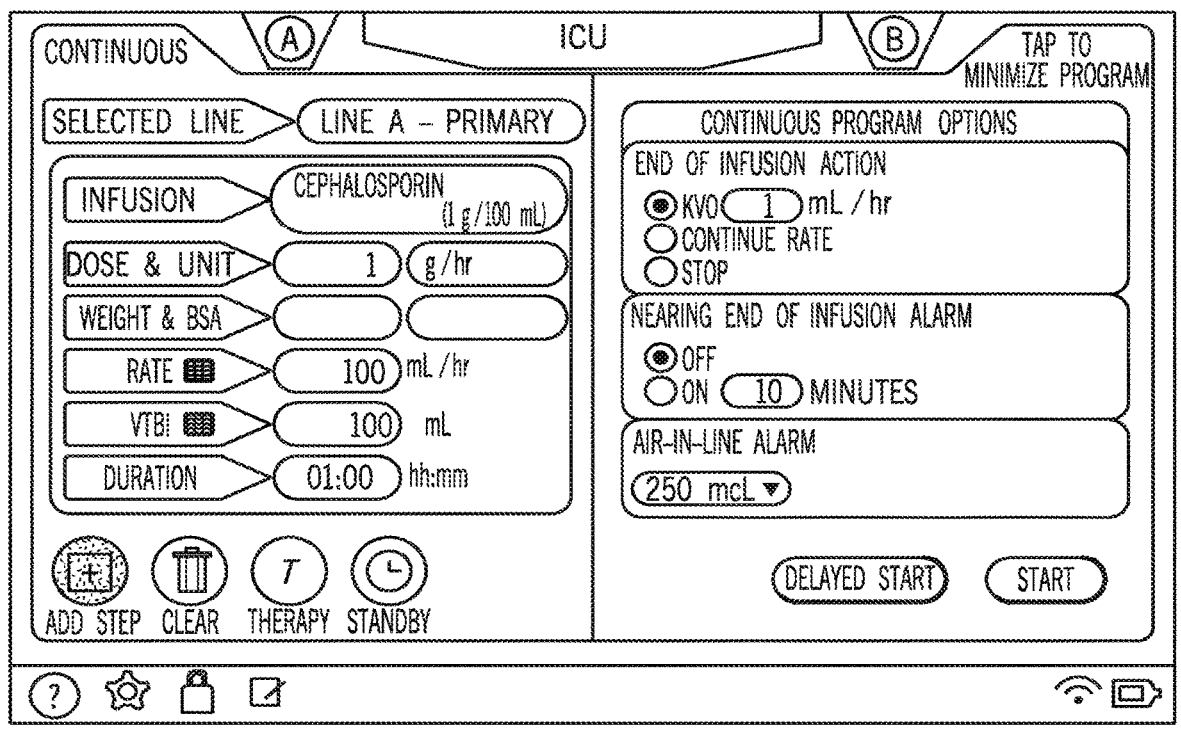
FIG. 14 depicts an example user interface at which the caregiver selects the action the infusion device should perform upon completing the continuous infusion.

FIG. 14 depicts an example user interface at which the caregiver selects the action the infusion device should perform upon completing the continuous infusion. This interface includes various actions available for selection including a KVO action, a continue rate action, and a stop action. The interface also includes input elements at which the caregiver may specify a KVO rate or a continue rate. This interface further includes input elements at which the caregiver may configure an alarm when the continuous infusion nears completion. The interface includes input elements at which the caregiver may toggle the alarm on and off and specify how soon the alarm should be provided prior to completing the continuous infusion. In addition, this interface includes an input element at which the caregiver may specify a threshold for an air-in-line alarm. Having configured the parameters of the continuous infusion, the caregiver may start the infusion by selecting a "START" button at the interface. The caregiver may also select to start the infusion after a specified delay by selecting a "DELAYED START" button at the interface.

Figure 15:
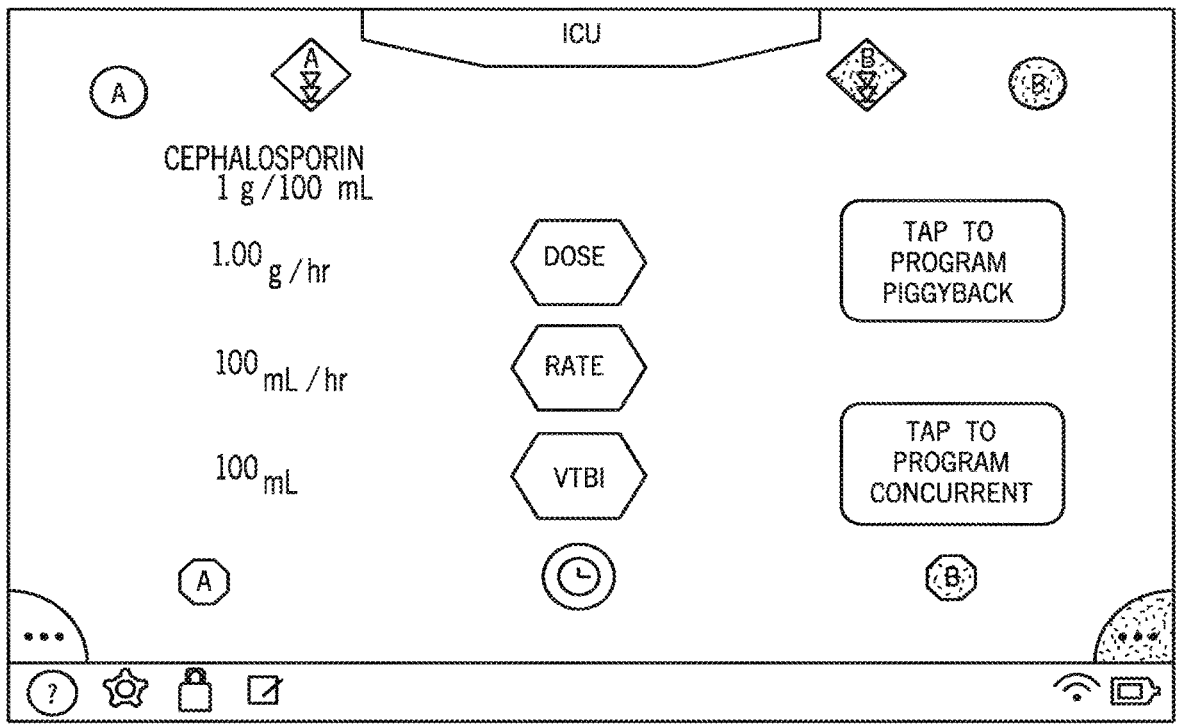
FIG. 15 depicts an example user interface that displays the parameters of the primary infusion currently being delivered by the infusion device.

Once the primary infusion has started, the infusion device may display the parameters of the current infusion. FIG. 15 depicts an example user interface that displays the parameters of the primary infusion currently being delivered by the infusion device. As seen in FIG. 15, the parameters displayed include the substance being delivered, the dose, the rate, and the VTBI. The infusion device may update the interface as the VTBI changes throughout the infusion (e.g., from 100 mL remaining to 97 mL remaining). The interface may also include the remaining duration of the current infusion.

Figure 16:
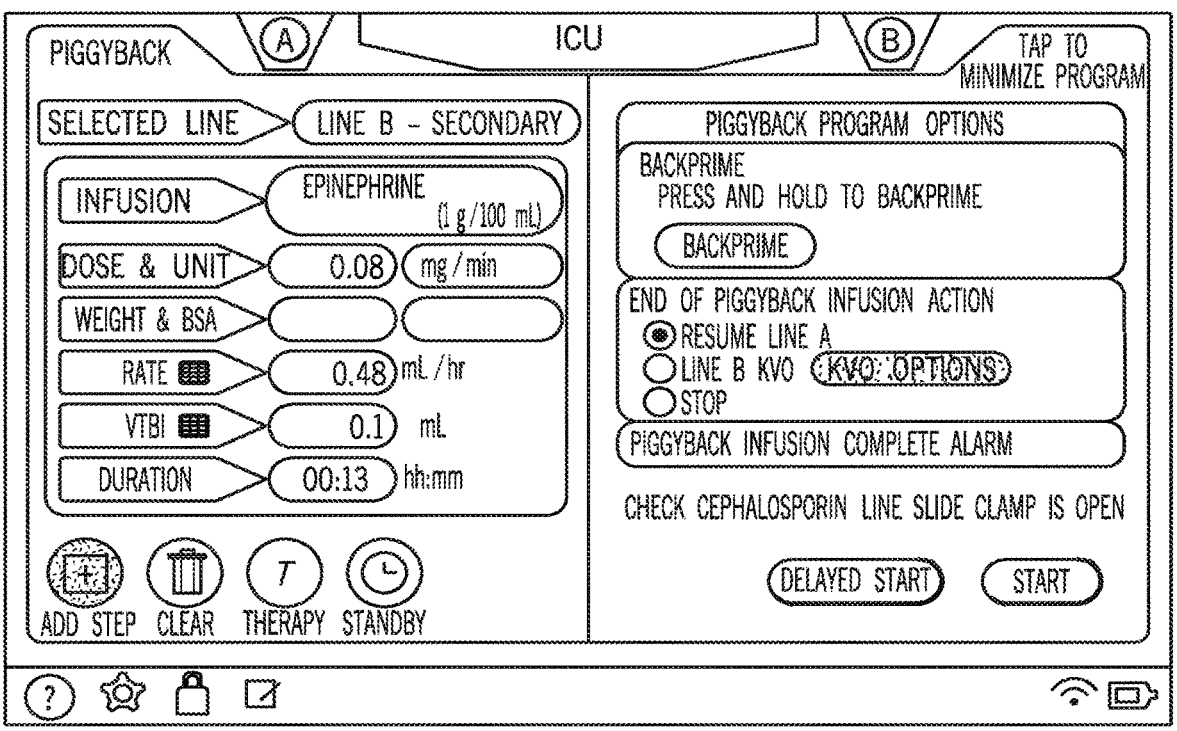
FIG. 16 depicts an example user interface at which the caregiver may specify the action to perform upon completion of a piggyback infusion.

During the primary infusion, the caregiver may select and program a secondary infusion to be delivered along with the primary infusion. As seen in FIG. 15, the caregiver may select a secondary infusion type for the secondary line, e.g., a concurrent infusion or a piggyback infusion. The caregiver may navigate through user interfaces similar to those depicted in FIGS. 9-13 to specify the substance, concentration, dose per unit and corresponding value, and VTBI or duration value. Having configured the parameters of the secondary infusion, the caregiver may similarly specify an action to perform upon completion of the secondary infusion. FIG. 16 depicts an example user interface at which the caregiver may specify the action to perform upon completion of a piggyback infusion. As seen in FIG. 16, the actions available for selection include resuming infusion at the primary line, a KVO action at the secondary line, and stopping infusion at the secondary line. As also seen in FIG. 16, this interface includes a button to backprime the primary line before starting infusion at the secondary line. The caregiver may then select a button at the interface to start the secondary infusion with or without delay.

Figure 17:
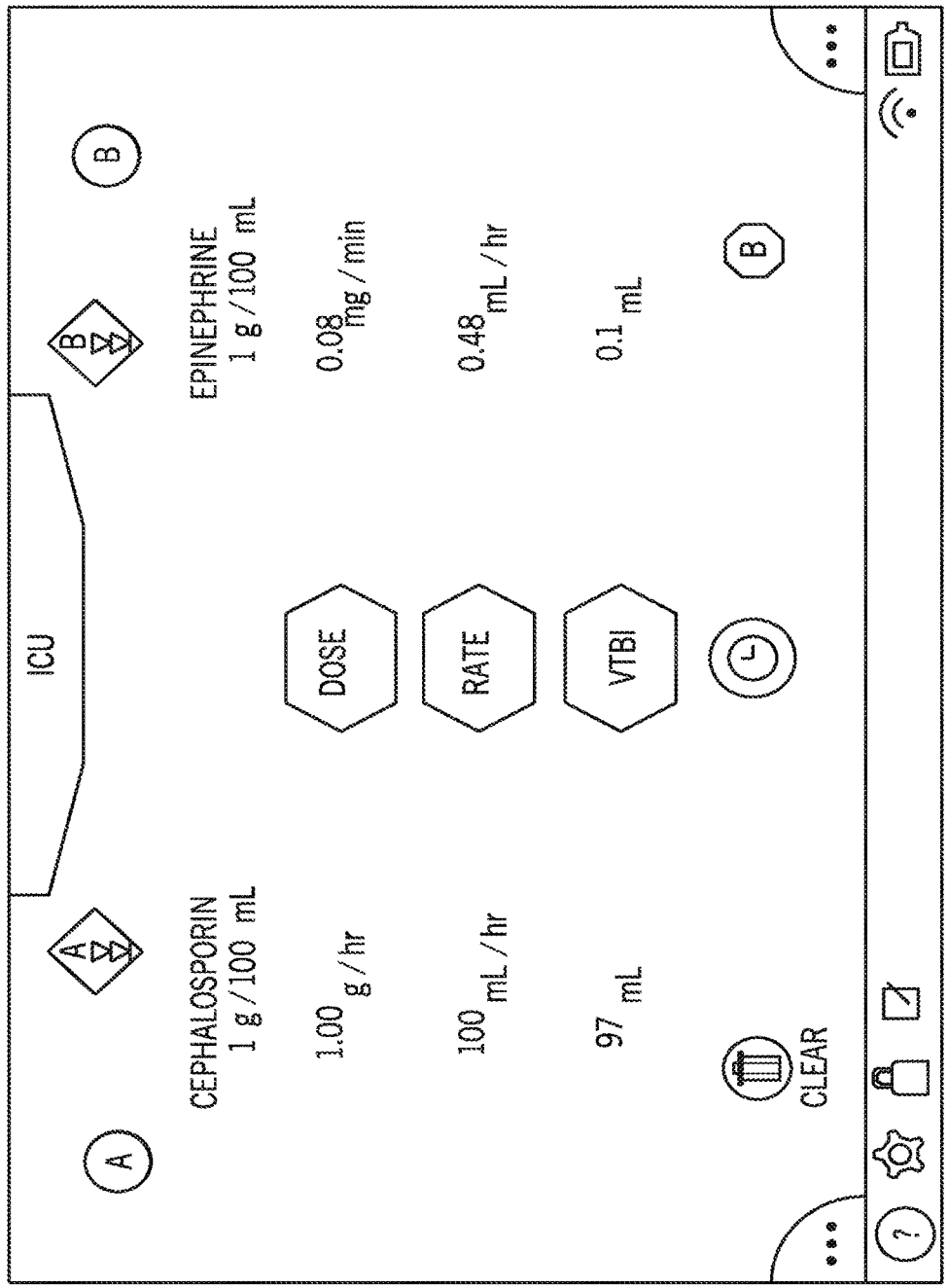
FIG. 17 depicts an example user interface that displays the parameters of both the primary and secondary infusions currently being delivered by the infusion device.

Once the secondary infusion has started, the infusion device may display the parameters of the current infusions. FIG. 17 depicts an example user interface that displays the parameters of both the primary and secondary infusions currently being delivered by the infusion device. This interface likewise displays the substances being delivered by the primary and secondary lines, as well as the respective concentrations, does, rates, and VTBI values.

In accordance with the screenshots above, FIGS. 18A-24 depict flowcharts for creating and configuring a continuous infusion procedure.

Figure 18A:
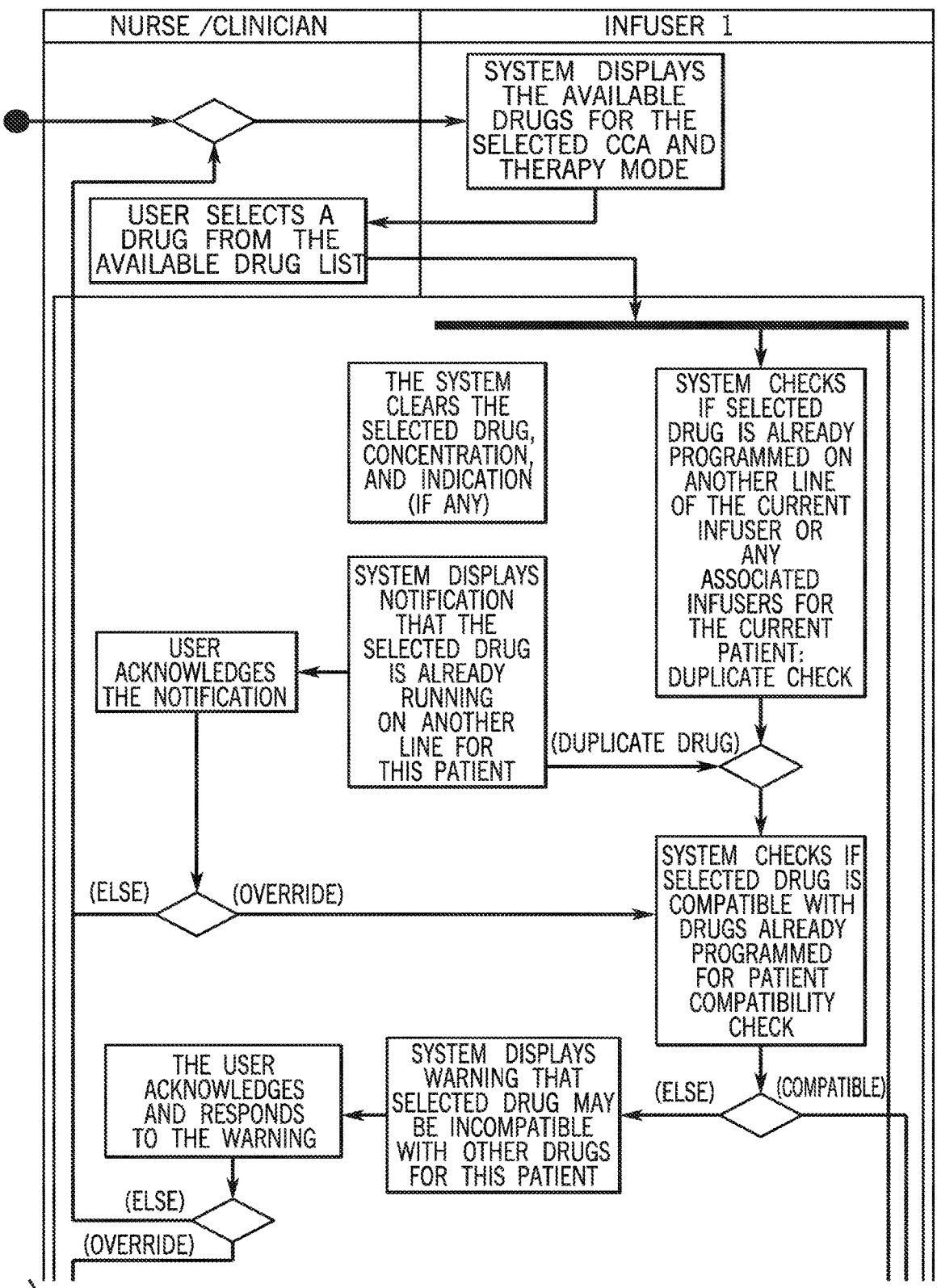
FIGS. 18A-18B depict a flowchart of example method steps for selecting a medication.
Figure 18B:
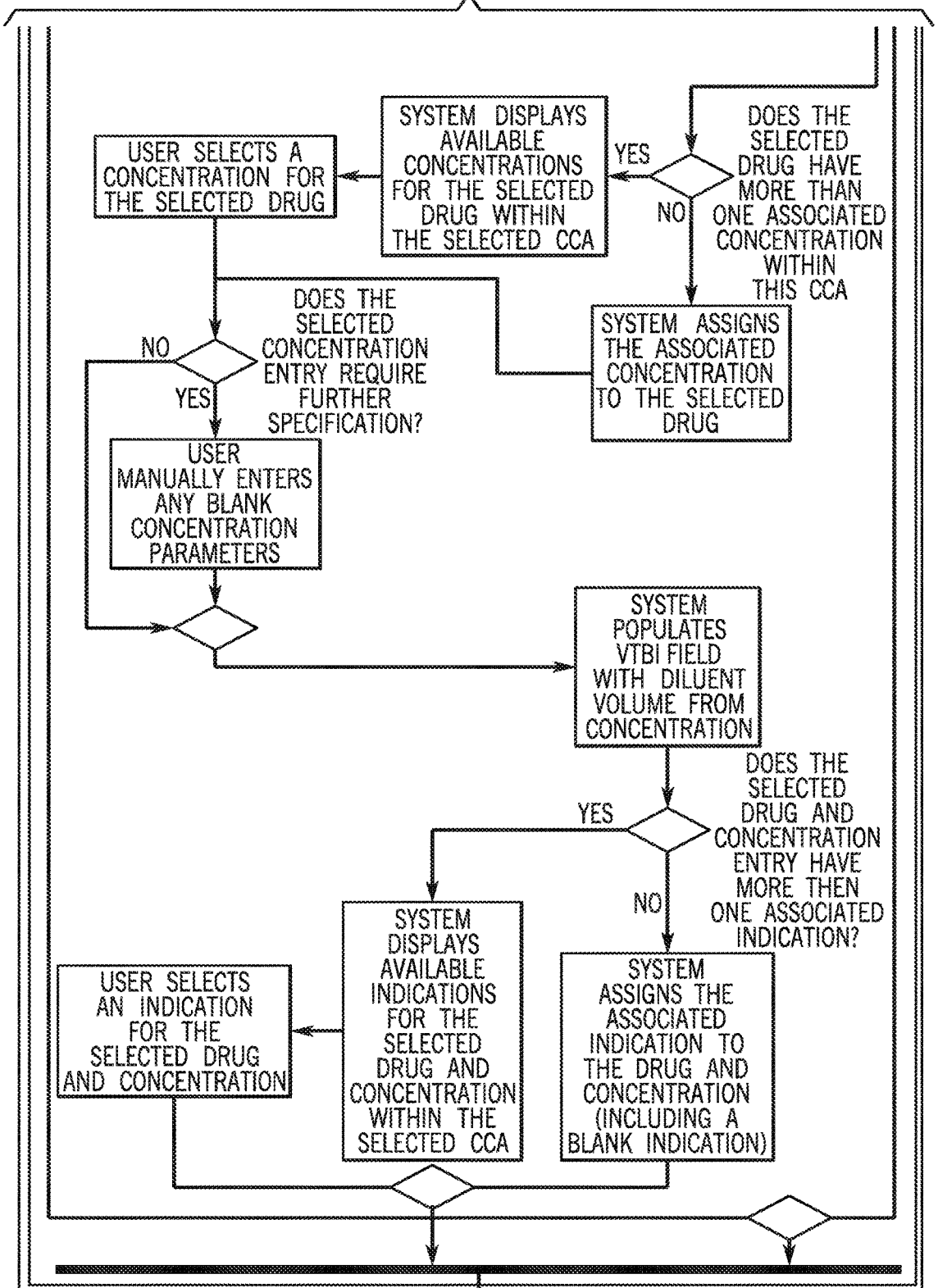

FIGS. 18A-18B depict a flowchart of example method steps for selecting a medication. As seen in FIGS. 18A-18B, the infusion device may be configured to display the infusion substances available for selection and initiate safety checks to determine whether the selected substance has already been selected for infusion at the current infusion device or another infusion device associated with the patient (i.e., a duplicate check) or if the selected substance is compatible with other substances selected for infusion (i.e., a compatibility check) at the current infusion device or other infusion devices associated with the patient. The infusion device may notify the caregiver of any potential duplicability or compatibility issues, which the caregiver may acknowledge and override if desired. As also seen in FIGS. 18A-18B, the caregiver may also select or specify, e.g., the desired concentration, VTBI, or indicators.

Figure 19A:
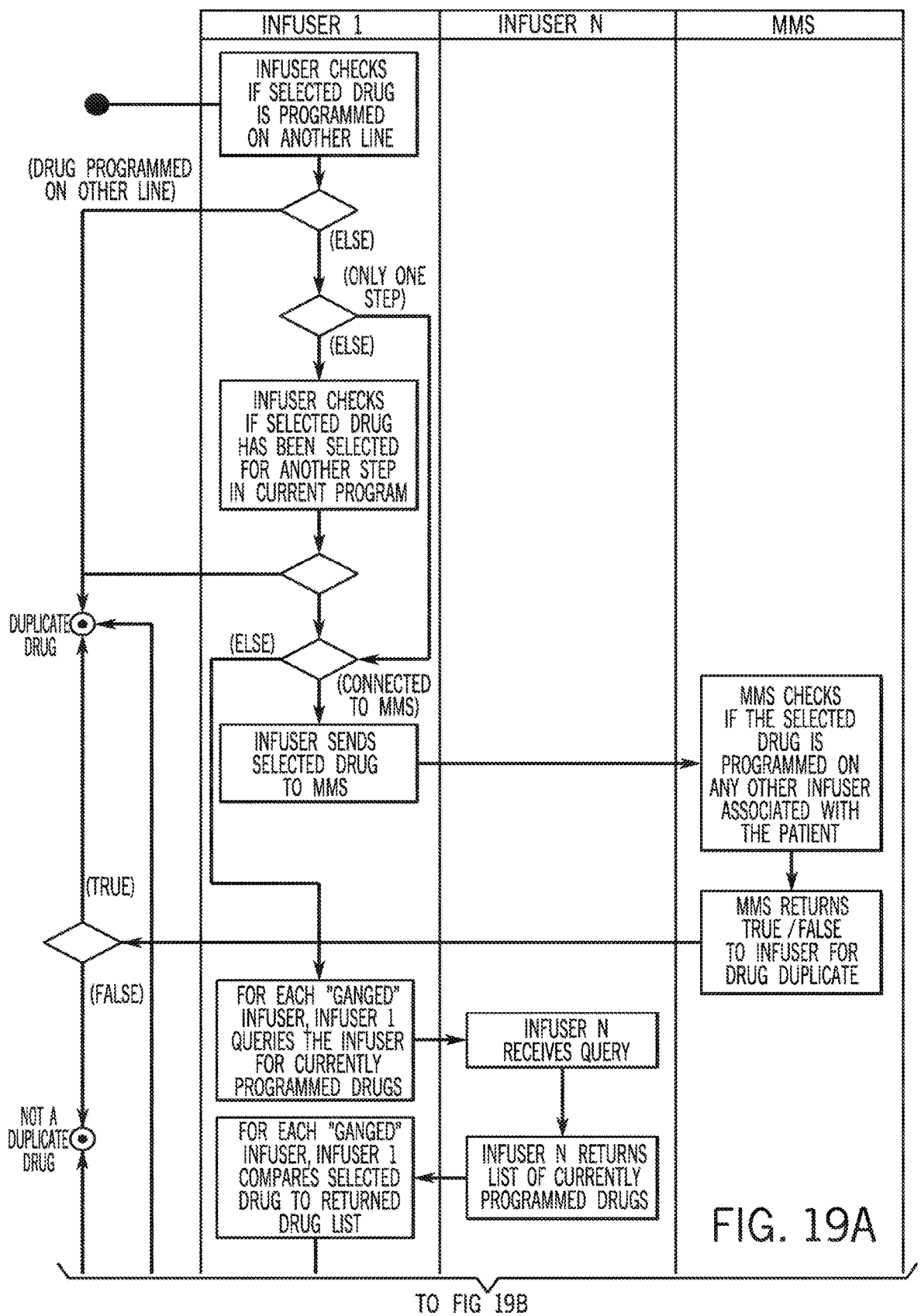
FIGS. 19A-19B depict a flowchart of example method steps for performing a safety check for duplicate infusion substances.
Figure 19B:
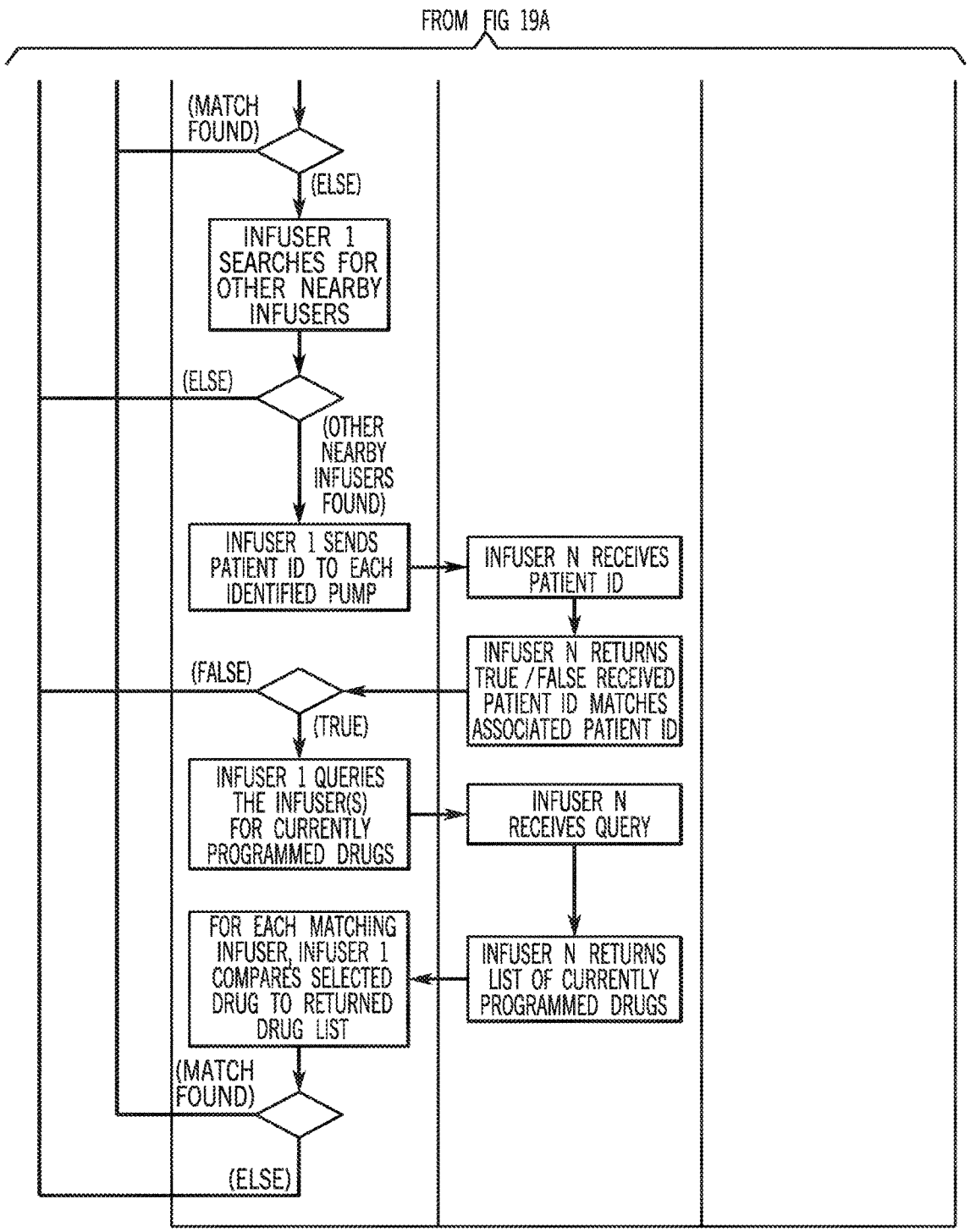

FIGS. 19A-19B depict a flowchart of example method steps for performing a safety check for duplicate infusion substances. As seen in FIGS. 19A-19B, the duplicate safety check may be performed with respect to multiple infusion devices associated with a patient (i.e., infusion device no. 1, infusion device no. 2, . . . , infusion device no. n). As described in further detail below, the infusion devices associated with the patient may be in signal communication with each other. In some implementations, the infusion devices may be set up in a master/slave configuration. As also seen in FIGS. 19A-19B, the infusion devices associated with a patient may also be in signal communication with a medication management system having medication safety software. Suitable medication safety software for the medication management system may include the Hospira MedNet™ Safety Software available from Hospira.

During the duplicate substance safety check, the infusion device may determine whether the selected substance has been selected for delivery on another line of the infusion device or during another step of the infusion sequence. The infusion device may also query the medication management system to determine whether the selected substance has been selected for delivery via another infusion device associated with the patient. Similarly, the infusion device may query the other infusion devices associated with the patient for a list of substances selected for delivery via those infusion devices. In response to the query, the other infusion devices may return a list of substances selected for delivery to the patient. The infusion device may then compare the selected substance to the respective lists of substances received from the other infusion devices. The infusion device may query other infusion devices it is connected to as a master or slave infusion device. The infusion device may also poll any nearby infusion devices and provide a unique identifier associated with the patient. If the polled infusion device indicates it is associated with the same patient (i.e., the patient identifiers match), then the infusion device may query from the polled computing device the list of substances selected for delivery via the polled computing device. If the infusion device determines that the selected substance matches a substance selected for delivery via another infusion device, then the infusion device may provide a notification or warning to the caregiver.

Figure 20A:
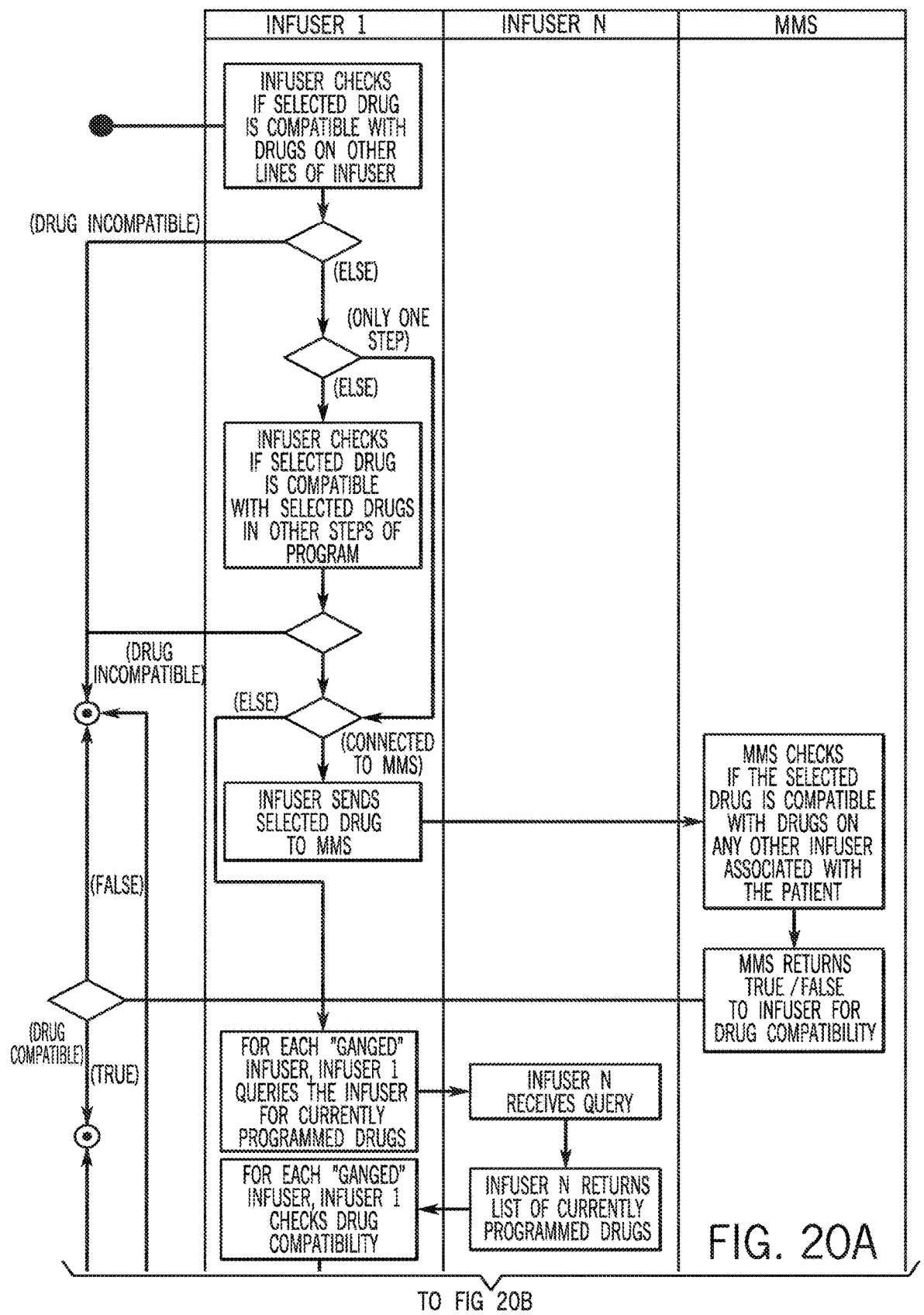
FIGS. 20A-20B depict a flowchart of example method steps for performing a safety check for compatible infusion substances.
Figure 20B:
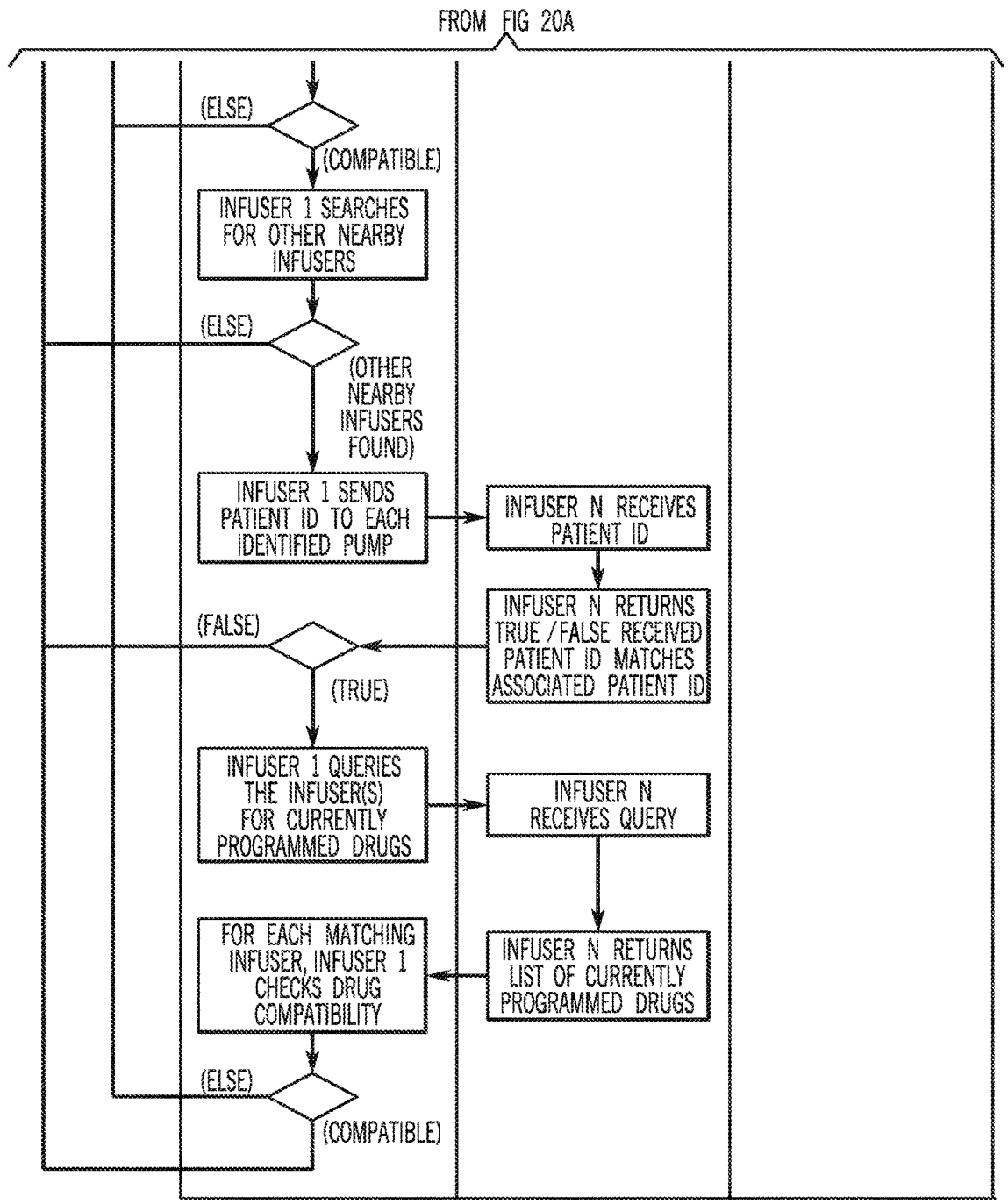

FIGS. 20A-20B depict a flowchart of example method steps for performing a safety check for compatible infusion substances. The compatibility safety check may be similar to the duplicate safety check discussed above. In particular, the compatibility safety check may likewise involve querying and polling multiple infusion devices associated with a patient and querying a medication management system to determine whether the selected substance is compatible with the selected substance. If the infusion device determines that the selected substance is (or is potentially) incompatible a substance selected to be delivered via another infusion device associated with the patient, then the infusion device may provide a notification or warning to the caregiver.

Figure 21A:
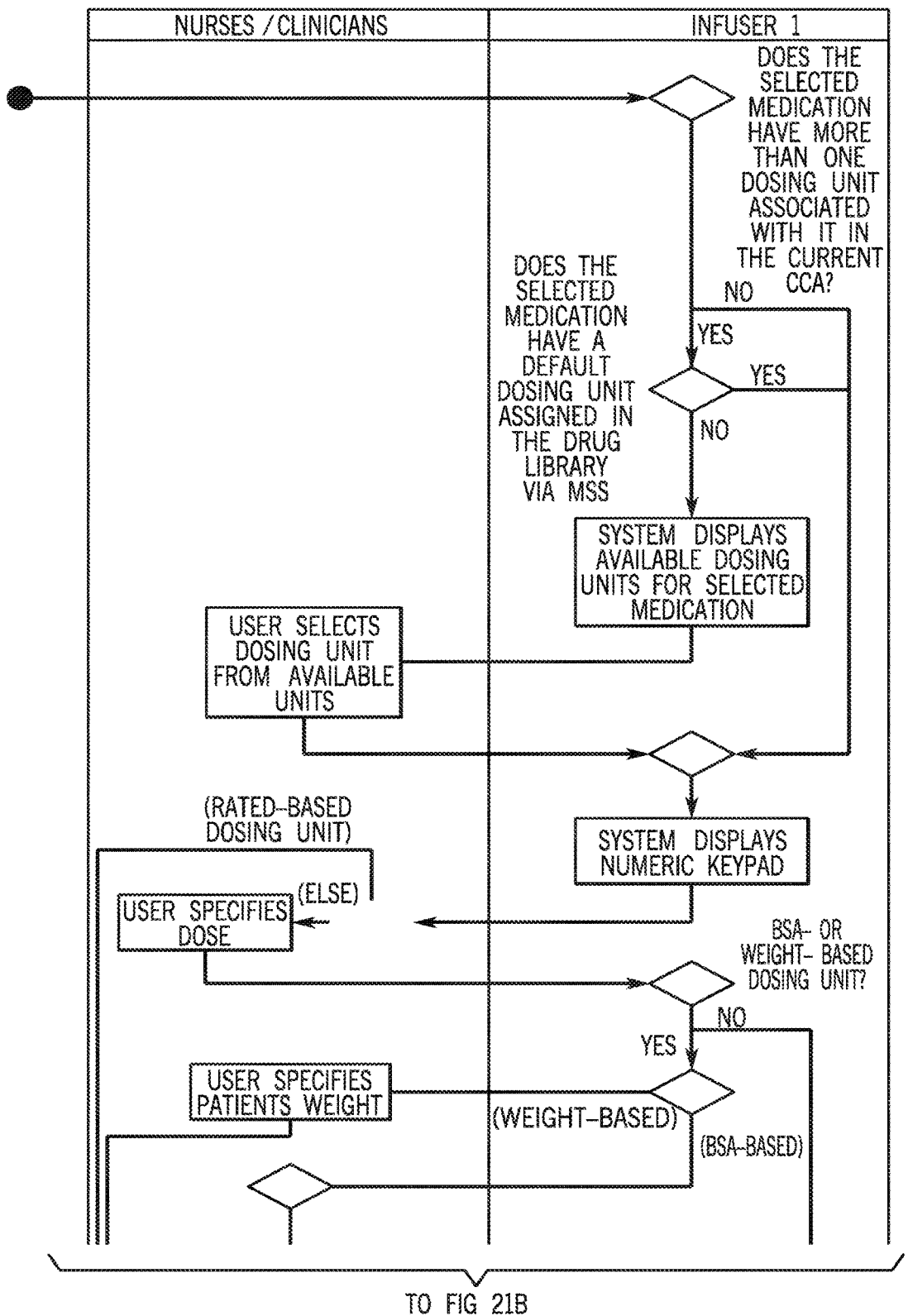
FIGS. 21A-21B depict a flowchart of example method steps for specifying a dose for the selected substance at the infusion device.
Figure 21B:
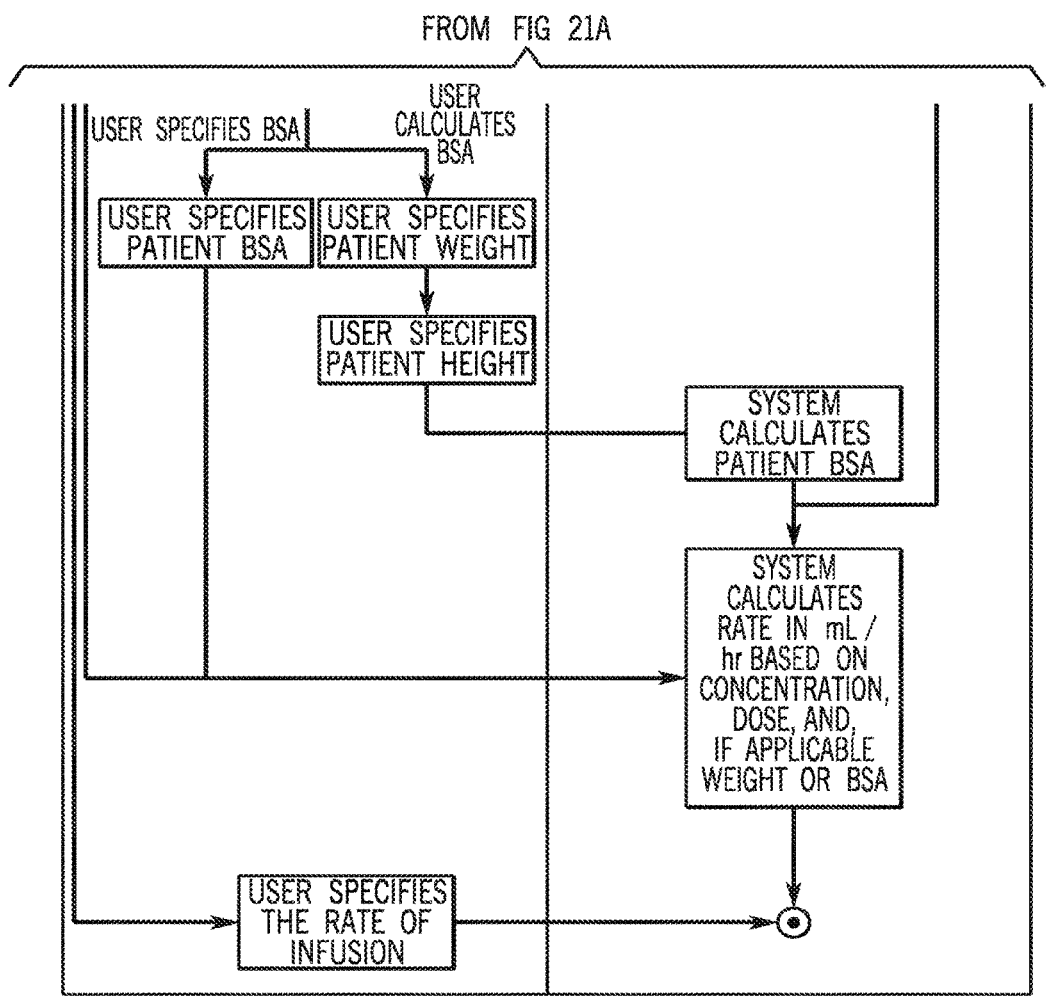

FIGS. 21A-21B depict a flowchart of example method steps for specifying a dose for the selected substance at the infusion device. As seen in FIGS. 21A-21B, the caregiver may select from a list of available dosing units for the selected substance displayed by the infusion device and specify a desired dose. The infusion device may include or be in signal communication with a library that specifies a default dose for the selected substance. The infusion device may allow the caregiver to specify a body surface area (BSA) dose (e.g., kilograms/kg or square meters/m2) or a patient weight-based dose. For a BSA dose, the infusion device may allow the caregiver to specify the patient weight and height and automatically calculate the patient BSA. The caregiver may also specify the rate of infusion, or the infusion device may be configured to calculate the rate (e.g., mL/hour) based on the concentration, dose, and weight or BSA.

Figure 22:
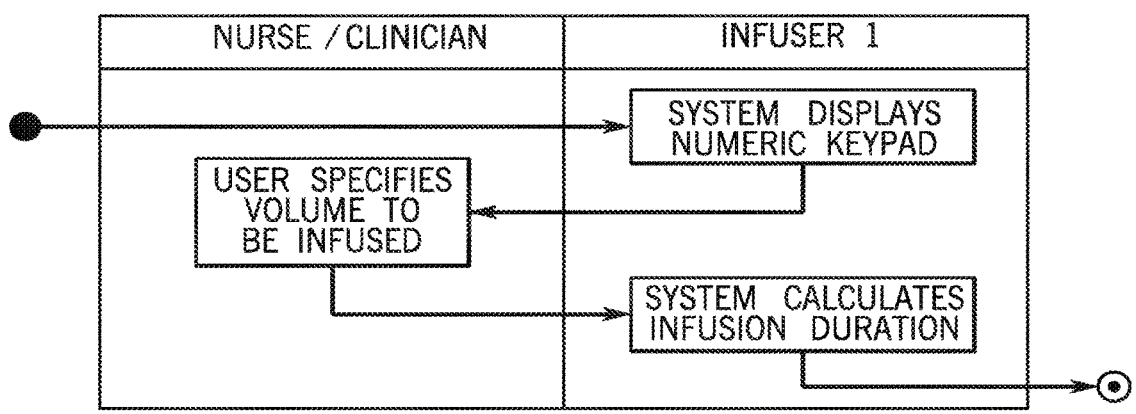
FIG. 22 depicts a flowchart of example method steps for specifying a VTBI.

FIG. 22 depicts a flowchart of example method steps for specifying a VTBI. As seen in FIG. 22, the infusion device may allow the user to specify the desired VTBI value and calculate an infusion duration based on that value.

Figure 23:
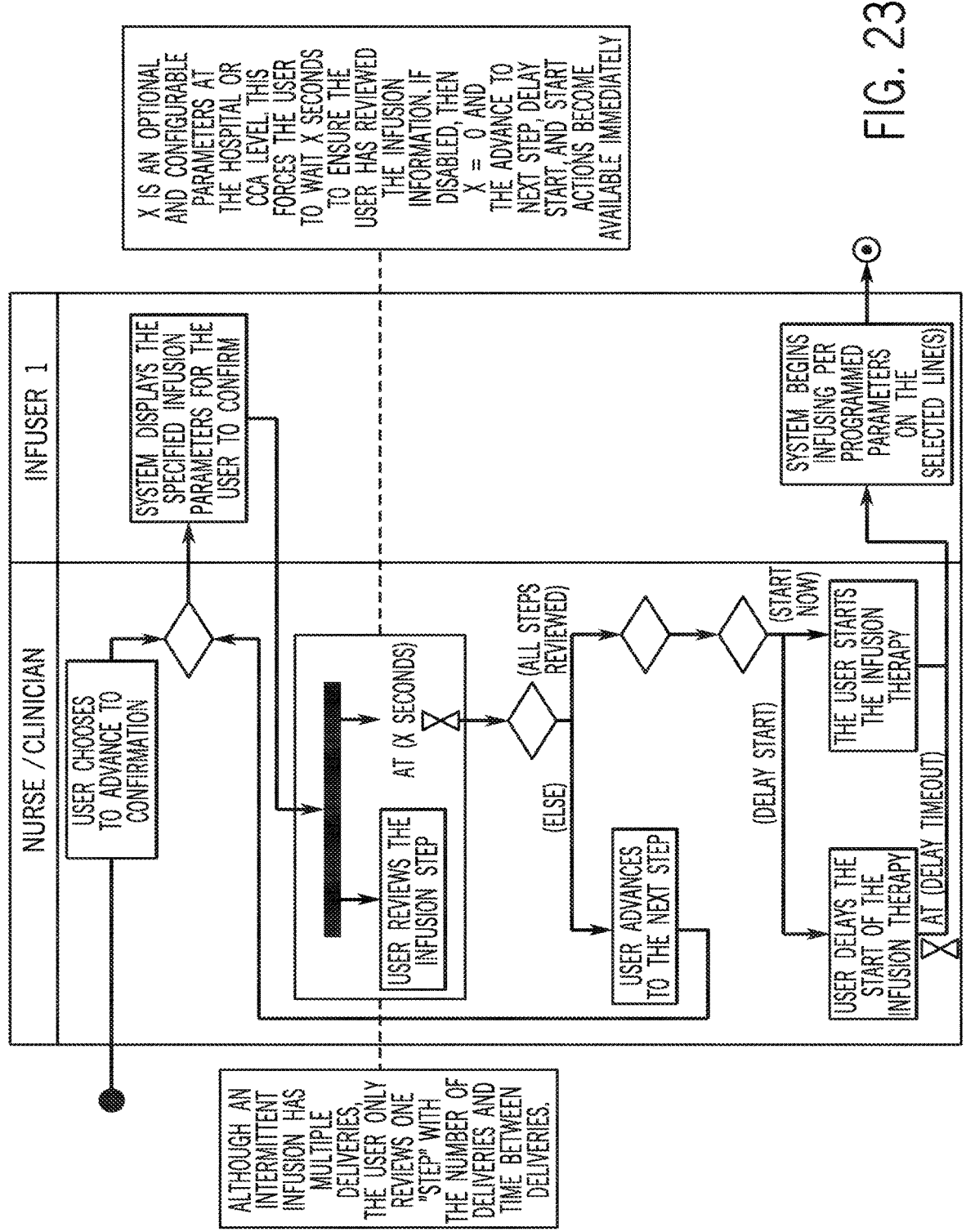
FIG. 23 depicts a flowchart of example method steps for confirming an infusion configured at the infusion device.

FIG. 23 depicts a flowchart of example method steps for confirming an infusion configured at the infusion device. As seen in FIG. 23, the infusion device displays the parameters selected for the infusion so that the caregiver may review them. The infusion device may also be configured to wait a user-selectable number of seconds before allowing the caregiver to confirm the parameters to ensure the caregiver has had enough time to review them. If the infusion involves multiple steps, the caregiver may advance to the next step in the infusion sequence to review the parameters configured for that step. If the infusion is an intermittent infusion, the infusion device may be configured to request confirmation of the parameters of only one of the intermittent infusion as well as the total number of intermittent infusions and the time between steps. Once all steps have been reviewed, the caregiver may start the infusion or initiate a delayed start for the infusion. At the infusion start time, the infusion device may begin the infusion sequence.

The infusion device described herein is also configured to allow a caregiver to add a step to a current ongoing continuous infusion thus converting the current continuous infusion into one of the advanced infusion types. In other words, the caregiver may convert a current continuous infusion into one of an intermittent, multi-step, inter-channel sequencing, or "infinite" flow infusion. The infusion device leverages the recognition that the advanced infusion types may be viewed as a series of continuous infusions delivered in sequence. In particular, an intermittent infusion may be recognized as a series of identical continuous infusions separated by a delay. A multi-step infusion may be recognized as a series of continuous infusions using the same substance at the same concentration and indication, but differing in dose, rate, or both dose and rate. An inter-channel sequencing infusion may be recognized as a series of continuous infusions delivered from different lines via different channels. An "infinite" flow infusion may be recognized as a series of continuous infusions delivered from different lines on the same channel.

Figure 24:
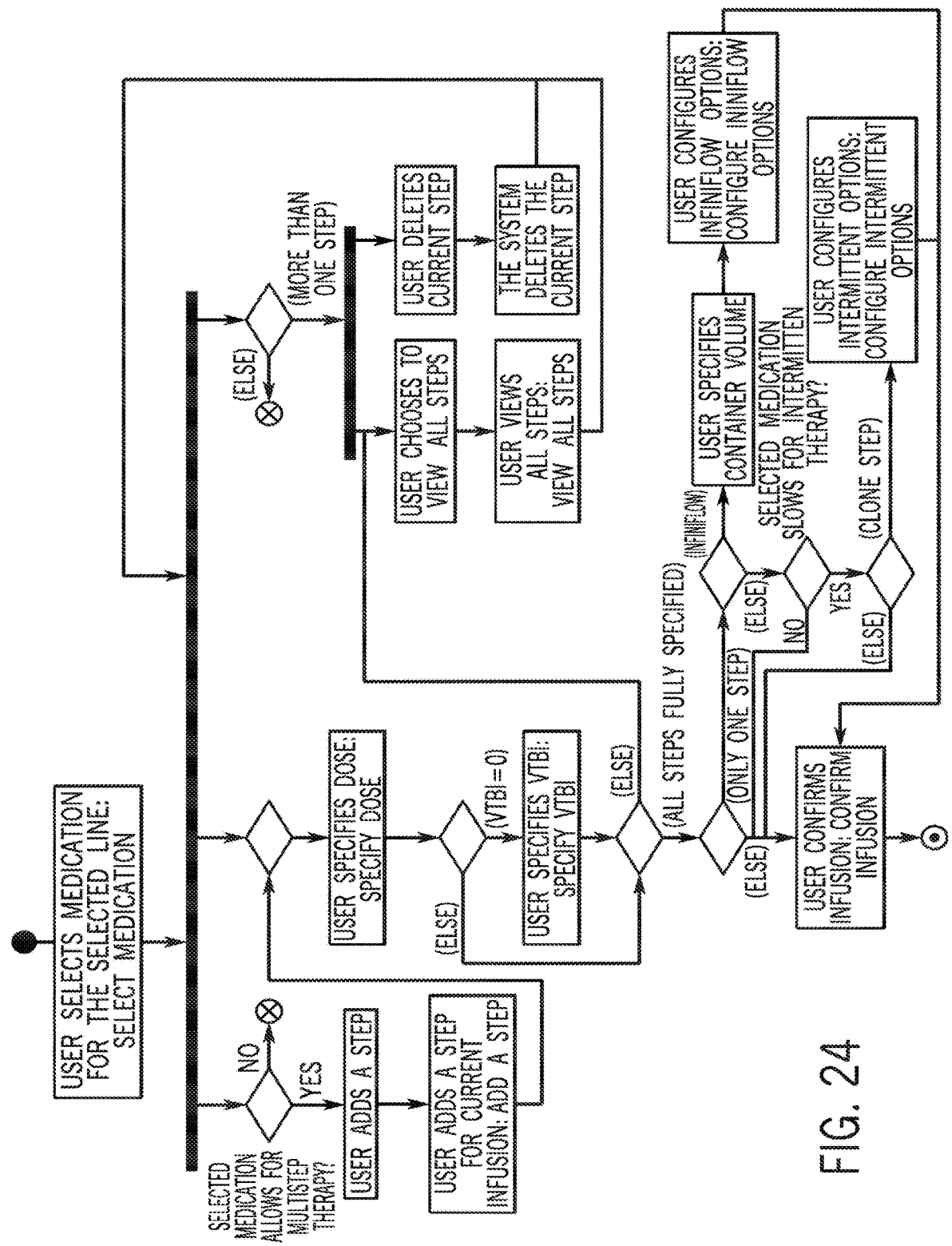
FIG. 24 depicts a flowchart of example method steps for converting a current continuous infusion to one of the various advanced infusion types.

FIG. 24 depicts a flowchart of example method steps for converting a current continuous infusion to one of the various advanced infusion types. As seen in FIG. 24, the caregiver may select a substance for infusion and, if the selected substance permits multiple infusion steps to be performed, the caregiver may choose to add a step to the current infusion. For the additional step, the caregiver may select or specify a dose and VTBI as described above. If the desired infusion type is an "infinite" flow infusion (i.e., there is only one step in the infusion sequence), then the caregiver may specify the volume of the delivery source container and configure the parameters for the "infinite" flow infusion. If the desired infusion type is an intermittent infusion (i.e., there is one repeated step), then the caregiver may clone the current step and configure the parameters for the intermittent infusion.

After the caregiver has added a step to the current infusion, the caregiver may select to view all steps for the infusion sequence at the infusion device. The caregiver may select one of the steps to view in further detail at the infusion device or to delete from the infusion sequence. Once the caregiver has configured all the desired steps for the infusion sequence, the caregiver may confirm the infusion steps and the infusion sequence as described above.

Figure 25:
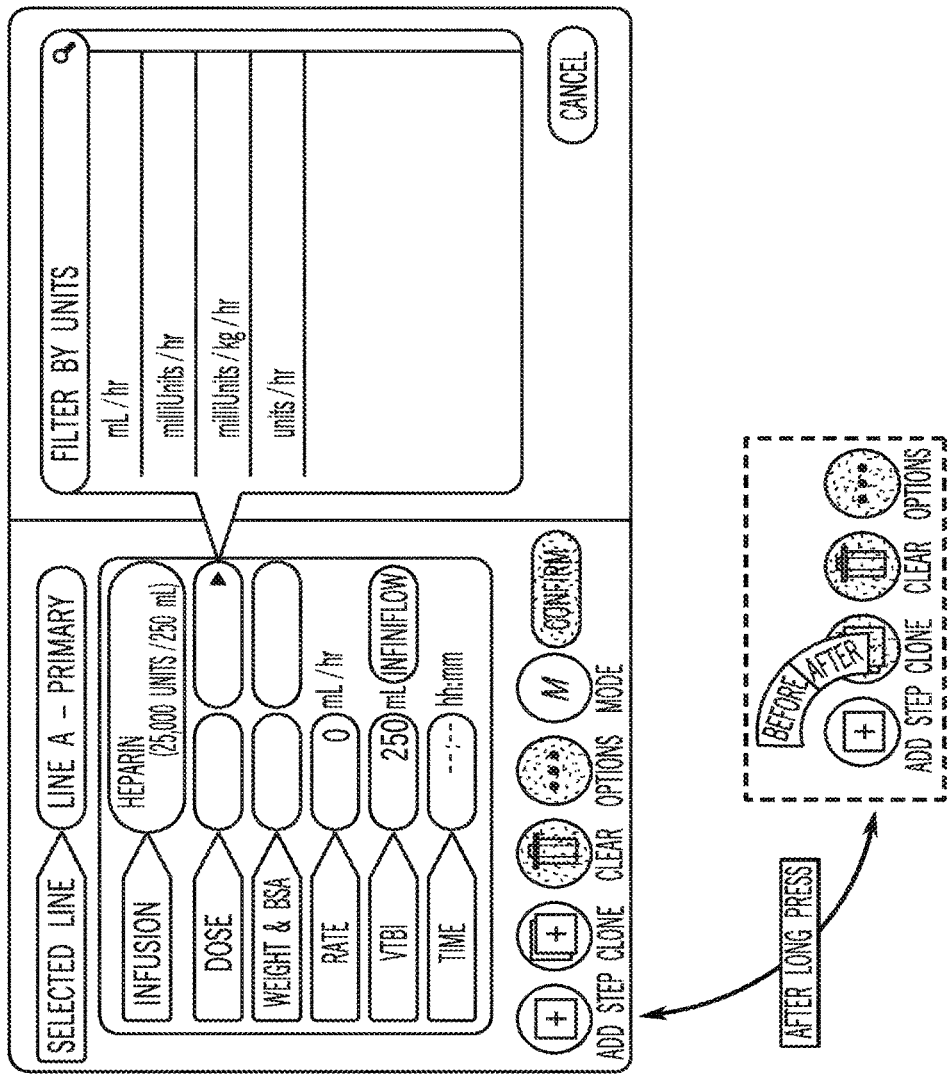
FIG. 25 depicts an example user interface of an infusion device at which the caregiver may add a step to an infusion sequence at the infusion device.

FIG. 25 depicts an example user interface of an infusion device at which the caregiver may add a step to an infusion sequence at the infusion device. As seen in FIG. 25, a caregiver may select a substance to be delivered to the patient and the corresponding delivery parameters as discussed above. The user interface also includes a button to add a step to the current infusion sequence as well as a button to clone the current step of the infusion sequence. The user interface may be configured to display in a pop-up menu additional buttons that allow the caregiver to specify whether the new step should be added to the infusion sequence either before or after the current step. The user interface may be configured to display the pop-up menu after a long press (i.e., n number of seconds) on the button to add a new step. The user interface in FIG. 25 also includes a "Mode" button that allows the caregiver to convert or configure the continuous infusion as an advanced infusion type (e.g., TPN, intermittent, multi-step, inter-channel sequencing, or "infinite" flow).

Figure 26A:
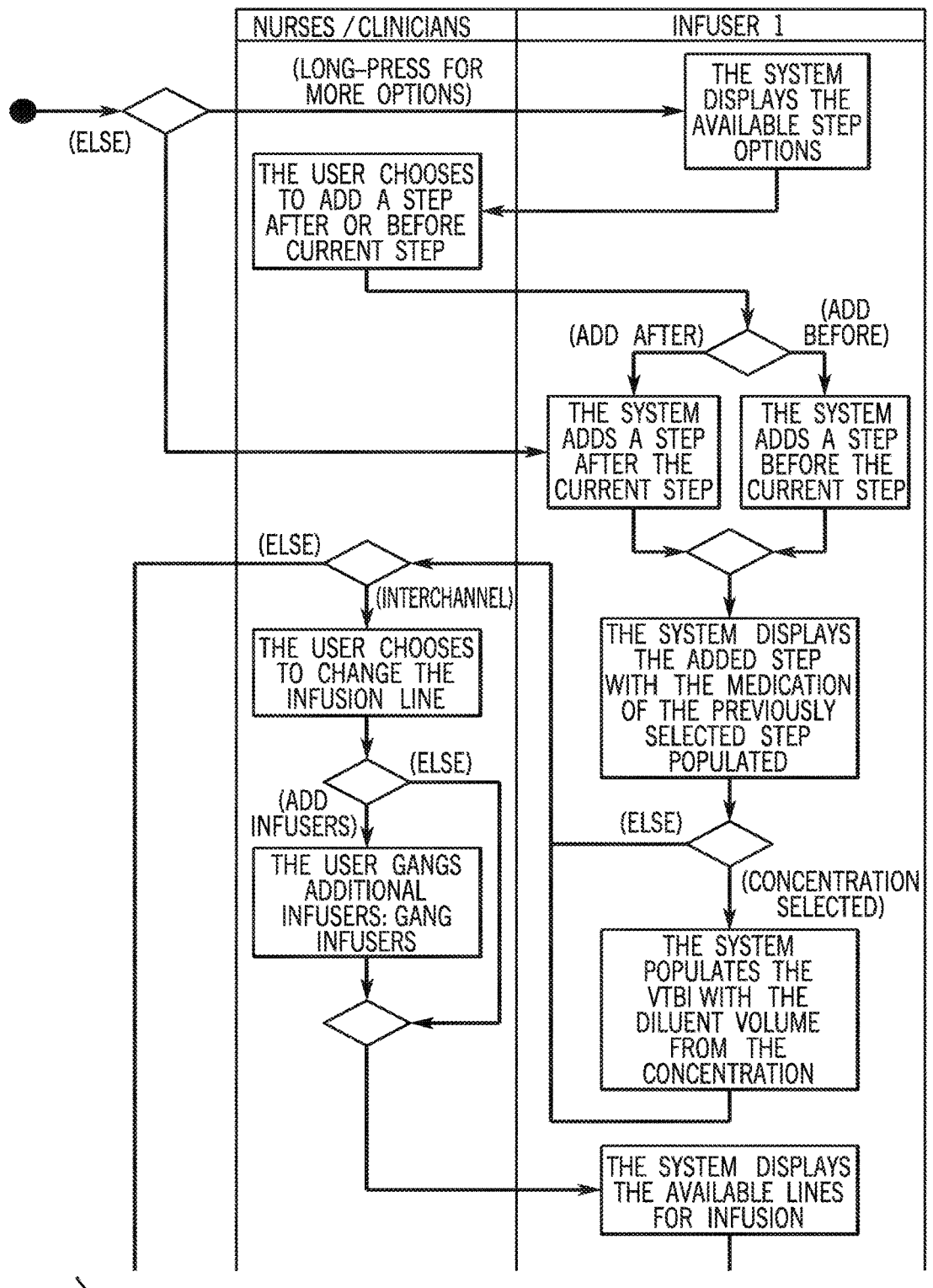
FIGS. 26A-26B depict a flowchart of example method steps for adding a new step to a current infusion sequence at an infusion device.
Figure 26B:
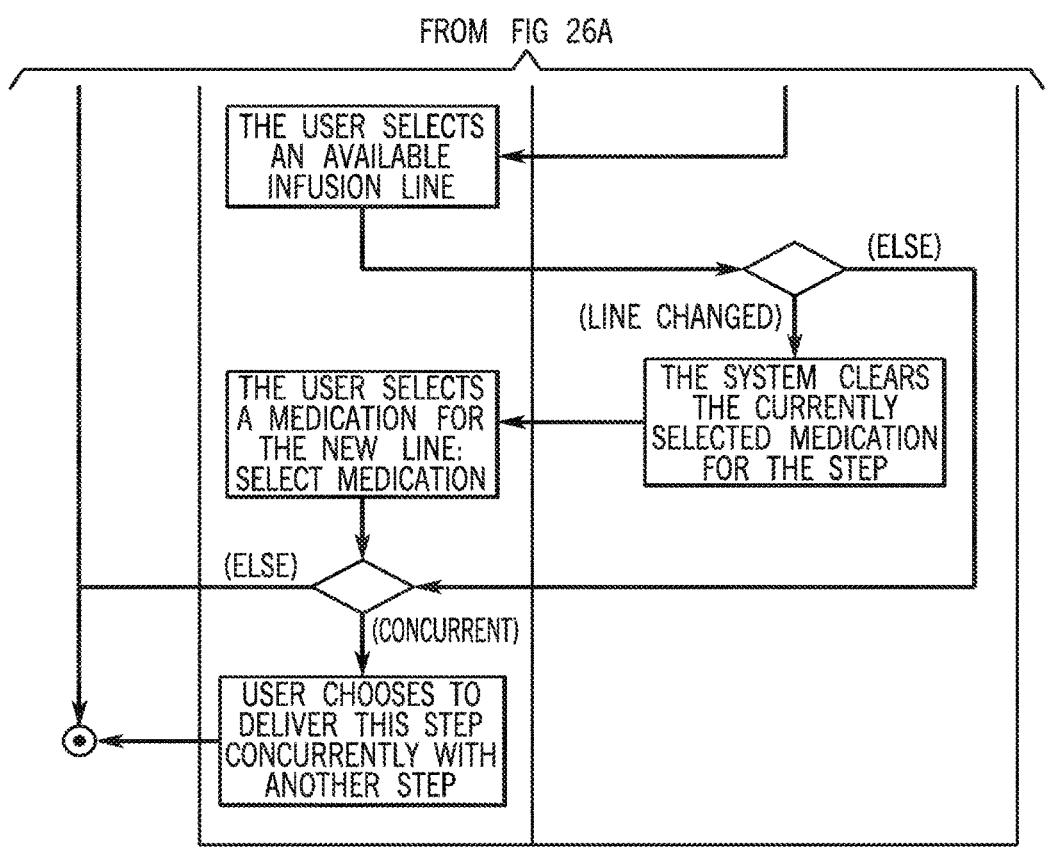

FIGS. 26A-26B depict a flowchart of example method steps for adding a new step to a current infusion sequence at an infusion device. As seen in FIGS. 26A-26B, the caregiver may select to add a step to the current infusion at the infusion device and specify whether the new step should be before or after the current step of the infusion. The infusion device may be configured to pre-populate the new step with the substance selected for the current step. If the caregiver specifies a new concentration for the new step, the infusion device may automatically calculate the VTBI based on the new concentration.

If the new step is added for an inter-channel sequencing infusion, the caregiver may select to change the infusion line for the new step, as well as add new infusion devices for the inter-channel sequencing infusion. If the caregiver selects to add a new infusion device, then the infusion device may display a list of infusion devices available to add, and the caregiver may select one of the infusion devices listed. If the caregiver has selected to change the line for the infusion during an inter-channel sequencing infusion, the infusion device may clear the substance selected for the current step allowing the caregiver to select a new substance to be delivered during the new step of the inter-channel sequencing infusion. The caregiver may also specify whether the new step for the inter-channel sequencing infusion should be performed concurrently with another step in the sequence.

Figure 27:
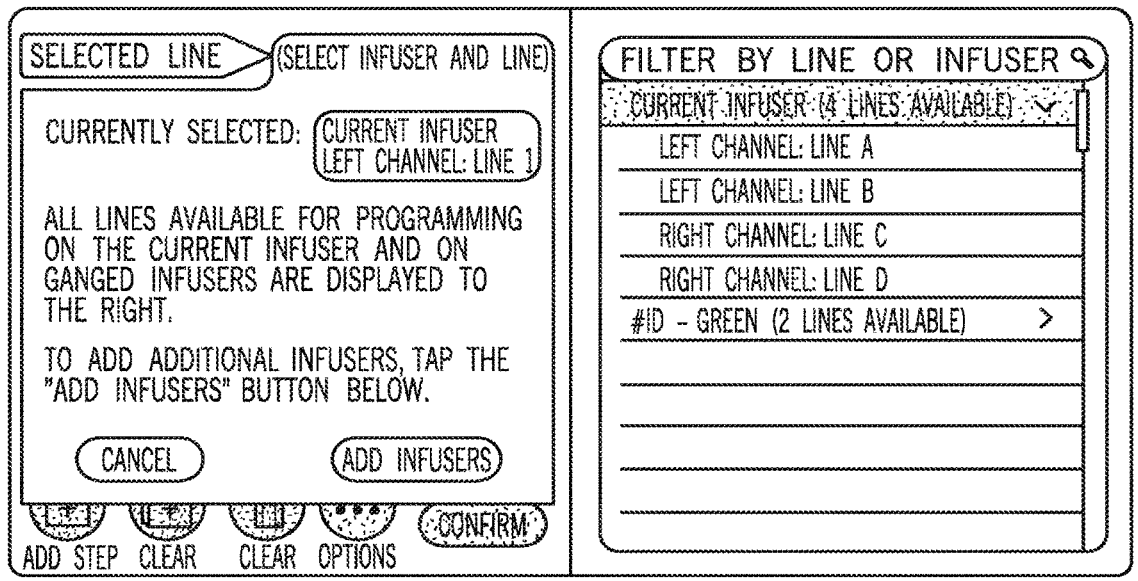
FIG. 27 depicts an example user interface of an infusion device for changing the line for an inter-channel sequencing infusion.

FIG. 27 depicts an example user interface of an infusion device for changing the line for an inter-channel sequencing infusion. As seen in FIG. 27, the interface displays the currently selected infuser, line, and channel. The interface also displays a list of lines available at the infusion device that may be selected for the infusion step currently being configured at the infusion device. In this example, the infusion device includes two channels (e.g., a Left Channel and a Right Channel) and two lines per channel (e.g., Line A and Line B for the Left Channel and Line C and Line D for the Right Channel). As also seen in FIG. 27, the list of lines may also identify one or more infusion devices in signal communication with the current infusion device with lines available to be selected for the current infusion step.

Figure 28:
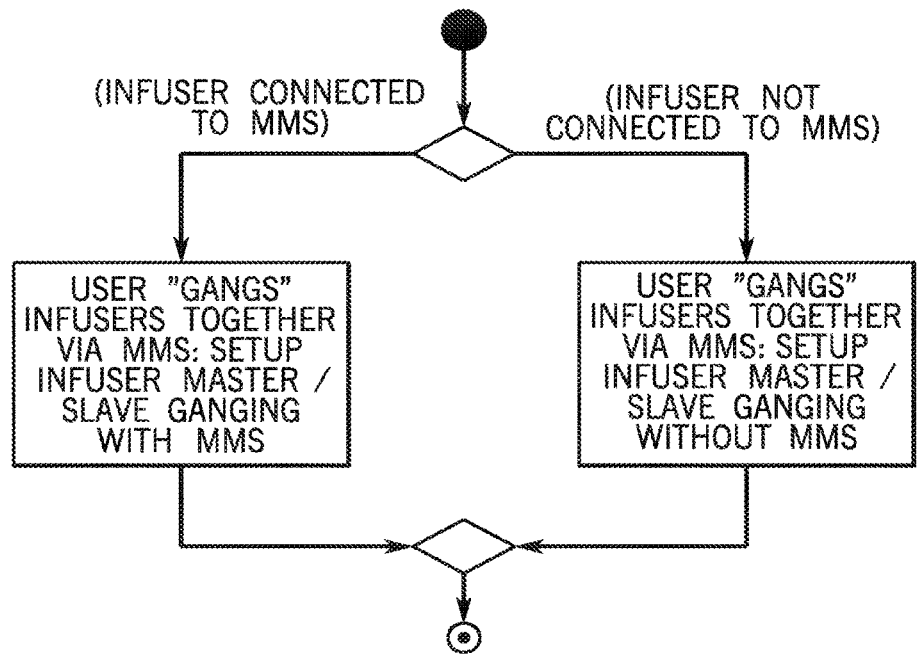
FIG. 28 depicts a flowchart of example method steps for ganging infusion devices.

Selecting additional infusion devices to perform a step of an infusion sequence may be referred to as "ganging" the infusion devices together for coordinated operation of an infusion to a patient. In addition, infusion devices that have each been configured to perform at least one step in an infusion sequence may be referred to as "ganged" infusion devices. FIG. 28 depicts a flowchart of example method steps for ganging infusion devices. As seen in FIG. 28, a caregiver may gang infusion devices together via a medication management system that interconnects multiple computing devices such that they are in signal communication with each other. As also seen in FIG. 28, a caregiver may gang infusion devices together by setting up a master/slave configuration between the computing devices without a medication management system. For this alternative approach to ganging infusion devices together, an infusion device may perform a device discovery operation to locate any nearby infusion devices or any other infusion devices associated with the current patient. As described in further detail below, infusion devices may be in signal communication with each other via wired, wireless, or both wired and wireless communications.

Figure 29:
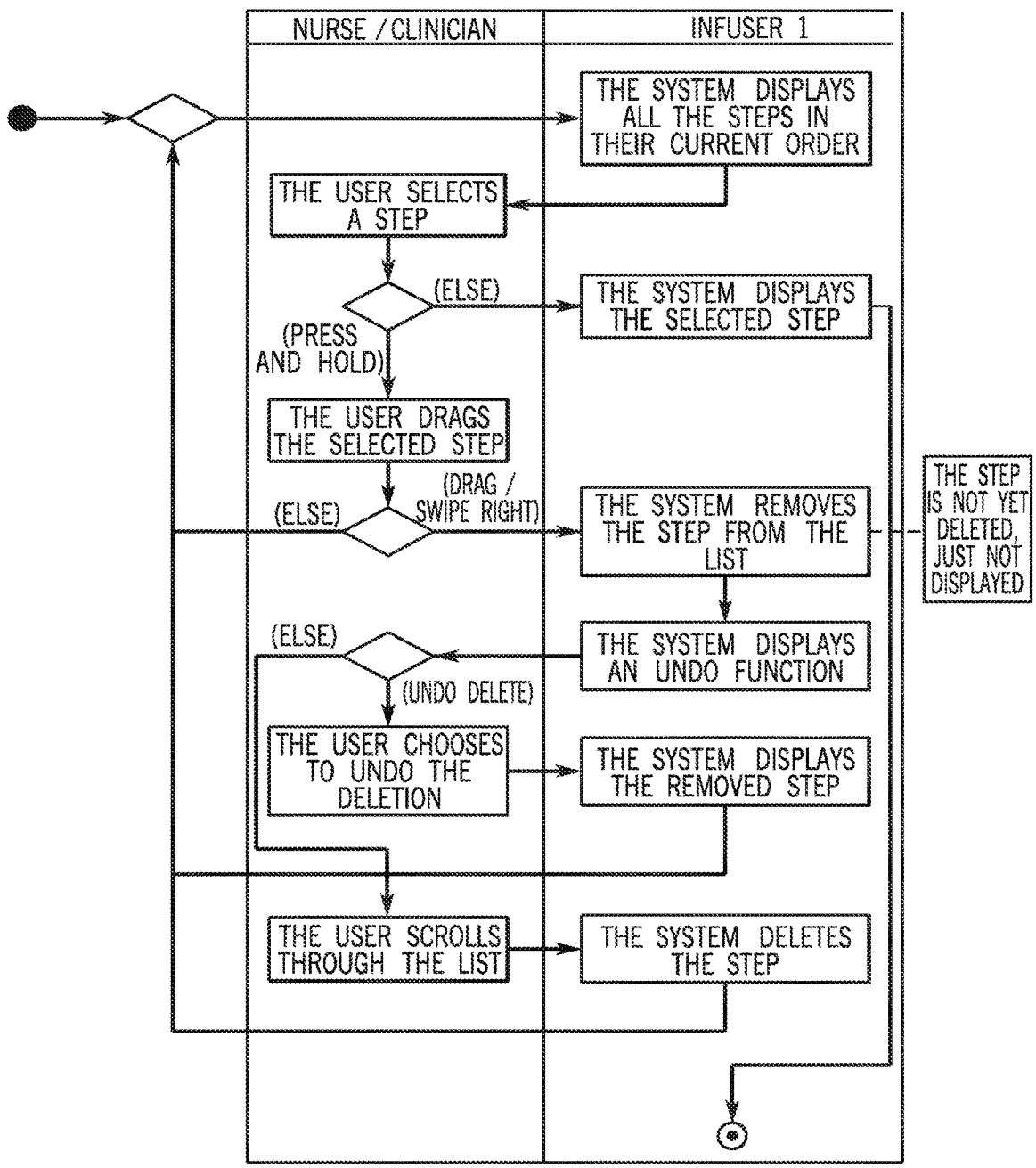
FIG. 29 depicts a flowchart of example method steps for viewing and manipulating the list of infusion steps configured for an infusion sequence.

For multi-step infusion sequences, the infusion device may allow the caregiver to view a list of the steps configured for an infusion sequence. FIG. 29 depicts a flowchart of example method steps for viewing and manipulating the list of infusion steps configured for an infusion sequence. As seen in FIG. 29, the caregiver may select to view the list of infusion steps, and the infusion device may display the list with the steps in their current order. The user may select one of the steps (e.g., by tapping the step), and the infusion device may display details for the selected step. The caregiver may also drag the selected step (e.g., by pressing and holding the step), to move or delete the selected step (e.g., drag and release). The caregiver may drag the step up or down to reposition the step in the list of steps (e.g., drag step no. 3 down to become step no. 5 and drag step. no 4 up. to become step no. 2). The caregiver may also drag the step right or left to delete the step from the list. The infusion device may be configured with an undo function that allows the caregiver to display a list of removed steps and select a removed step to add back to the list.

FIGS. 30-33 depict example user interfaces of an infusion device for displaying and manipulating a list of infusion sequence steps. FIG. 30 depicts an example user interface displaying a list of infusion sequence steps for an infusion to be delivered by an infusion device. As seen in FIG. 30, the list of infusion steps identifies, for each step, the infusion device, the line, the substance, and the infusion parameters associated with the step (e.g., substance, concentration, dose, rate, VTBI, and time). FIG. 31 depicts an example user interface of an infusion device for displaying the parameters associated with a step the caregiver has selected in the list of infusion steps. Similar to each step displayed in the list, the interface displays the details of the selected step (e.g., substance, concentration, dose, rate, VTBI, and time). FIG. 32 depicts the user interface of FIG. 30 in which the caregiver has selected one of the steps (step no. 4) in the list of infusion steps. FIG. 33 depicts the user interface of FIG. 32 in which the caregiver has dragged the selected step to the right to remove it from the list. As noted above, the user interface in FIG. 33 may also display a button to undo the removal of the removed step.

As noted above, a caregiver may convert a continuous infusion to an intermittent infusion. The continuous infusion being converted may be currently ongoing at the infusion device, i.e., the infusion device may currently be delivering a substance to the patient. The continuous infusion being converted may also be an infusion that has been configured but not yet started at the infusion device. The ability to convert a continuous infusion to an intermittent infusion may depend on the substance being infused. Some substances may permit intermittent infusion while other substances may not. Accordingly the infusion device may query a library of substances (e.g., a drug library) to determine whether intermittent infusion of the current substance is permitted. In addition, the infusion device may not permit a caregiver to convert a continuous infusion to an intermittent infusion until the continuous infusion has been fully configured.

Figure 34:
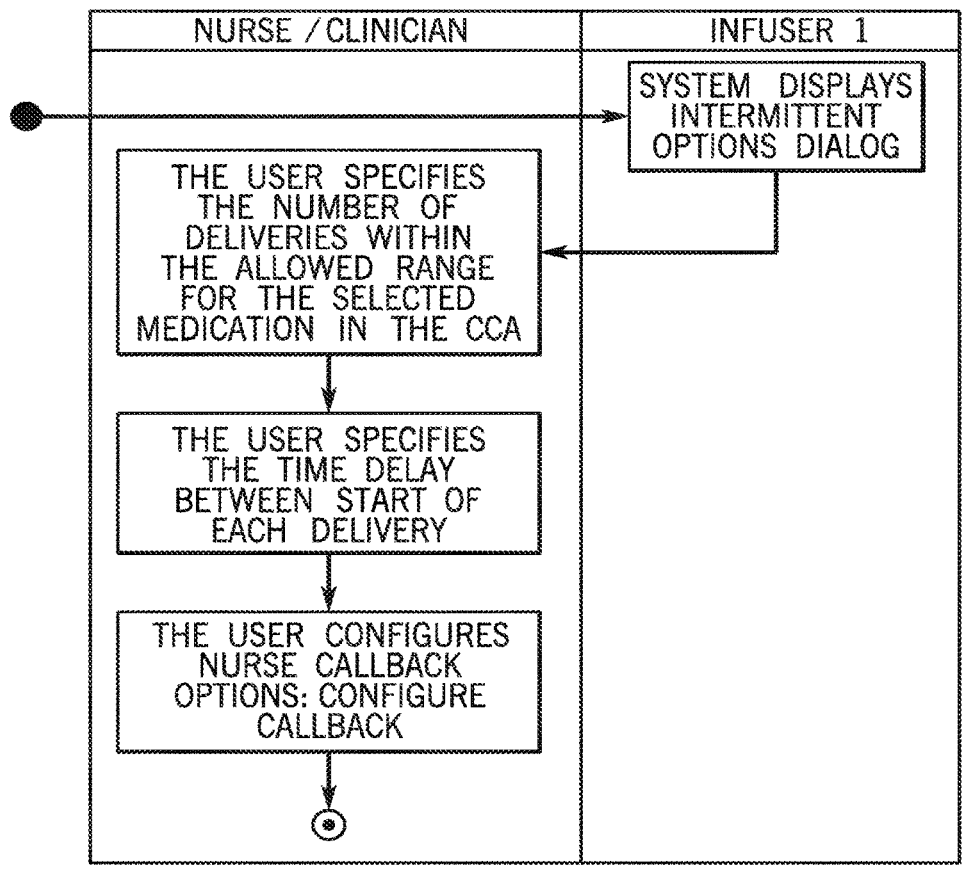
FIG. 34 depicts a flowchart of example method steps for converting a continuous infusion to an intermittent infusion.

FIG. 34 depicts a flowchart of example method steps for converting a continuous infusion to an intermittent infusion. After a continuous infusion has been configured, the caregiver may select a button at a user interface of the infusion device to display the options for an intermittent infusion. The caregiver may then select or specify the number of infusion steps for the intermittent infusion. The infusion device may limit the total number of infusion steps for the intermittent infusion based on a permitted range for the selected substance. The infusion device may likewise query a substance library (e.g., a drug library) for the permitted range. The caregiver may also select or specify the time delay between each step of the intermittent infusion as well as callback options for the intermittent infusion. A callback refers to a notification provided to the caregiver at the end of an individual infusion step as well as at the end of the intermittent infusion.

Figure 35:
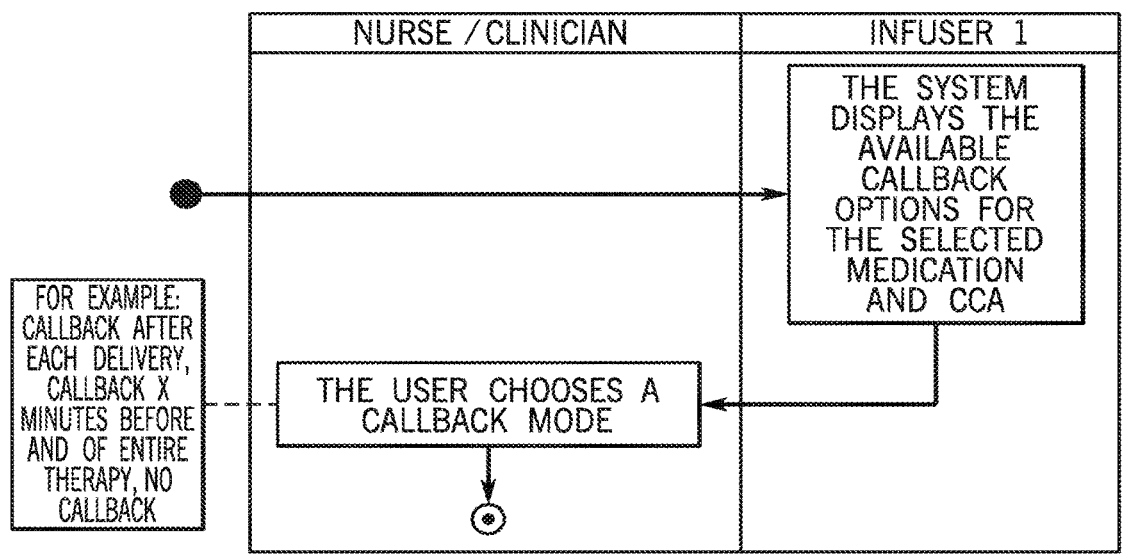
FIG. 35 depicts a flowchart of example method steps for specifying one or more callback options.

FIG. 35 depicts a flowchart of example method steps for specifying one or more callback options. The infusion device may display a list of callback options available for selection, and the caregiver may select a callback option to be provided upon completion of one or more individual infusion steps or upon completion of the entire intermittent infusion. The caregiver may also specify that the infusion device should not provide a callback for one or more of the individual infusion steps or the intermittent infusion.

Figure 36:
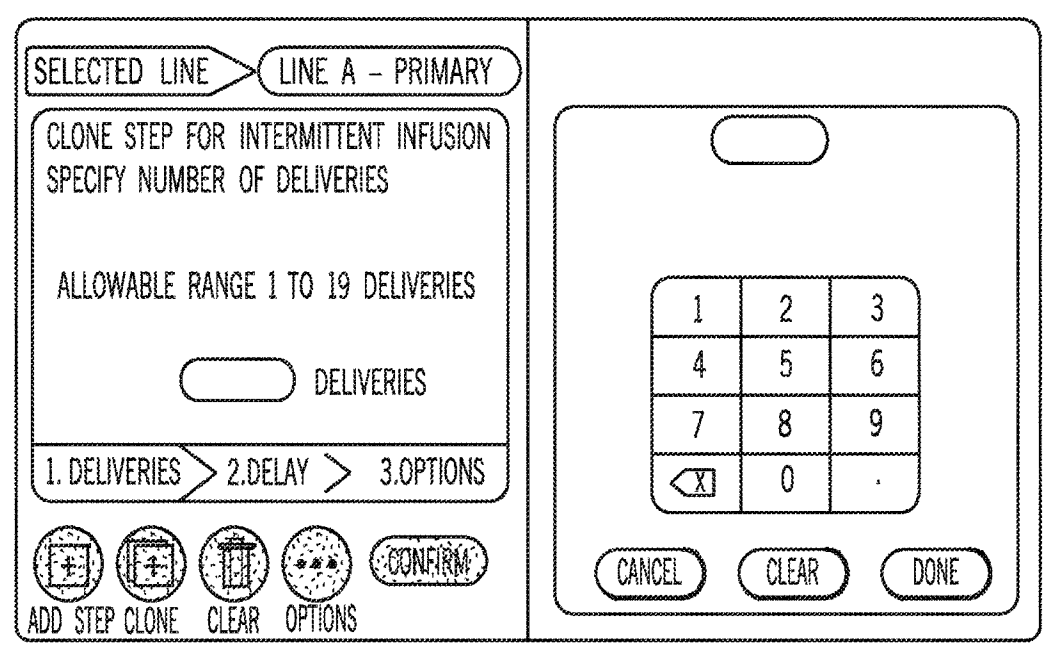

FIG. 36 depicts an example user interface for cloning a current step of an intermittent infusion. As seen in FIG. 36, the user interface display the current line of the infusion device and the allowable range for the total number of infusion steps that may be performed for the substance in an intermittent infusion. The user interface includes a keypad at which the caregiver may specify the total number of infusion steps (i.e., deliveries) that should be performed. The user interface may also allow the caregiver to specify the delay between steps, and options for each step (e.g., callback options).

Figure 37:
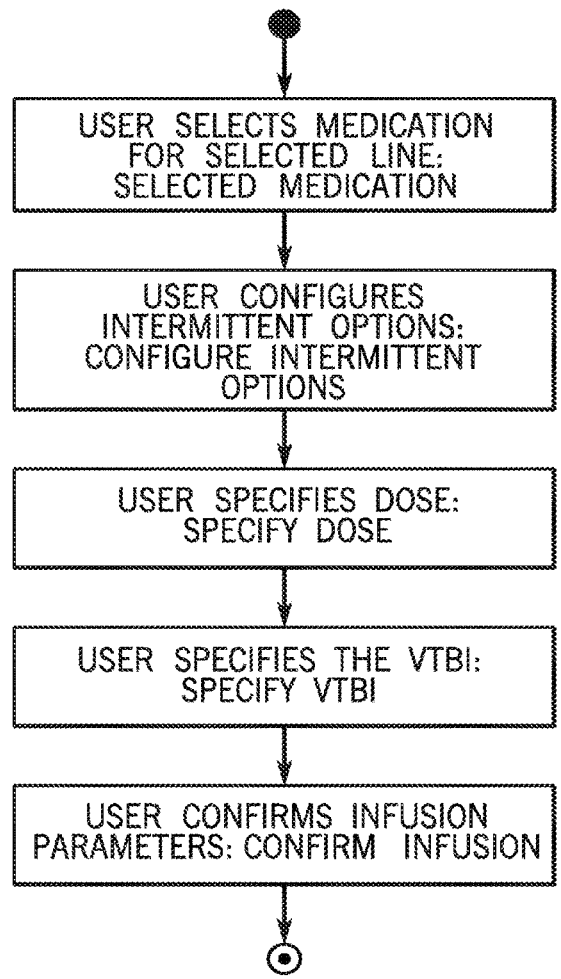
FIG. 37 depicts a flowchart of example methods steps for configuring an intermittent infusion.

FIG. 37 depicts a flowchart of example methods steps for configuring an intermittent infusion. As seen in FIG. 37, the caregiver may select a substance to be delivered to the patient, the intermittent infusion options, the dose, and the VTBI. With the intermittent infusion configured, the caregiver may confirm the parameters.

As also noted above, a caregiver may also convert a continuous infusion at the infusion device to an "infinite" flow infusion. As noted above, an "infinite" flow infusion refers to an infusion in which an infusion device utilizes two delivery lines on a single cassette channel wherein the infusion device automatically switches to the other line when the current line completes its infusion such that there is no interruption in the delivery. Each delivery line may be connected to a respective delivery source such that the caregiver may replace a depleted delivery source with a full delivery source while the other delivery source continues to deliver the substance to the patient. The switching between delivery sources allows the caregiver to continually swap out depleted delivery sources during the infusion without interrupting the continuous delivery of the substance to the patient. In this way, the infusion may continue while new delivery sources are connected to the infusion device. Infusion may thus continue without pausing to connect new containers.

Figure 38:
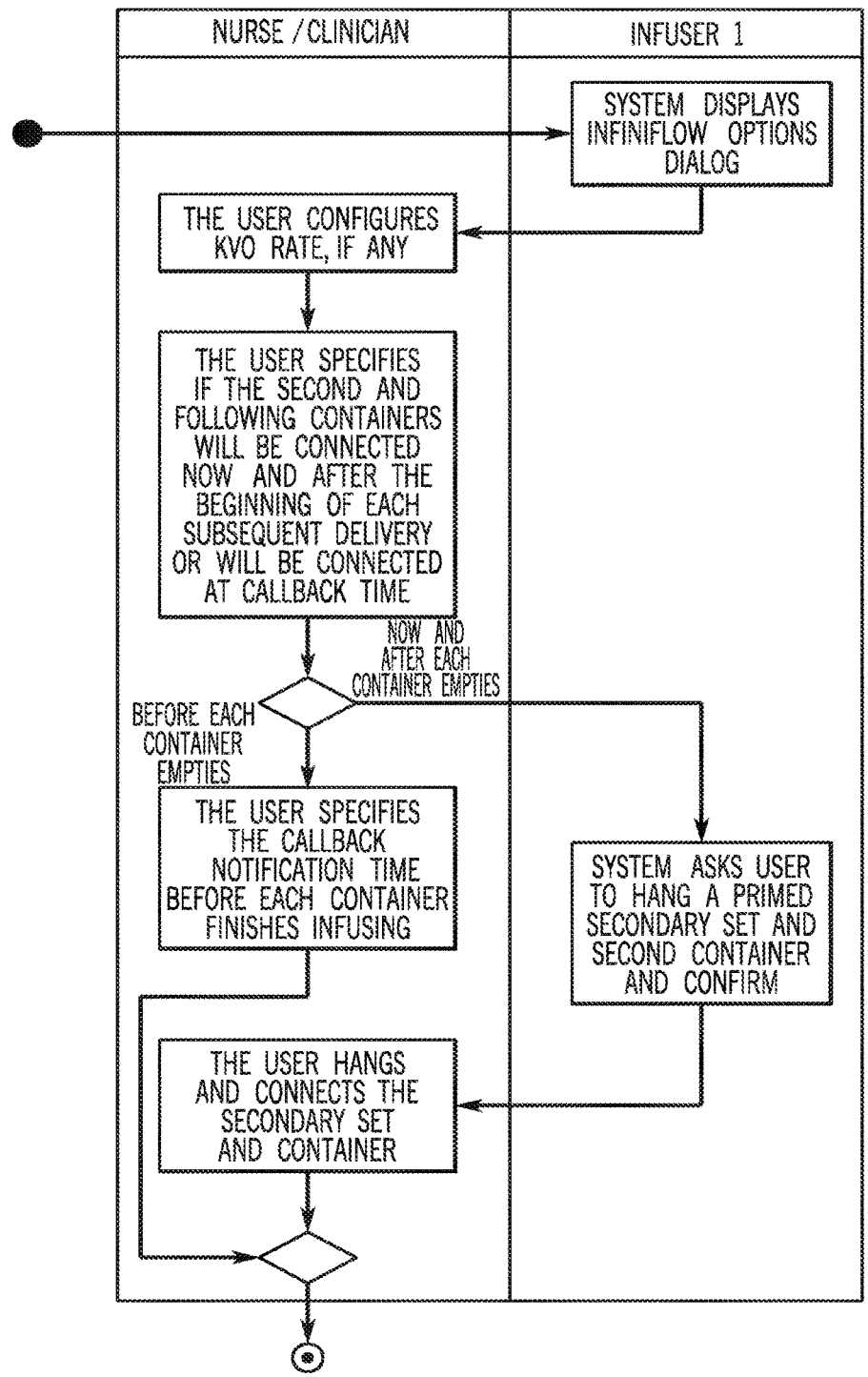
FIG. 38 depicts a flowchart of example method steps for converting a continuous infusion to an "infinite" flow infusion and configuring the "infinite" flow infusion.

FIG. 38 depicts a flowchart of example method steps for converting a continuous infusion to an "infinite" flow infusion and configuring the "infinite" flow infusion. After a continuous infusion has been configured, the caregiver may select a button at a user interface of the infusion device to display the options for an "infinite" flow infusion. Like converting to an intermittent infusion, the ability to convert a continuous infusion to an "infinite" flow infusion may be restricted until the continuous flow infusion has been fully configured.

When the caregiver selects to convert and configure an "infinite" flow infusion, the infusion device may display options for the "infinite" flow infusion. As seen in FIG. 38, the caregiver may, if necessary, specify at the infusion device a KVO rate. With the total VTBI having already been configured, the infusion device requests that the caregiver specify the volume of the delivery sources that will be used for the "infinite" flow infusion. The infusion device also requests that the caregiver indicate whether the additional and subsequent delivery sources with be attached to the infusion device before or after the delivery sources are fully depleted. If the caregiver indicates the delivery sources will be replaced before they are fully depleted, the caregiver may configure a callback such that the caregiver is notified a predetermined amount of time before the delivery source is fully depleted (e.g., x number of minutes or seconds). If the caregiver indicates that depleted delivery sources will be replaced after they are depleted, the infusion device may prompt the caregiver to attach one or more additional delivery sources to the infusion device before the "infinite" flow infusion begins.

Figure 39:
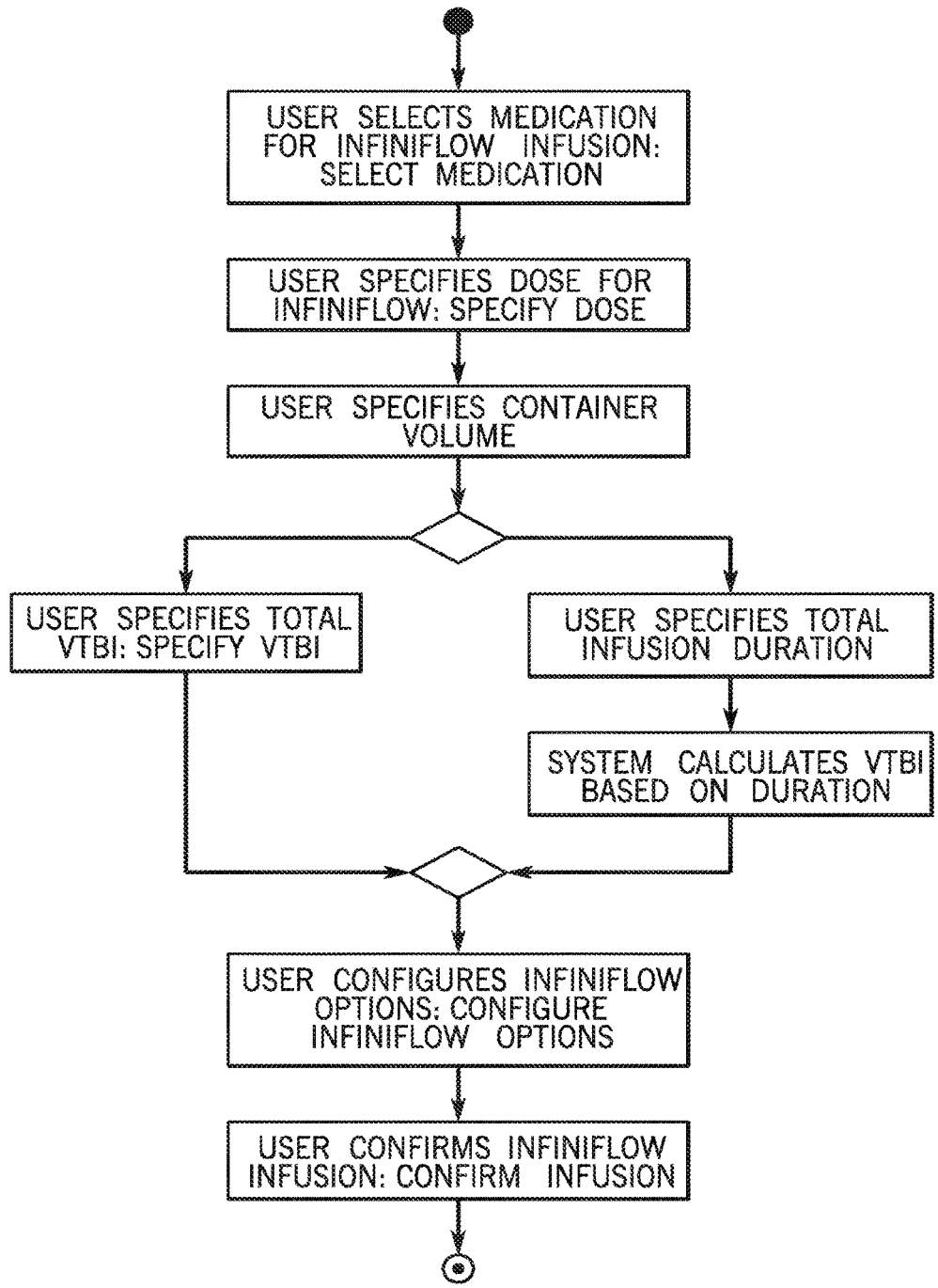
FIG. 39 depicts a flowchart of example method steps for configuring an "infinite" flow infusion.

FIG. 39 depicts a flowchart of example method steps for configuring an "infinite" flow infusion. As seen in FIG. 39, the caregiver may select the substance to be delivered to the patient, the dose, and the volume of the delivery sources that will be used for the "infinite" flow infusion. Once the volume of the delivery sources has been specified, the caregiver may specify the total VTBI of the total infusion duration. If the caregiver specifies the VTBI, then the infusion device may automatically calculate the total infusion duration. If the caregiver specifies the total infusion duration, then the infusion device may automatically calculate the VTBI. The caregiver may then specify various options for the "infinite" flow infusion such as the KVO rate and the callback options as discussed above. As also noted above, the infusion device will prompt the caregiver to connect an addition delivery source to the infusion device prior to starting the infusion if the caregiver opts to be notified when a delivery source is depleted. The caregiver may then connect a new delivery source to the infusion device after each delivery source that empties. As also noted above, the caregiver may opt to be notified prior to the depletion of a delivery source in which case the caregiver may only connect the subsequent delivery source when the current delivery source is near empty. Waiting to connect a subsequent delivery source until receipt of notification may be advantageous where the substances delivered to the patient are in limited supply or need to be refrigerated. In other words, requesting notification of a near-empty delivery source allows the caregiver to connect the next delivery source only when it becomes necessary. Having configured the options for the "infinite" flow infusion, the caregiver may confirm and initiate the infusion at the infusion device.

Figure 40A:
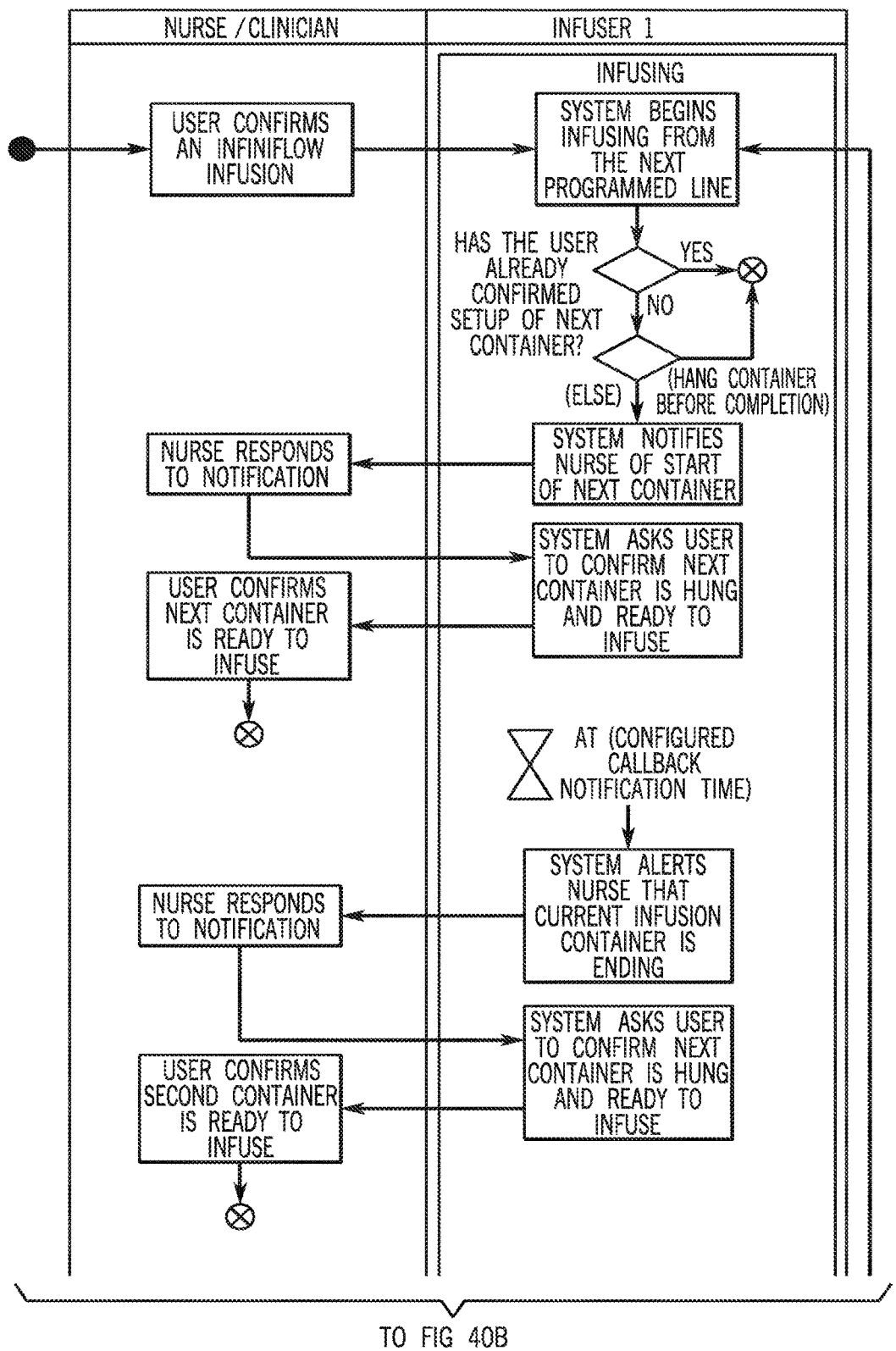
FIGS. 40A-40B depict a flowchart of example method steps for an "infinite" flow infusion.
Figure 40B:
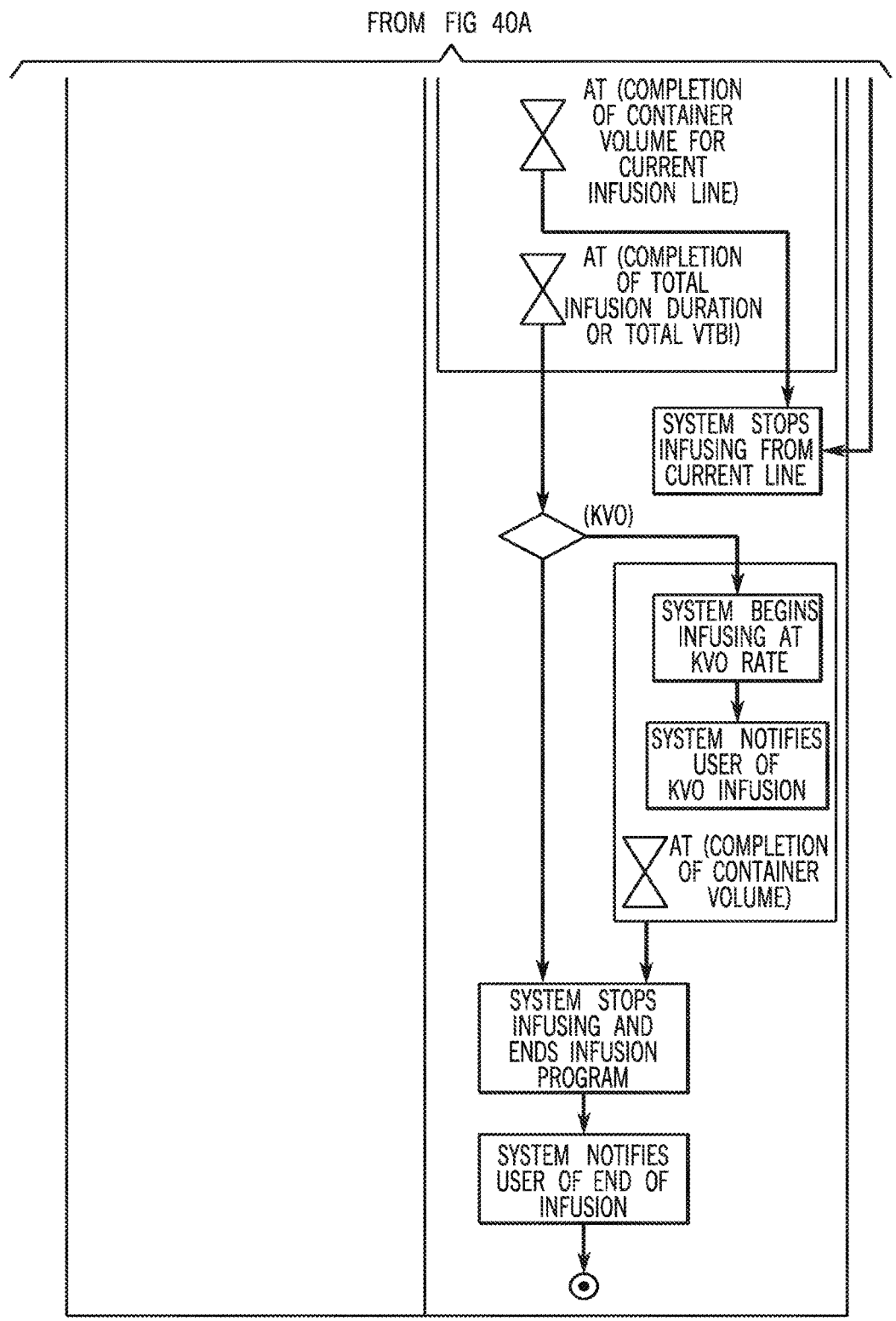

FIGS. 40A-40B depict a flowchart of example method steps for an "infinite" flow infusion. As seen in FIGS. 40A-40B, the infusion device may request confirmation from the caregiver that the subsequent delivery source has been connected to the infusion device. When the caregiver connects the subsequent delivery source, the caregiver may confirm at the infusion device that the subsequent delivery source has been connected. The infusion device may also provide a notification to the caregiver that the current delivery source is near-empty as described above. The caregiver may respond to the notification by replacing the near-empty delivery source with a new delivery source. When the current delivery source has been depleted, the infusion device stops infusing on the current line, switches to the next line connected to a full delivery source, and begins infusing on the new line. If the infusion device has reached the VTBI or the total infusion duration, the infusion device may stop the infusion procedure or execute any end-of-procedure actions (e.g., infusing at a specified KVO rate). The infusion device may likewise notify the caregiver that the infusion procedure is complete.

Figure 41A:
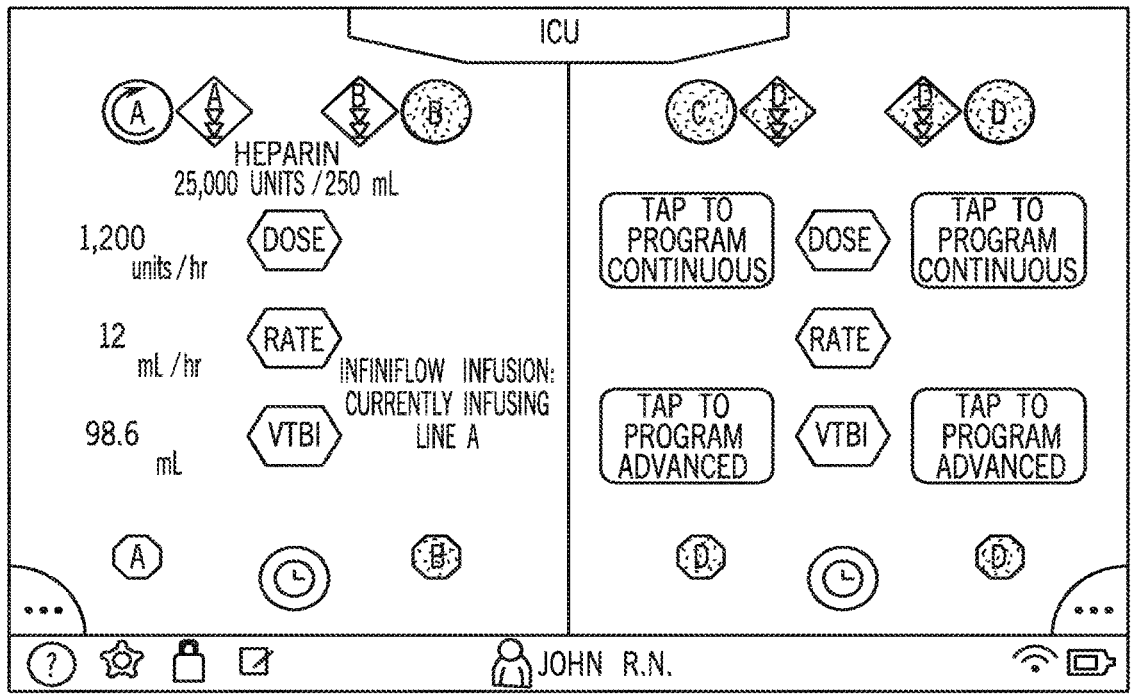
FIG. 41A depicts an example user interface of an infusion device during an "infinite" infusion flow.
Figure 41B:
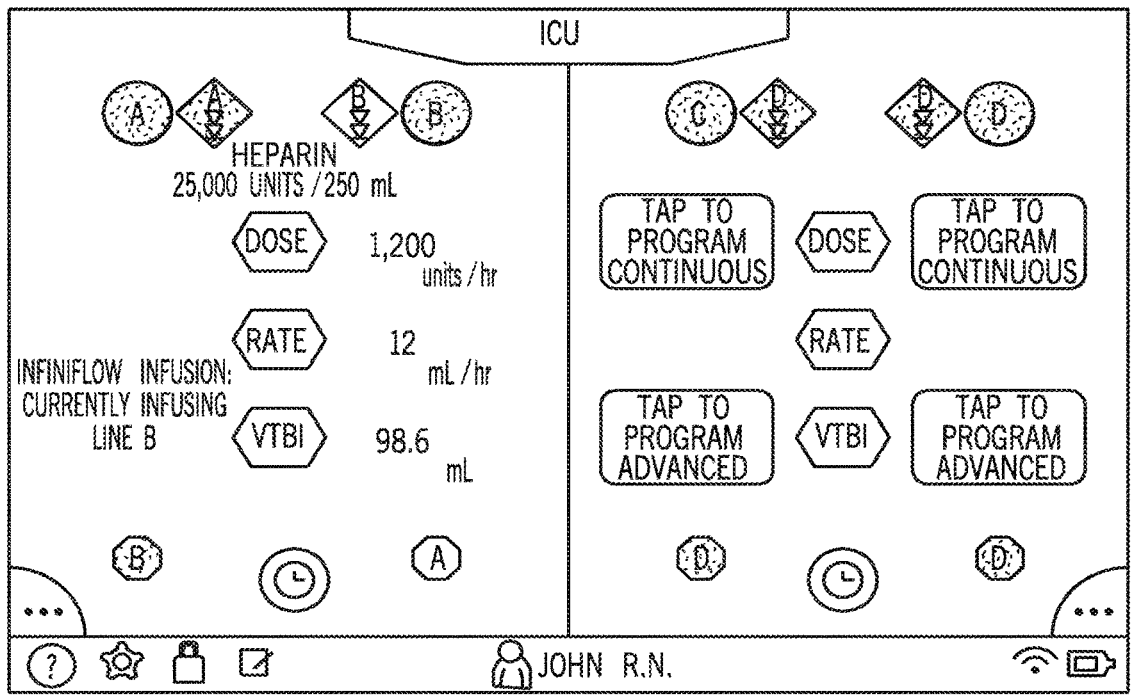
FIG. 41B depicts another example user interface of an infusion device during an "infinite" infusion flow.

FIG. 41A-B depict example user interfaces of an infusion device during an "infinite" infusion flow. As seen in FIG. 41A, the infusion device is currently infusing the patient via a first line (e.g., Line A) of the infusion device. When the delivery source connected to the first line is depleted, the infusion device switches to infuse the patient via another line of the infusion device. As seen in FIG. 41B, the infusion device has switched to infuse the patient via a second line (e.g., Line B) of the infusion device. A caregiver may thus replace the delivery source connected to the first line with a new delivery source to subsequently use when the delivery source for the second line is depleted.

Figure 42A:
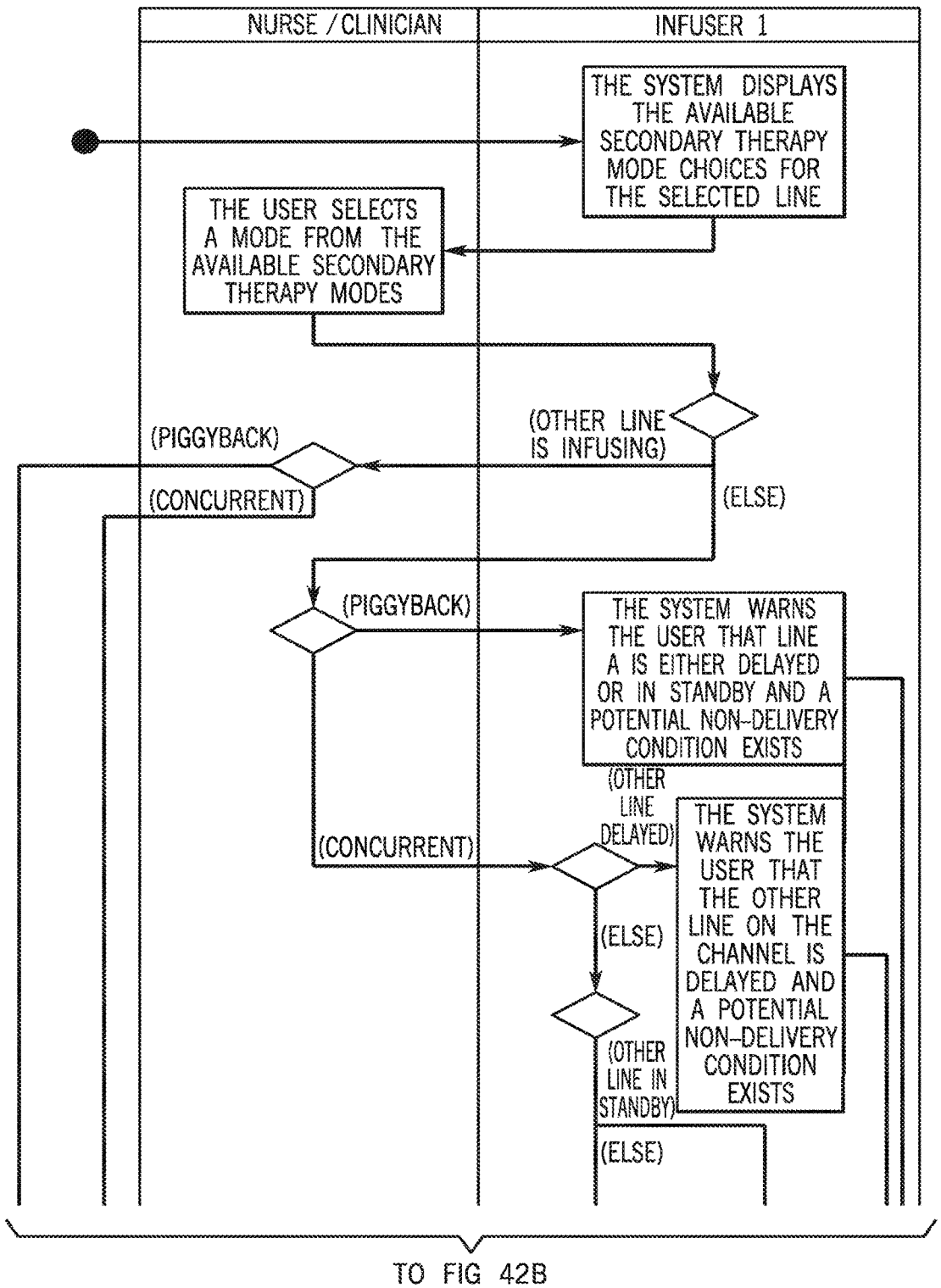
FIGS. 42A-42B depict a flowchart of example method steps for selecting a secondary infusion at an infusion device.
Figure 42B:
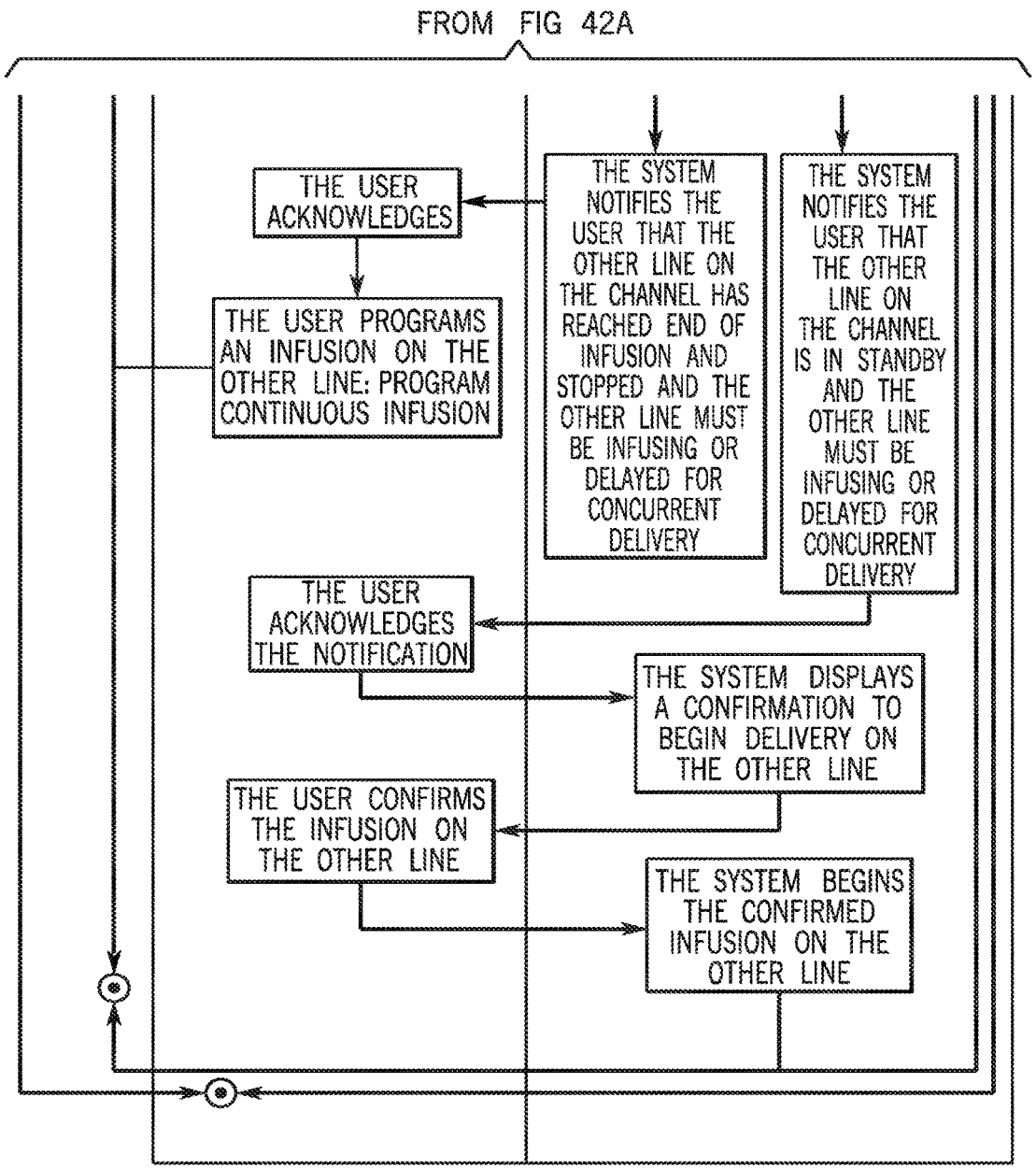

As noted above, a caregiver may configure various secondary infusions (e.g., concurrent infusions and piggyback infusions) during an infusion currently being performed at the infusion device. FIGS. 42A-42B depict a flowchart of example method steps for selecting a secondary infusion at infusion device. As seen in FIGS. 42A-42B, the infusion device may display a user interface with buttons allowing the caregiver to select a secondary infusion via a selected line at the infusion device. The caregiver may select a secondary infusion type (e.g., concurrent or piggyback) and the infusion device may determine whether the other line is currently infusing.

If the other line of the infusion device is currently infusing, then the caregiver may proceed with configuring the concurrent or piggyback infusion as described above. If, however, the other line of the infusion device is not currently infusing, then the infusion device may assess the status of the other line in order to provide notifications or warnings to the caregiver. As an example, the infusion device may notify or warn the caregiver that the other line is currently in a potential non-delivery condition exists, i.e., that the infusion device might not be able to perform the secondary infusion selected. A non-delivery condition may exist where the other line is delayed, is in standby, or has completed its infusion. If a non-delivery condition exists, the infusion device may notify the caregiver that the other line must be currently infusing in order to perform the secondary infusion via the selected line. The notifications and warnings may advantageously avoid situations where, e.g., the infusion device attempts to switch back to a line that may not resume an infusion upon completion of a piggyback infusion. The infusion device may prompt the caregiver to initiate or restart an infusion at the other line. Once initiated or restarted, the caregiver may proceed with configuring the parameters of the secondary infusion.

FIG. 61 depicts an example user interface of an infusion device for notifying or warning a caregiver regarding a non-delivery condition. As seen in FIG. 61, the user interface informs the caregiver that the infusion device cannot initiate a secondary infusion unless the other line is currently infusing. The user interface also includes buttons to cancel the secondary infusion or view the settings configured for the other line.

FIG. 62 depicts a flowchart of example method steps for configuring a piggyback infusion at an infusion device. As seen in FIG. 62, the caregiver may select or specify the substance to be delivered to the patient, the dose, the VTBI, and various piggyback infusion options (e.g., an action to perform at the end of the infusion). Once the parameters for the piggyback infusion have been configured, the caregiver may review the parameters and initiate the piggyback infusion. FIG. 63 depicts a flowchart of example method steps for configuring piggyback infusion options including selecting or specifying an action to perform at the end of the piggyback infusion.

Figure 64:
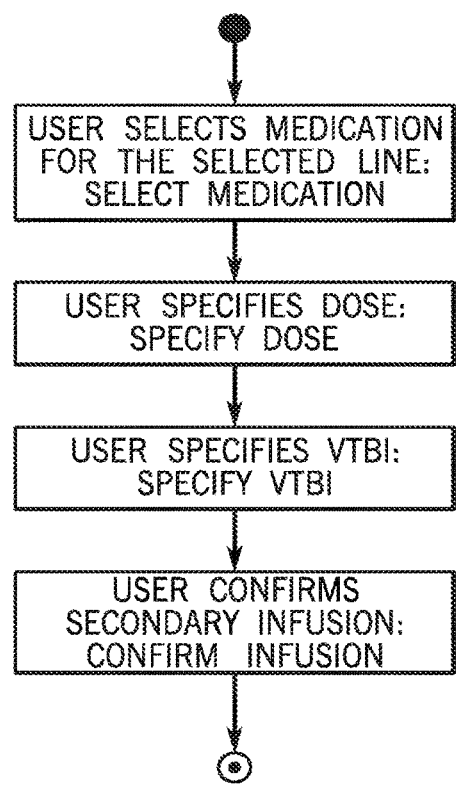
FIG. 64 depicts a flowchart of example method steps for configuring a concurrent infusion.

FIG. 64 depicts a flowchart of example method steps for configuring a concurrent infusion. Like a piggyback infusion, the caregiver may select or specify the substance to be delivered to the patient, the dose, the VTBI, and various concurrent infusion options.

As also noted above, a caregiver may configure various advanced infusion types at an infusion device (e.g., TPN, intermittent, multi-step, inter-channel sequencing, and "infinite" flow). As also noted above, a caregiver may select an advanced infusion type via "Mode" button on the user interface to add a step to a continuous infusion. Alternatively, the infusion device may present a user interface with "quick mode" selection buttons.

Figure 43:
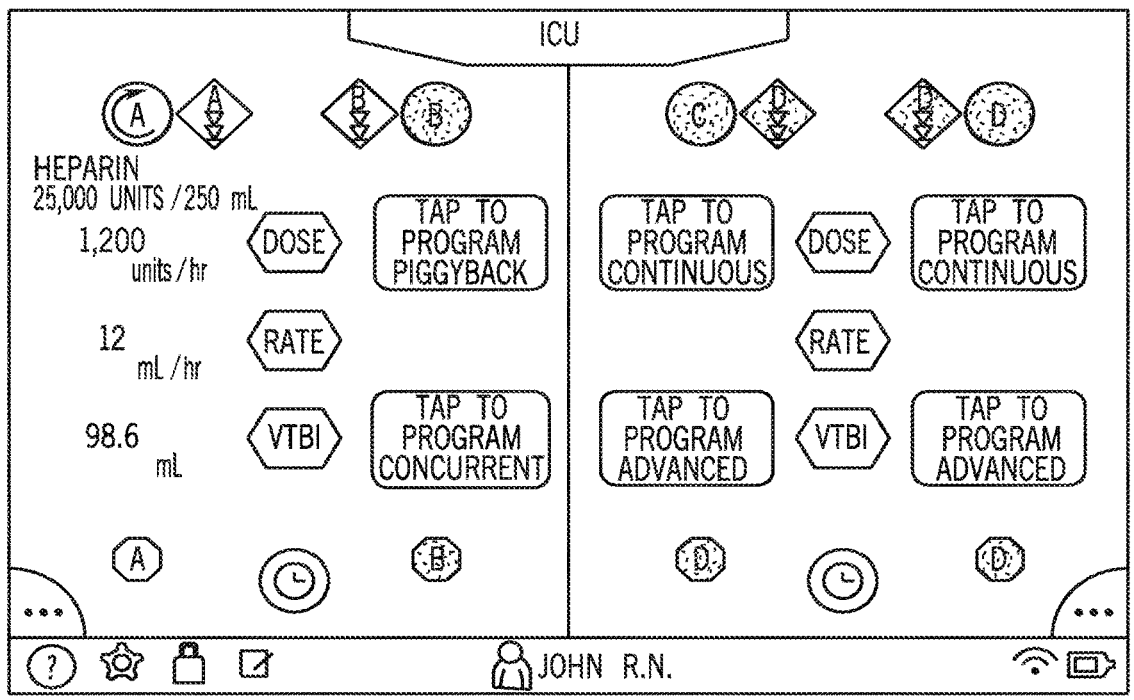
FIG. 43 depicts an example user interface of an infusion device at which a caregiver may select to configure an advanced infusion type.

FIG. 43 depicts an example user interface of an infusion device at which a caregiver may select to configure an advanced infusion type. The user interface includes buttons for configuring infusions at two infusion devices each having two lines. As seen in FIG. 43, the primary line (Line A) of the first infusion device is currently performing an infusion at the patient. The user may select to program another infusion at the secondary line (Line B) of the first infusion device such as a concurrent or piggyback infusion as discussed above. The caregiver may also select to configure an infusion at the primary line (Line C) or the secondary line (Line D) of the second infusion device. As also seen in FIG. 43, the caregiver may select one of the buttons to program a continuous infusion at the lines of the second infusion device or an advanced infusion type.

Figure 44:
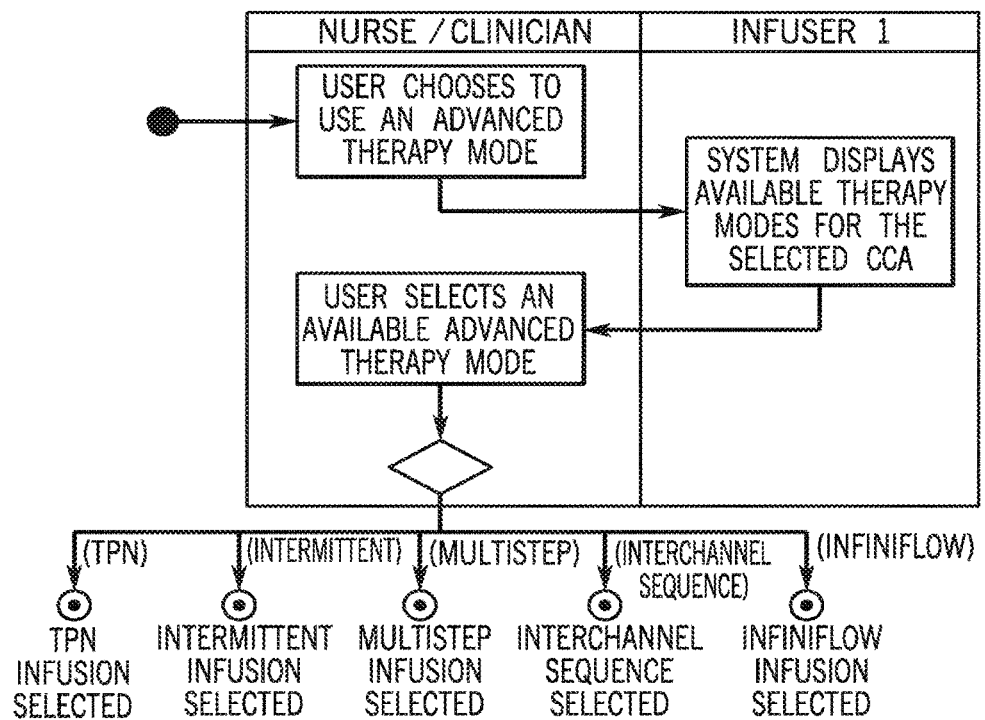
FIG. 44 depicts a flowchart of example method steps for selecting an advanced infusion type to configure at an infusion device.

FIG. 44 depicts a flowchart of example method steps for selecting an advanced infusion type to configure at an infusion device. Upon selection of an advanced infusion type button, the infusion device may display a list of the advanced infusion types available for selection. As noted above, advanced infusion types may include TPN, intermittent, multi-step, inter-channel sequencing, and "infinite" flow. The user may then select the desired advanced infusion type and configure the parameters for the advanced infusion type selected.

Figure 45:
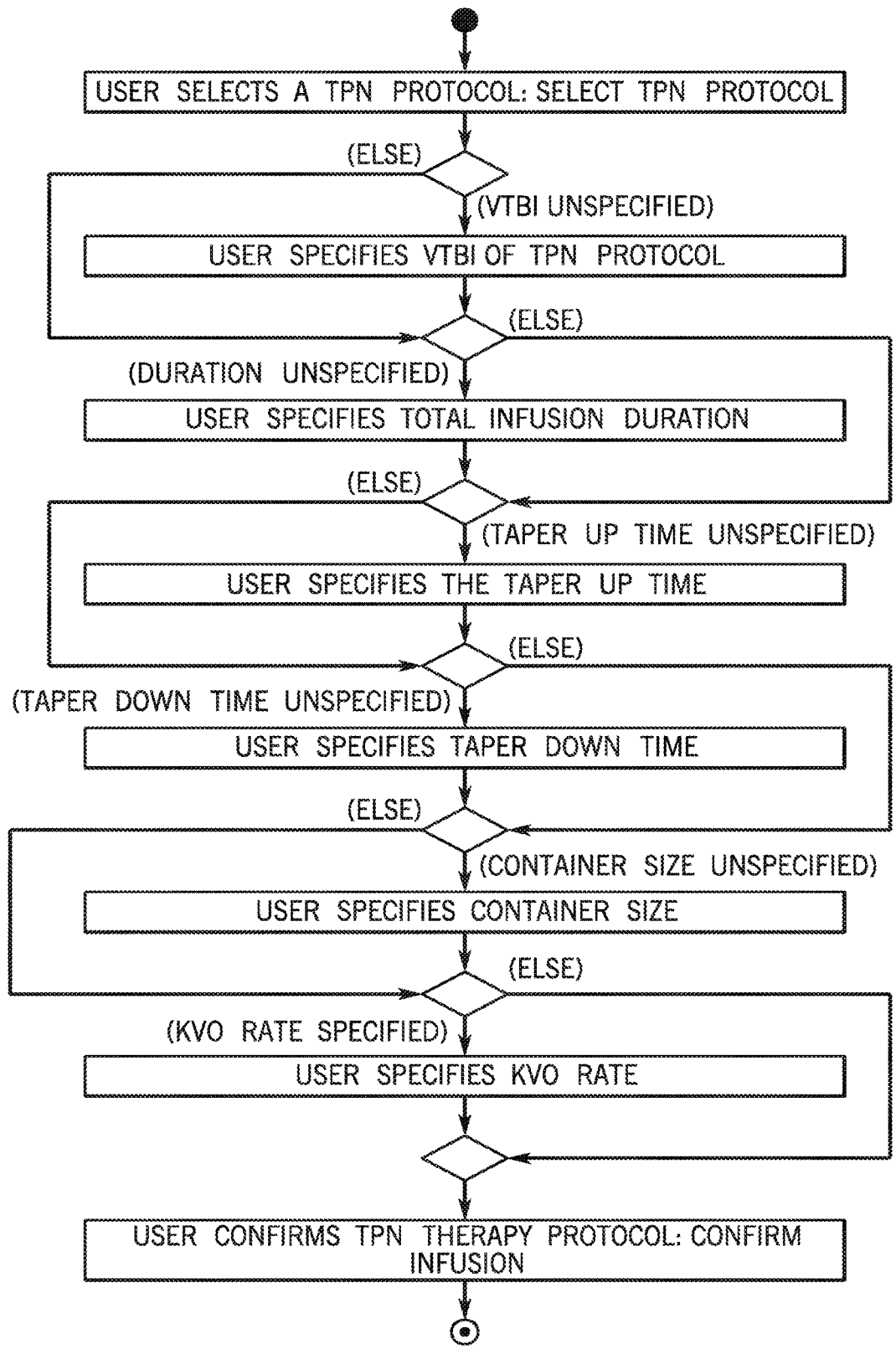
FIG. 45 depicts a flowchart of example method steps for configuring a TPN infusion at an infusion device.

FIG. 45 depicts a flowchart of example method steps for configuring a TPN infusion at an infusion device. As seen in FIG. 45, the caregiver may select a desired TPN protocol at the infusion device. Similar to the duplicate safety check for the substances delivered the patient, the infusion device may perform a duplicate safety check for the protocol selected. In particular, the infusion device may compare the selected TPN protocol to other TPN protocols that have been configured for the patient at the current infusion device or at other infusion devices associated with the patient. The safety checks may also include duplicate and compatibility safety checks for the substances delivered to the patient during the respective TPN protocols. In addition, if not already specified via the selected TPN protocol, the caregiver may select or specify a VTBI, total infusion duration, taper up time, taper down time, delivery source volume, and KVO rate for the selected TPN protocol. These parameters may be pre-populated based on the TPN protocol specified. The caregiver may also modify the pre-populated parameters at the infusion device. Once the selected protocol has been configured, the caregiver may confirm the selected parameters and initiate the TPN infusion.

Figure 46:
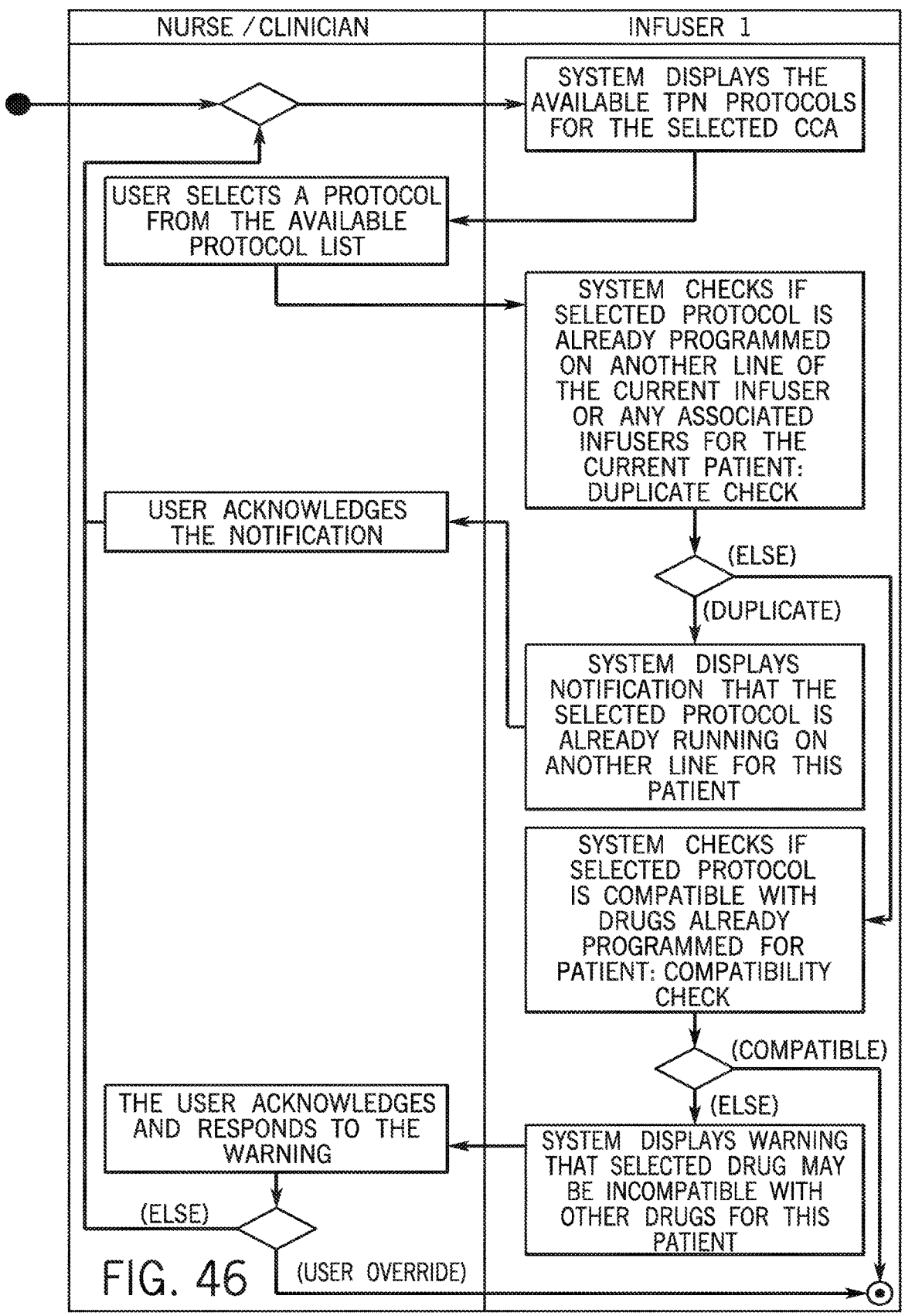
FIG. 46 depicts a flowchart of example method steps for selecting a TPN protocol at an infusion device.

FIG. 46 depicts a flowchart of example method steps for selecting a TPN protocol at an infusion device. As seen in FIG. 46, the infusion device displays the TPN protocols available for selection, and the caregiver may select one of the TPN protocols displayed. The infusion device may then determine whether the selected protocol has already been configured at the current infusion device or another infusion device associated with the patient. If so, the infusion device may display a notification to the caregiver indicating that the selected TPN protocol is (or may be) a duplicate TPN protocol currently being delivered or scheduled for delivery to the patient. The caregiver may acknowledge the notification indicating the potentially duplicate TPN protocol. The infusion device may also determine whether the selected TPN protocol is compatible with substances currently being delivered or scheduled to be delivered to the patient. The infusion device may notify or warn the caregiver when it determines that the TPN protocol is (or may be) incompatible with the substances considered. The caregiver may likewise acknowledge the notification or warning and respond accordingly. The caregiver may, for example, select to override the potential incompatibility and continue with the selected TPN protocol.

Figure 47:
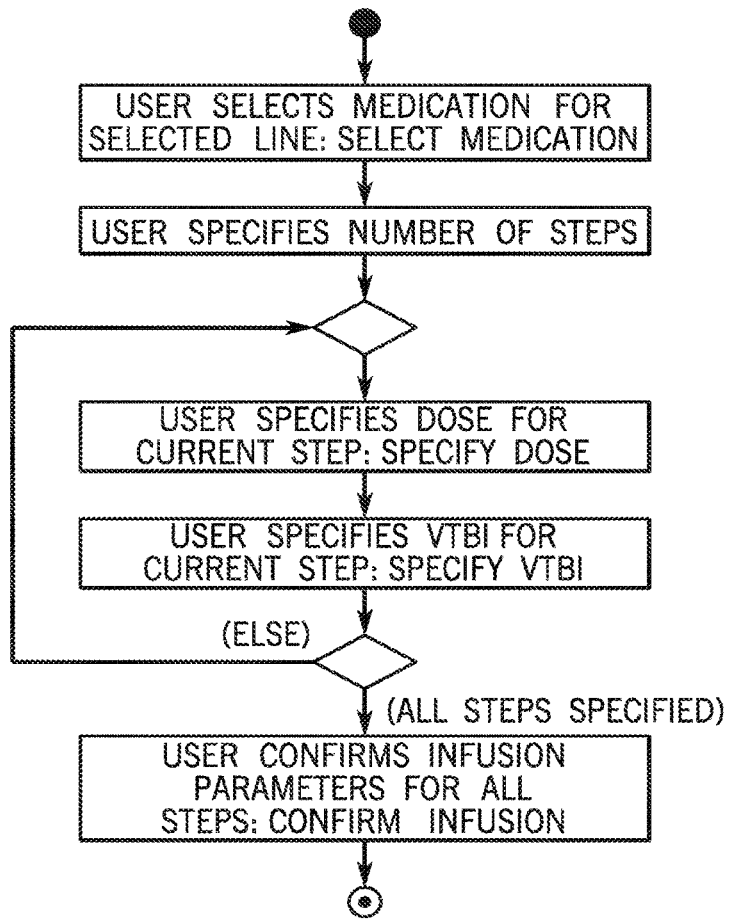
FIG. 47 depicts a flowchart of example method steps for configuring a multi-step infusion at an infusion device.

FIG. 47 depicts a flowchart of example method steps for configuring a multi-step infusion at an infusion device. As seen in FIG. 47, the caregiver may select the substance to be delivered to the patient as well as the total number of infusion steps to perform. For each infusion step, the caregiver may specify the dose and VTBI for the infusion step. Once the caregiver has configured the parameters for all of the infusion steps for the multi-step infusion, the caregiver may confirm and initiate the multi-step infusion.

Figure 48:
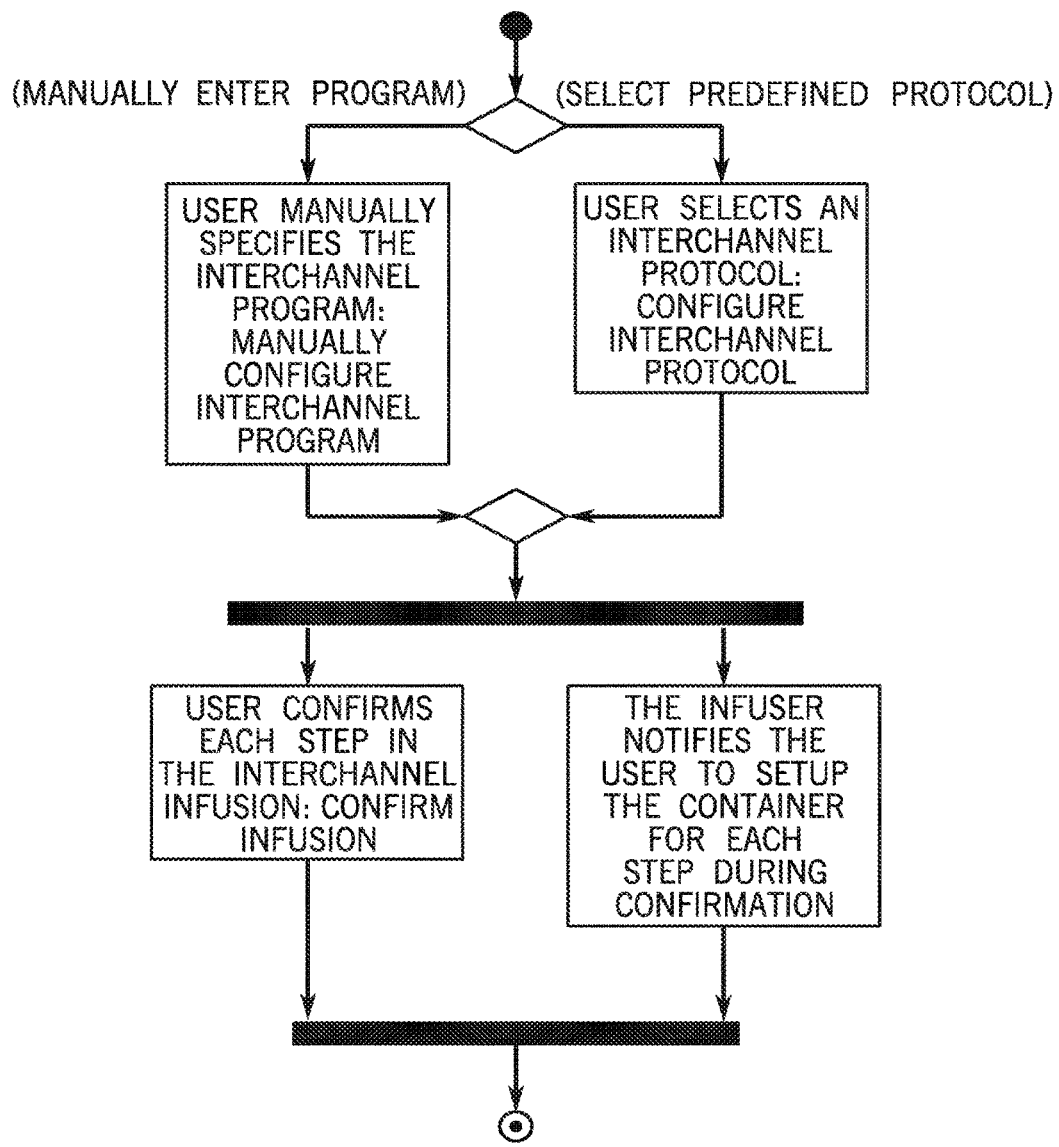
FIG. 48 depicts a flowchart of example method steps for configuring an inter-channel sequencing infusion.

FIGS. 48-55 depict example user interfaces and flowcharts of example method steps for configuring an inter-channel sequencing infusion. FIG. 48 depicts a flowchart of example method steps for configuring an inter-channel sequencing infusion. As seen in FIG. 48, caregiver may configure an inter-channel sequencing infusion by selecting a pre-defined protocol from a library of protocols or manually configure each infusion step of the inter-channel sequencing infusion. As also seen in FIG. 48, the infusion device may request confirmation from the caregiver of each step in the inter-channel sequencing infusion. During confirmation of each infusion step, the infusion device may also prompt the caregiver to set up the delivery source for the infusion step being confirmed.

Figure 49:
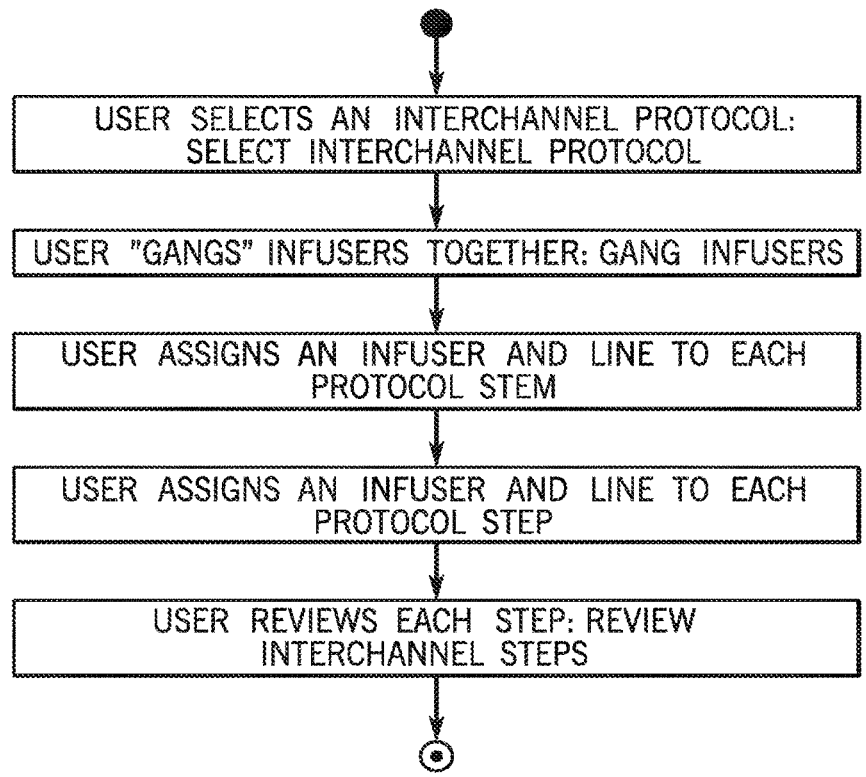
FIG. 49 depicts a flowchart of example method steps for selecting a pre-defined inter-channel sequencing protocol.

FIG. 49 depicts a flowchart of example method steps for selecting a pre-defined inter-channel sequencing protocol. As seen in FIG. 49, the caregiver may select an inter-channel sequencing protocol to deliver to the patient. The caregiver may also gang multiple infusion devices together to deliver the inter-channel sequencing infusion. The caregiver may assign one or more of the infusion steps of the selected protocol to individual infusion devices ganged together. Once the infusion steps for the inter-channel sequencing protocol have been configured and assigned to respective infusion devices, the caregiver may confirm and initiate the inter-channel sequencing infusion.

Figure 50:
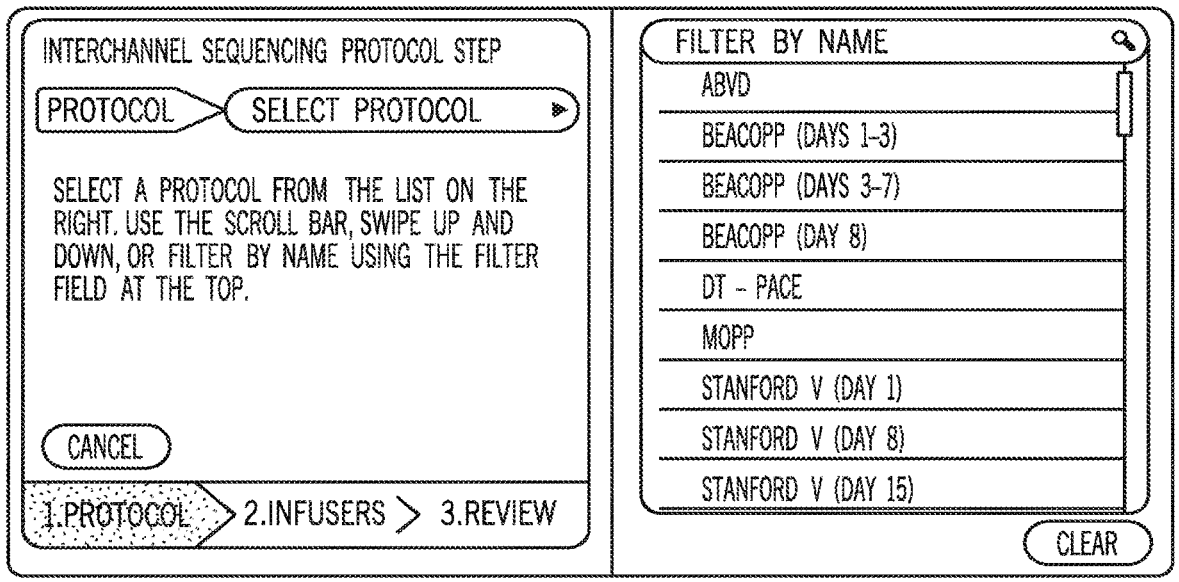
FIG. 50 depicts an example user interface for selecting an inter-channel sequencing protocol at an infusion device.

FIG. 50 depicts an example user interface for selecting an inter-channel sequencing protocol at an infusion device. As seen in FIG. 50, the infusion device may display a list of inter-channel sequencing protocols available for selection. The caregiver may select one of the protocols from the list, and the user interface may subsequently display an interface for selecting the ganged together infusion devices to perform the selected protocol and an interface for confirming the parameters configured for the selected protocol.

Figure 51:
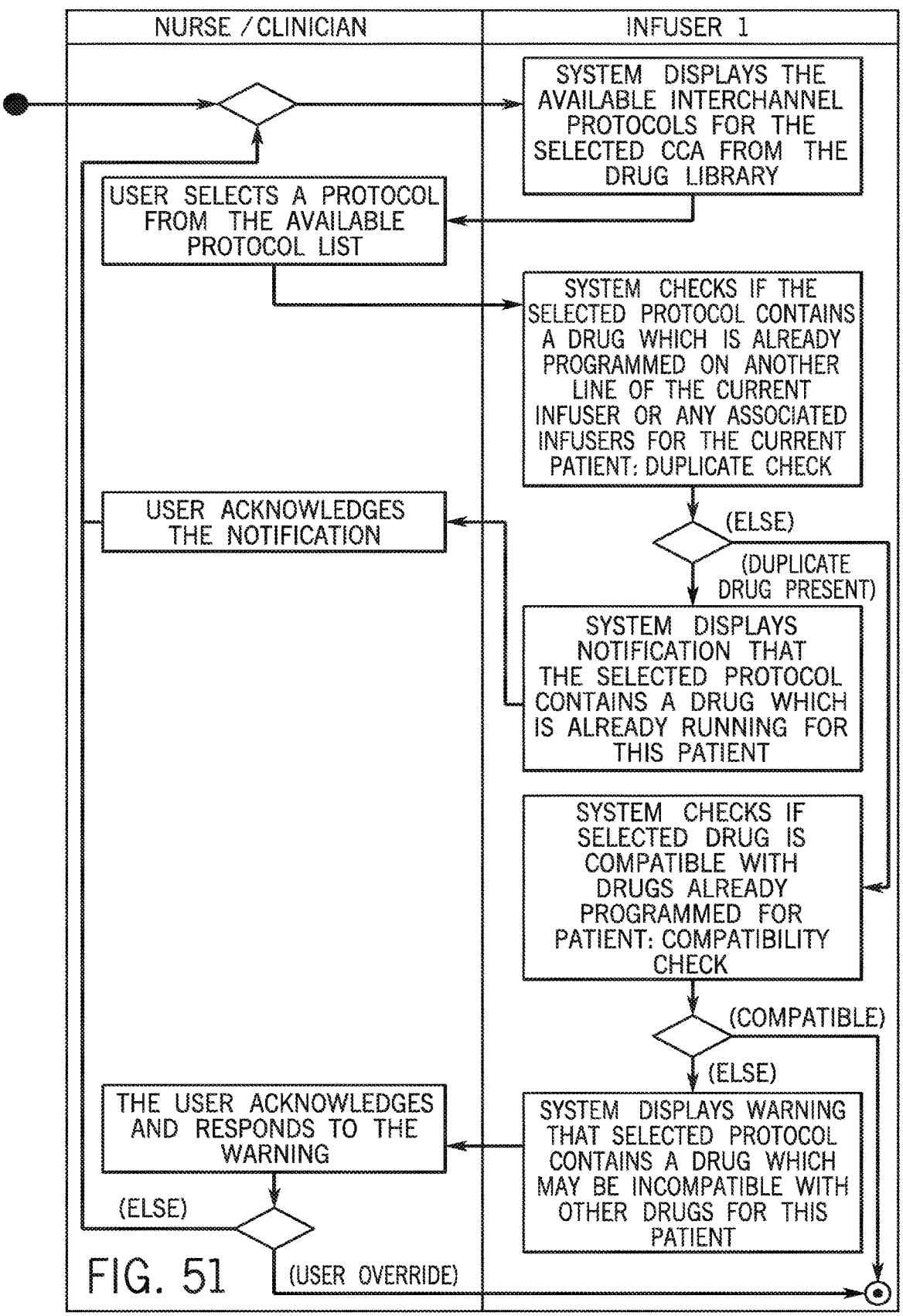
FIG. 51 depicts a flowchart of example method steps for performing safety checks based on a selected inter-channel sequencing protocol.

Like the other advanced infusion types, the infusion device may perform safety checks based on the selected inter-channel sequencing protocol. FIG. 51 depicts a flowchart of example method steps for performing safety checks based on a selected inter-channel sequencing protocol. Like the safety checks discussed above, the safety checks may include a duplicate safety check and a compatibility safety check to check whether any duplicate or incompatible substances are being delivered or are scheduled to be delivered to the patient during the inter-channel sequencing infusion. The infusion device may similarly notify or warn the caregiver if the infusion device identifies any duplicate or incompatible substances. The caregiver may also likewise acknowledge and override the notification or warning.

As noted above, inter-channel sequencing infusion may involve multiple infusion devices. An infusion device may allow a caregiver to identify and gang together additional infusion devices to be utilized during an inter-channel sequencing infusion. The process of ganging infusion devices together will be discussed in further detail below.

Figures 52, 53:
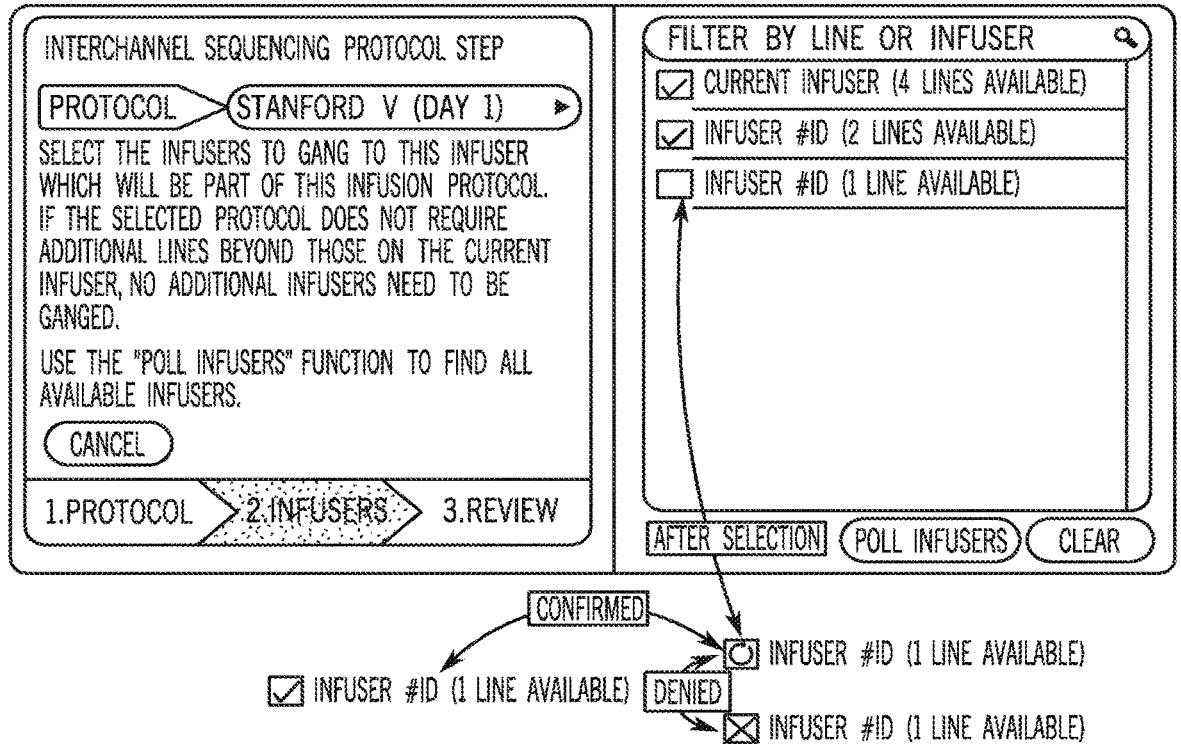
FIG. 52 depicts an example user interface of an infusion device for listing and selecting infusion devices to be used in an inter-channel sequencing infusion.
FIG. 53 depicts an example user interface of an infusion device displaying a confirmation request to gang the infusion device to another infusion device.

FIG. 52, however, depicts an example user interface of an infusion device for listing and selecting infusion devices to be used in an inter-channel sequencing infusion. As seen in FIG. 52, the user interface displays a list of infusion devices in signal communication with the current infusion device that may be ganged together for the inter-channel sequencing infusion. The list of infusion devices may include a unique identifier for the available infusion devices and the total number of lines available at each of the infusion devices. The caregiver may select one or more of the available infusion devices from the list to include in the inter-channel sequencing infusion currently being configured at the infusion device. As also seen in FIG. 52, the user interface includes a button to poll infusion devices (e.g., wirelessly) that are nearby the current infusion device.

Polling nearby infusion devices will be discussed in further detail below. Upon selection of one of the available infusion devices, a notification may be transmitted to the selected infusion device that the caregiver has selected it to be ganged to the current infusion device. Upon receipt of the notification, the selected infusion device may display a confirmation request. FIG. 53 depicts an example user interface of an infusion device displaying a confirmation request to gang the infusion device to another infusion device. As seen in FIG. 53, the confirmation request includes the respective identifiers for the infusion devices and buttons allowing the caregiver to confirm or deny the request. The user interface in FIG. 52 also depicts how the list of available infusion devices is updated upon the confirmation or denial of a request to gang a selected infusion device to the current infusion device.

For an inter-channel sequencing infusion, one of the infusion devices may be designated the master infusion device and the other infusion devices may be designated the slave infusion devices. The infusion device at which the caregiver configures the inter-channel sequencing infusion and adds additional infusion devices to the inter-channel sequencing infusion may be designated as the master infusion device for the infusion. The additional infusion devices added to the inter-channel sequencing infusion may be designated as the slave infusion devices. The notification sent to a selected infusion device from the master infusion device may be sent via a medication management system the infusion devices are connected to. Additionally or alternatively, the notification sent to a selected infusion device from the master infusion device may be sent via a direct wired or wireless communication between the master infusion device and the slave infusion device. Similarly, the response to the confirmation request (e.g., confirmed or denied) may be sent back to the master infusion device from the selected infusion device via a medication management system or via a direct wired or wireless communication between the infusion devices.

The master infusion device may also be configured to confirm that the number of infusion devices needed to carry out the inter-channel sequencing infusion have been ganged together. As one example, the total number of infusion lines may be required to match the total number of unique substances selected to be delivered to the patient, and the master infusion device may be configured to confirm that enough infusion devices have been ganged together to provide the total number of infusion lines needed. If the caregiver attempts to proceed to the review screen without having selected the number of infusion devices needed to carry-out the inter-channel sequencing infusion, the infusion device may display a notification that additional infusion devices are needed. In some example implementations, a "review" button may be inactive until the caregiver has selected enough infusion devices.

Figure 54:
FIG. 54 depicts a user interface of an infusion device for assigning infusion lines to steps of an inter-channel sequencing infusion.

Once the caregiver has selected enough infusion devices for the inter-channel sequencing infusion, the infusion device may prompt the caregiver to respectively assign an infusion line to each step in the infusion. FIG. 54 depicts a user interface of an infusion device for assigning infusion lines to steps of an inter-channel sequencing infusion. As seen in FIG. 54, the user interface displays the details of the currently selected step of the inter-channel sequencing infusion including, e.g., the substance to be delivered, the dose, and the VTBI. The user interface also displays a list of the infusion devices that have been ganged together for the inter-channel sequencing infusion. The caregiver may select one of the infusion devices, and the user interface may display the lines of the selected infusion device that are available to be assigned to the current step. The caregiver may proceed through the steps of the inter-channel sequencing infusion and select a line to be assigned to each respective step. The user interface may deactivate (e.g., gray out) or hide selections for lines of infusion devices that have already been assigned to an infusion step. The user interface may also deactivate or hide selections of infusion devices that have no lines remaining to be assigned to an infusion step. In some implementations, the infusion device may allow the caregiver to associate an infusion device and line when an infusion device is selected for the inter-channel sequencing infusion.

Figure 55:
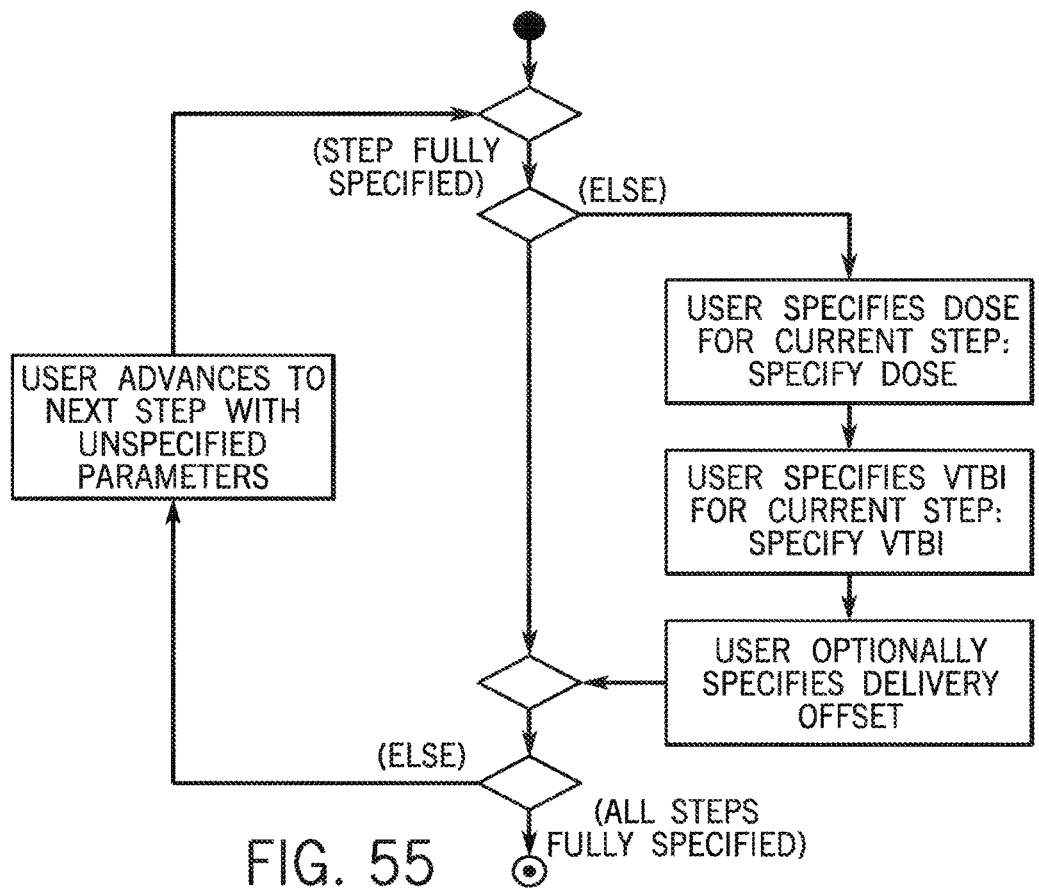
FIG. 55 depicts a flowchart of example method steps for configuring the steps of an inter-channel sequencing infusion.

As noted above, the caregiver may specify the parameters for each step in an inter-channel sequencing infusion as the infusion steps are added to the sequence. FIG. 55 depicts a flowchart of example method steps for configuring the steps of an inter-channel sequencing infusion. As seen in FIG. 55, the caregiver may select or specify, for each step, a dose, VTBI, and delay offset. Once the step is fully specified, the caregiver may proceed to the next step in order to specify the parameters for that step. The delay offset may be an optional parameter. Once all steps are configured, the caregiver may review the steps of the inter-channel sequencing infusion and initiate the infusion at the infusion device. During the review and confirmation process, the infusion device may remind the caregiver to ensure the delivery sources have been setup and connected to the infusion devices.

Figure 56A:
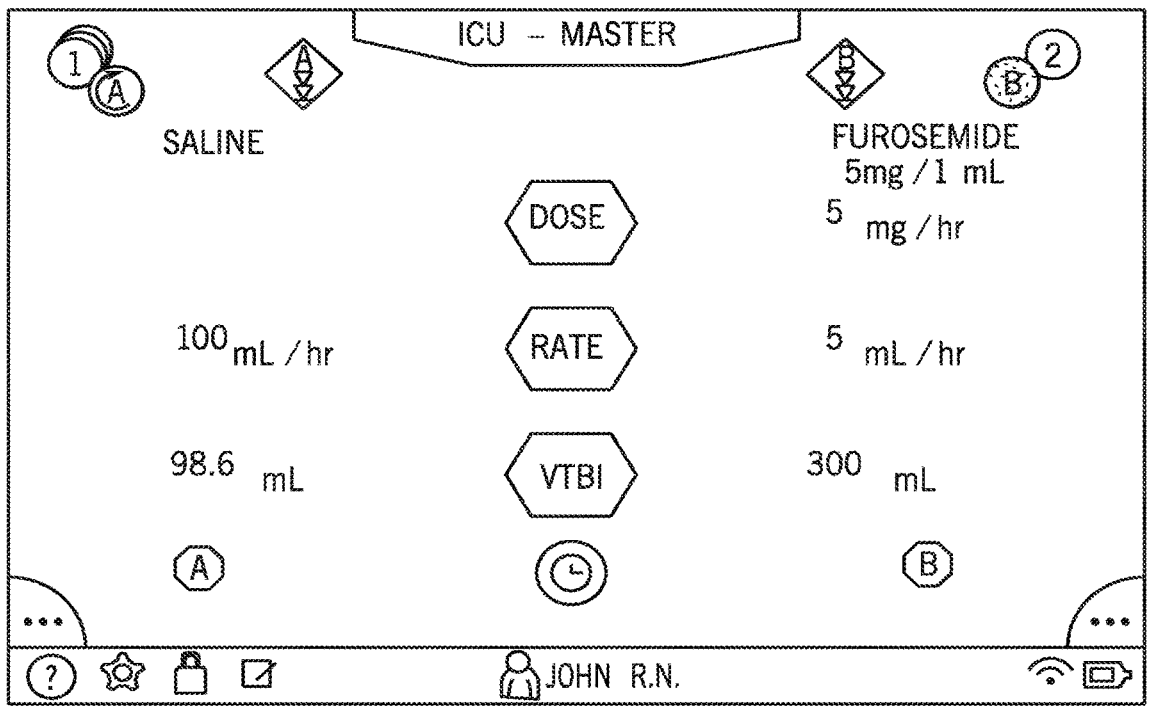
FIG. 56A depicts a user interfaces that include a visual indicator to identify the infusion device as a master or slave infusion device.
Figure 56B:
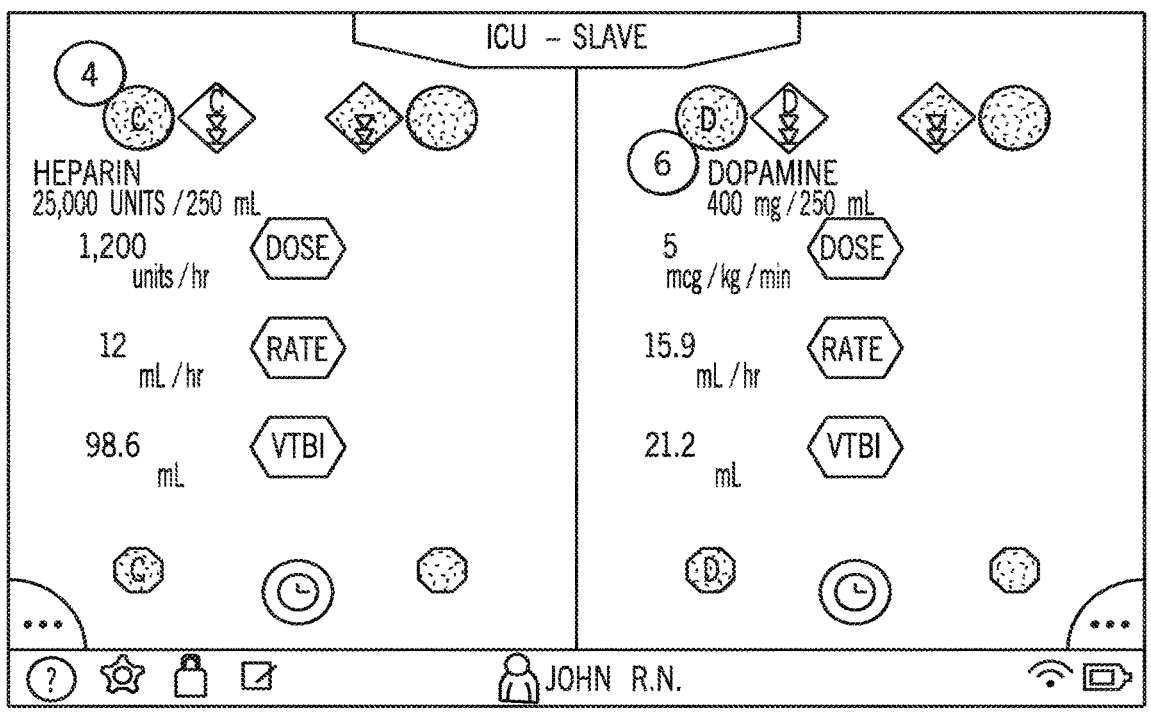
FIG. 56B depicts another user interfaces that include a visual indicator to identify the infusion device as a master or slave infusion device.

During the inter-channel sequencing infusion, the infusion devices may provide a visual indication to indicate their status as either the master infusion device or one of the slave infusion devices. FIG. 56A-B depict respective user interfaces that include a visual indicator to identify the infusion device as a master or slave infusion device. As seen in FIG. 56A, the user interface of the infusion device includes a dark-colored background (e.g., dark blue) to identify the infusion device as the master infusion device. As seen in FIG. 56B, the user interface of the infusion device includes a light-colored background (e.g., light green) to identify the infusion device as a slave infusion device. Additional and alternative types of visual indicators may be selectively employed to visually distinguish master and slave infusion devices.

Figure 57:
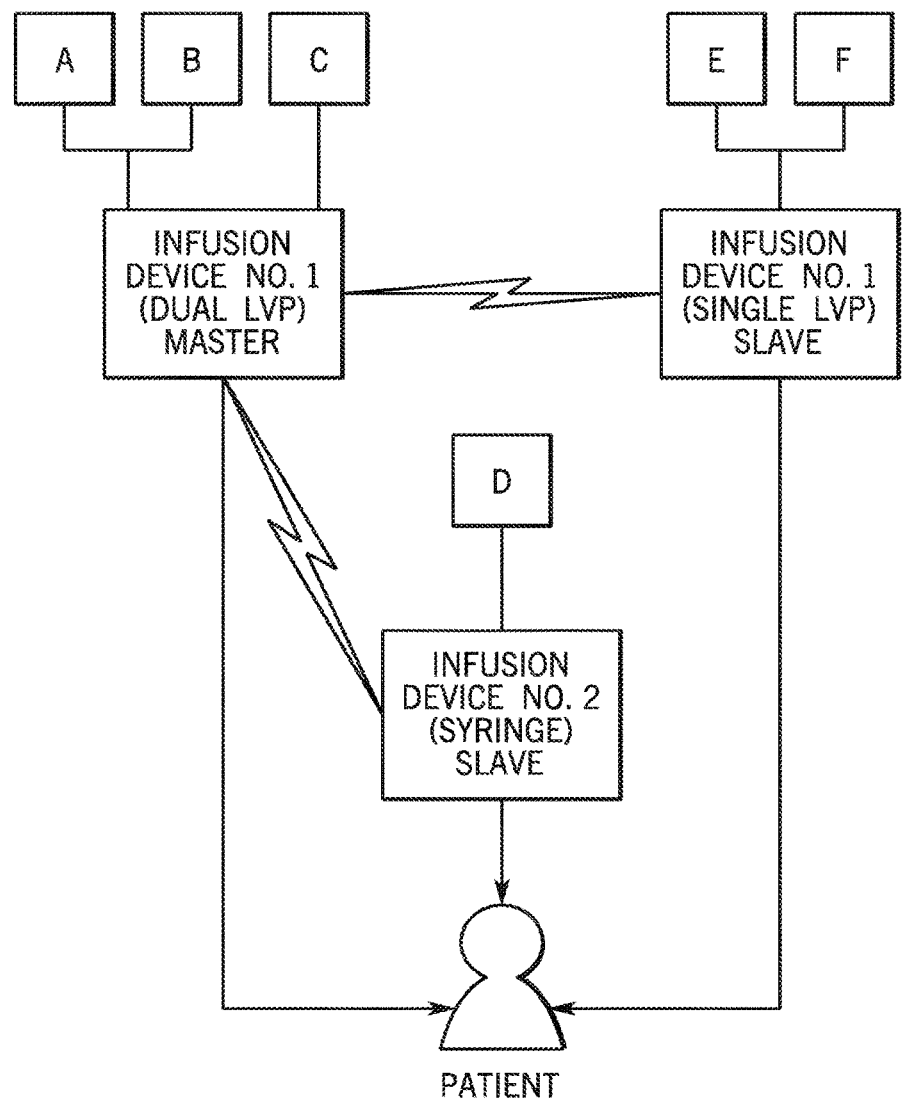
FIG. 57 depicts an example of a possible inter-channel sequencing infusion that may be implemented utilizing the infusion devices described herein.

FIG. 57 depicts an example of a possible inter-channel sequencing infusion that may be implemented utilizing the infusion devices described herein. As seen in FIG. 57, three infusion devices are connected to a patient: a first dual LVP infusion device connected to three delivery sources (A, B, and, C); a second syringe infusion device connected to one delivery source (D); and a third single LVP infusion device connected to two delivery sources (E and F). As also seen in FIG. 57, the dual LVP infusion device has been designated the master infusion device while the syringe infusion device and the single LVP infusion device have been designated slave infusion devices. The master infusion device in FIG. 57 is in signal communication with the slave communication devices via wireless communications. An example inter-channel sequencing infusion performed by the infusion devices in FIG. 57 may be, for example: flush from delivery source A; infuse from delivery source B; flush from delivery source A; infuse from delivery sources C and D together; flush from delivery source A; deliver from delivery source E; flush from delivery source A; deliver from delivery source F; and flush from delivery source A. In some example implementations, the each of the delivery sources may be connected to a manifold (e.g., an omni-flow manifold), and the manifold may be connected to an infusion device to infuse the patient from all of the delivery sources via a single channel.

Figure 58:
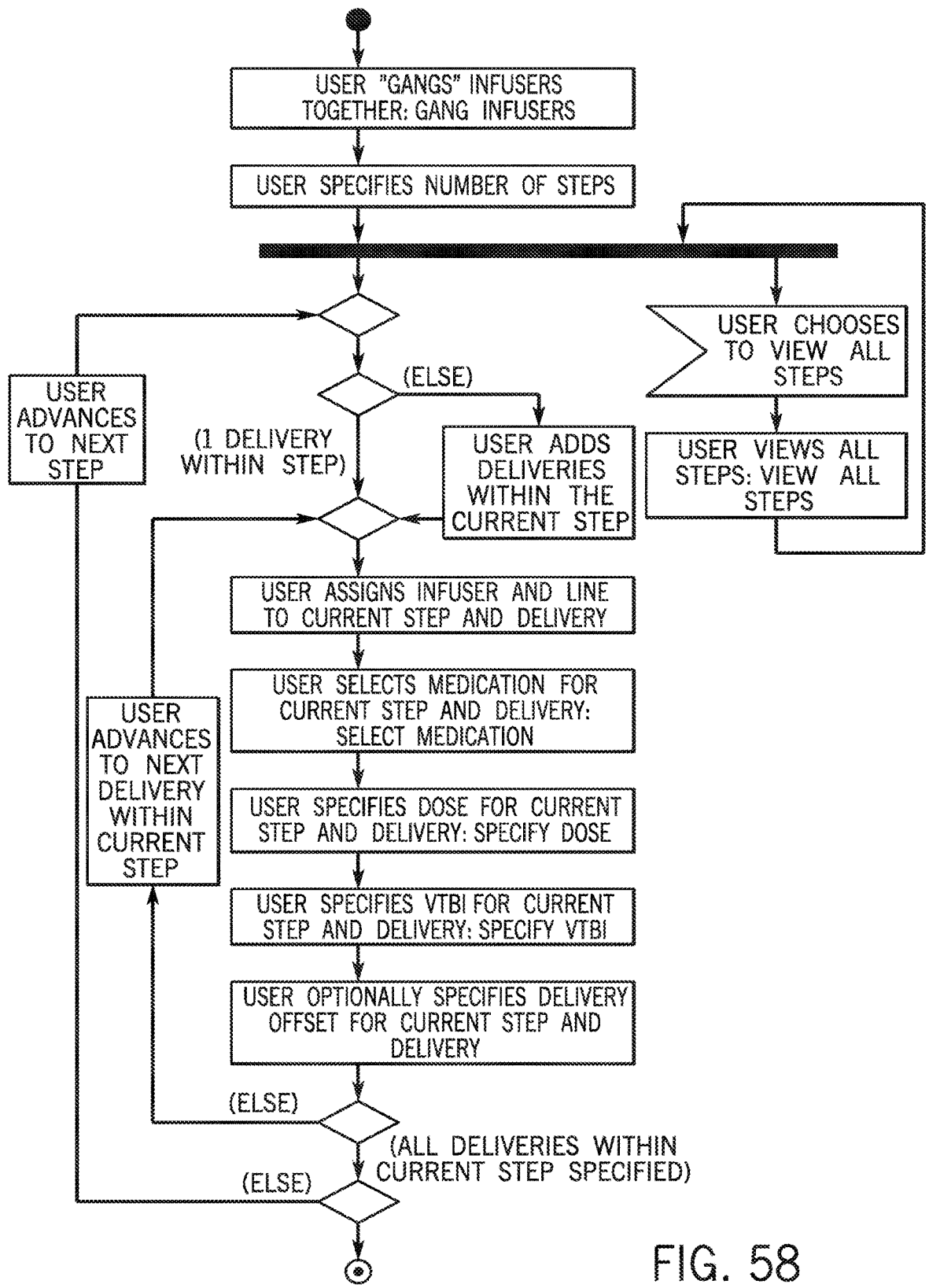
FIG. 58 depicts a flowchart of example method steps for configuring the steps of an inter-channel sequencing infusion manually.

As noted above, a caregiver may also manually configure an inter-channel sequencing infusion rather than select from a list of predefined protocols. FIG. 58 depicts a flowchart of example method steps for configuring the steps of an inter-channel sequencing infusion manually. As seen in FIG. 58, the caregiver may select one or more infusion devices to utilize for the inter-channel sequencing infusion. The caregiver may select the infusion devices to use as described above. Having selected the infusion devices, the caregiver may specify the total number of steps to be performed for the inter-channel sequencing infusion. The caregiver may configure an infusion step to include one or more deliveries to the patient. For each step, and for each delivery in a step, the caregiver may assign an infusion device and line to the current step and the current delivery of that step. The caregiver may also select or specify, for the current delivery of the current step, the substance to be delivered to the patient, the dose, and the VTBI. The caregiver may also specify a delay offset. The caregiver may repeat these actions for each delivery of the current step. Once all deliveries of the current step have been configured, the caregiver may proceed to the next step in the infusion sequence and likewise configure each delivery for the next infusion step selected. The caregiver may also view at the infusion device all steps of the inter-channel sequencing infusion, review the steps, and initiate the infusion.

Figures 59, 60:
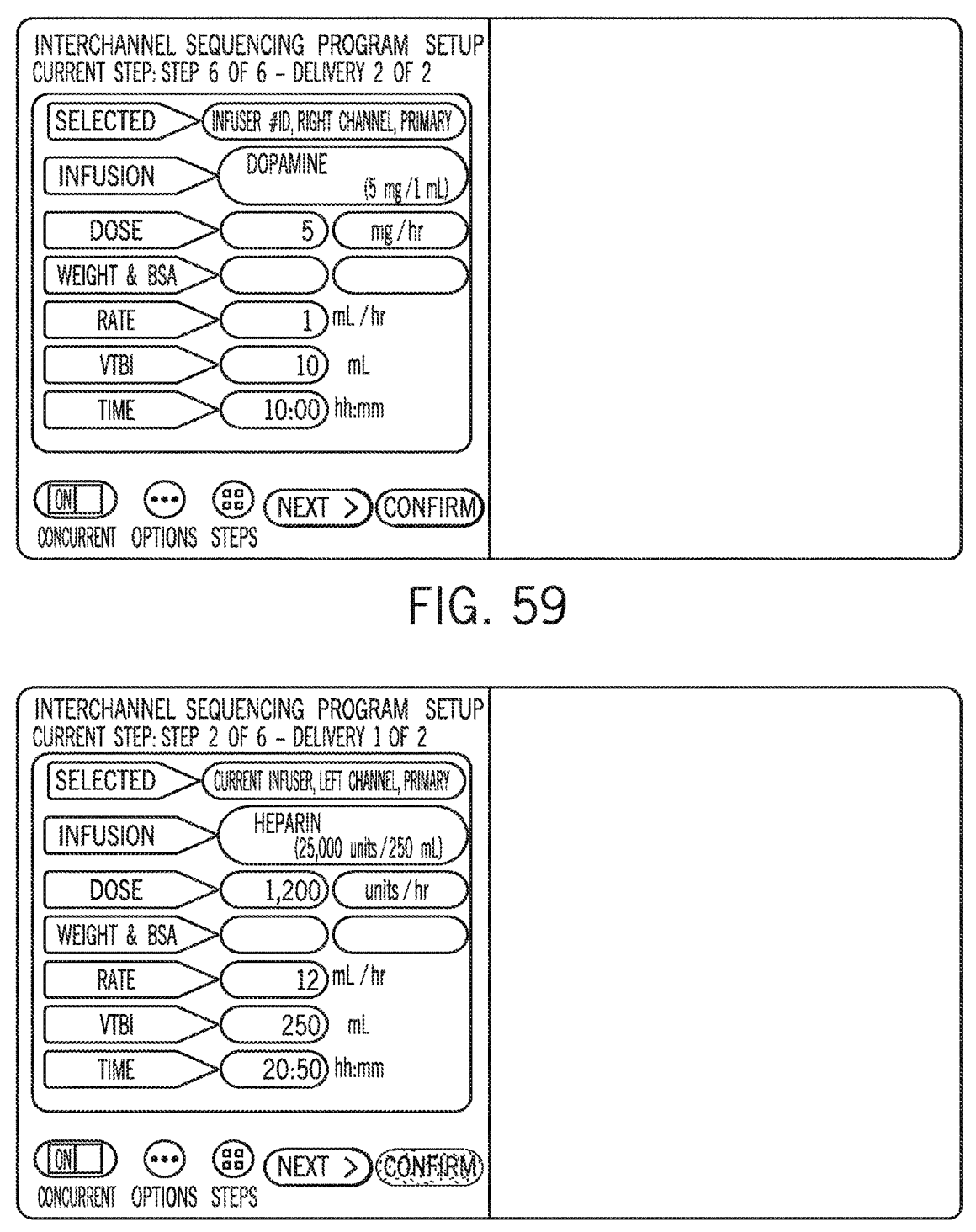

FIGS. 59-60 depict example user interfaces of an infusion device for configuring the steps of an inter-channel sequencing infusion. FIG. 59 depicts a user interface for configuring the first delivery of the second step of an inter-channel sequencing infusion. As seen in FIG. 59, the user interface displays the selected infusion and line, the substance to be delivered to the patient and its concentration, the dose and units, the weight/BSA, the delivery rate, the VTBI, and the total delivery duration. The user interface in FIG. 59 also includes a button to specify whether or not the current delivery should be delivered concurrent with the other deliveries of the current step. The user interface in FIG. 59 additionally includes buttons to configure options for the current delivery of the current step (e.g., a delay offset), view all the steps of the infusion, confirm the parameters set for the current delivery of the current step, and advanced to the next delivery or step of the infusion. As described above, the multi-step view may allow that caregiver to select steps and deliveries, rearrange steps and deliveries, or delete steps and deliveries. The user interface in FIG. 60 includes similar information for the second delivery of the sixth step in the infusion sequence. As seen in FIG. 60, the user interface includes the unique identifier of the infusion device that has been assigned to the current step.

Interconnected Infusion Devices

As noted above, the infusion devices described herein may include communication modules that allow infusion devices to interconnect with one another for inter-channel and inter-device sequencing for infusion procedures. The communication modules may thus facilitate device-to-device communications as well as communications between infusion devices via a medication management system. Communications between infusion devices may be wired or wireless, via an MMS, or via an interconnecting device such as, e.g., a backplane, rack, or dock. Communication between infusion devices may also enable infusions between different types of infusion devices (e.g., LVP, syringe, and PCA infusion device types) as well as inter-channel sequencing programs in which multiple deliveries are infused within one step. Moreover communications between infusion devices may advantageously permit the use of pre-programmed inter-channel sequencing protocols for infusions to a patient.

Figure 65:
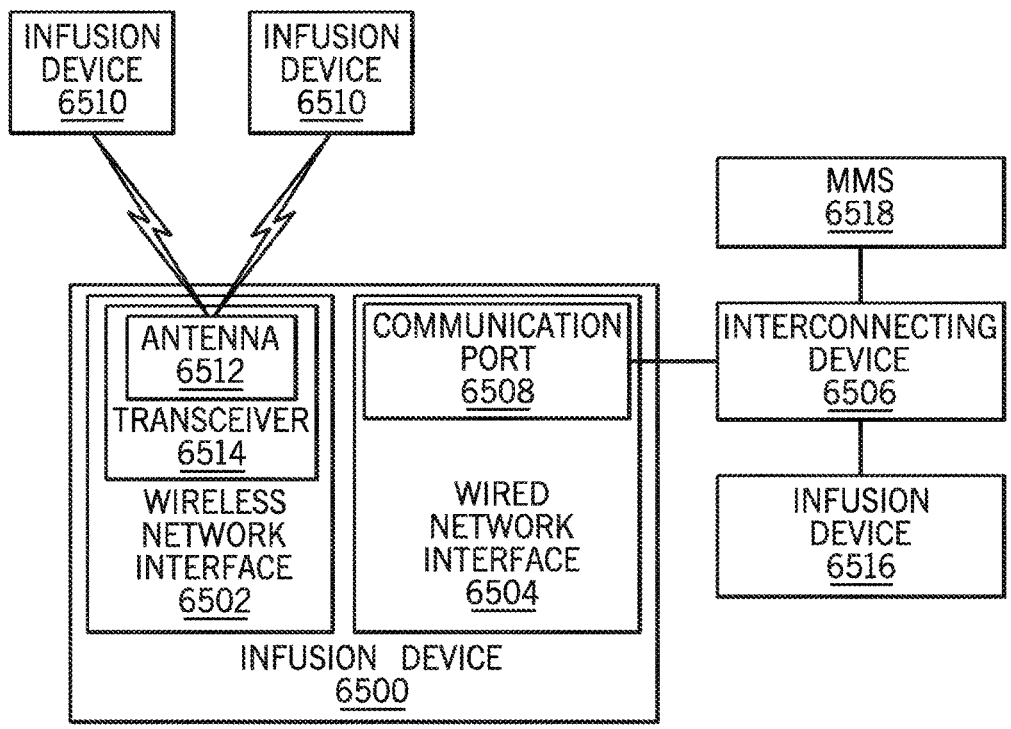
FIG. 65 depicts an example of an implementation of an infusion device.

FIG. 65, depicts an example of an implementation of an infusion device 6500 is shown. The infusion device 6500, in this example, includes a wireless network interface 6502 and a wired network interface 6504. The infusion device 6500 may be in signal communication with an interconnecting device 6506 via a communication port 6508 of the wired network interface 6504. The infusion device 6500 may also be in signal communication with one or more infusion devices 6510 via an antenna 6512 of a transceiver 6514 of the wireless network interface 6502. Through the interconnecting device 6506, the infusion device 6500 may be in signal communication with another infusion device 6516 as well as a medication management system 6518. The infusion device 6500 may also be in signal communication with the MMS 6518 via the wireless network interface 6502.

The interconnecting device 6506 may be, e.g., a wired backplane, dock, or rack that mounts or otherwise supports multiple infusion devices. The multiple infusion devices mounted at the interconnecting device may be housed in a common housing. The interconnecting device 6506 may be configured such that one of the infusion devices mounted at the interconnecting may be considered to be a lead infusion device. As an example, in an interconnecting device in which infusion devices are mounted from top-to-bottom, the lead infusion device may be the top-most infusion device. As another example, in an interconnecting device in which infusion devices are mounted from left-to-right, the lead infusion device may be the left-most infusion device. Additional examples will be appreciated with the benefit of this disclosure. The subsequent infusion devices may be subordinate to the lead infusion device based on their position at the interconnecting device in the sequence of infusion devices. For example, the next leading infusion device may be the infusion device just below the top-most infusion device or just to the right of the left-most infusion device and so forth.

The wireless network interface 6502 may be configured to exchange wireless communications with other infusion devices or an MMS using one or more wireless communication protocols. Example of suitable wireless communications protocols include radio-frequency identification (RFID) protocols, one or more of the IEEE 802.11 protocols (e.g., 802.11a, 802.11b, 802.11g, 802.11n), Bluetooth protocols, and other wireless communication protocols suitable for interconnecting infusion devices.

Figure 66:
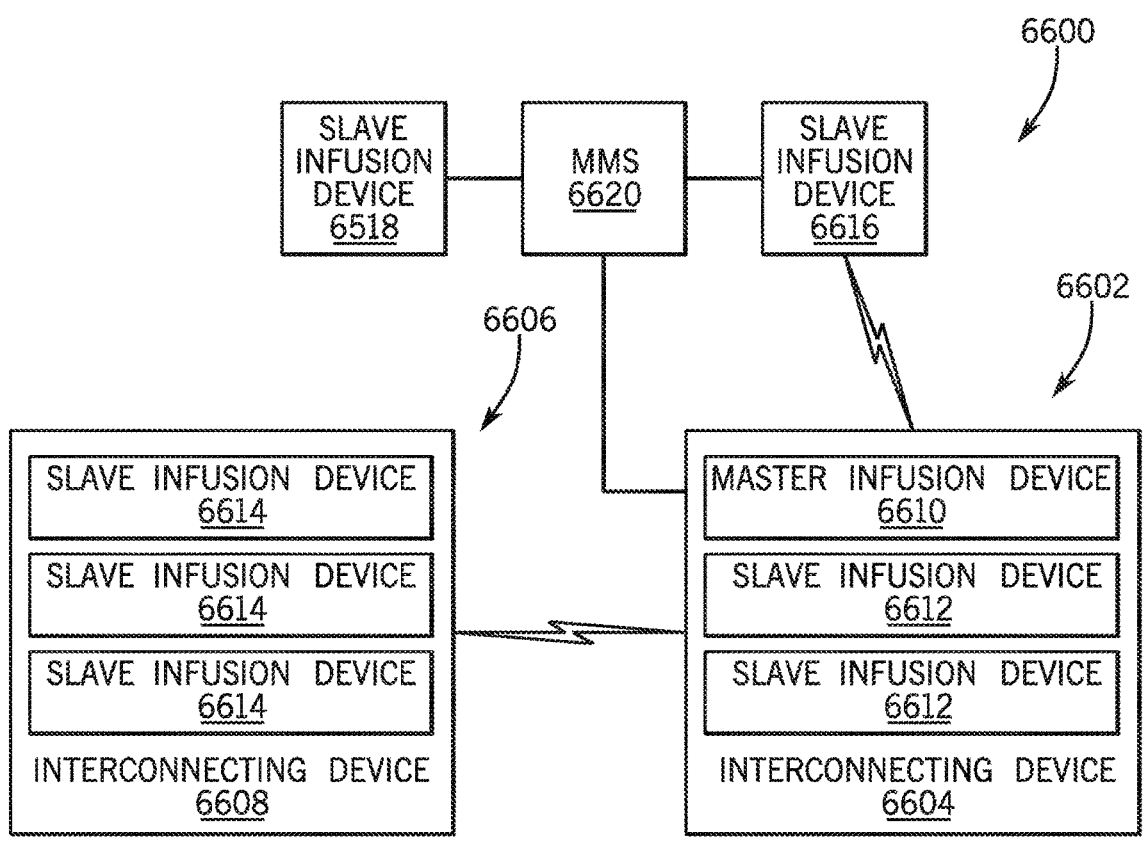
FIG. 66 depicts an example of a set of interconnected infusion devices.

FIG. 66 depicts an example of a set of interconnected infusion devices 6600. As seen in FIG. 66, a first set of infusion devices 6602 are mounted at a first interconnecting device 6604, and a second set of infusion devices 6606 are mounted at a second interconnecting device 6608. As also seen in FIG. 66, one of the infusion devices 6610 at the interconnecting device 6604 has been designated the master infusion device. The other infusion devices 6612 at the interconnecting device 6604 have been designated slave infusion device. In addition, the master infusion device 6610 is in wireless signal communication with the interconnecting device 6608. When wireless communication with infusion devices of an interconnecting device, the infusion devices mounted at that interconnecting device may be considered as a singular unit. In FIG. 66, each of the infusion devices 6614 at the interconnecting device 6608 have been designated slave infusion devices. The master infusion device 6610 is also in direct wireless signal communication with an infusion device 6616 that has been designated a slave infusion device as well as an infusion device 6618 via an MMS 6620. The infusion device 6618 interconnected to the master infusion device 6610 via the MMS 6620 has also been designated a slave infusion devices.

As described in further detail below, interconnected infusion devices may designate a master infusion device when an MMS is and is not present. Designating a master infusion device via an MMS will be discussed in further detail below. If an MMS is not present, however, interconnected infusion devices may designate a master infusion device based on whether the infusion devices are in signal communication wirelessly or via an interconnecting device. If interconnected via an interconnecting device, the infusion devices may designate the lead infusion device as the master infusion device (e.g., the top-most or left-most infusion device). If communication with the master infusion device is lost, then the infusion devices may designate a new master infusion device which may be the next infusion device subordinate to the master infusion device in the sequence of infusion devices (e.g., the next top-most or next left-most infusion device). If the infusion devices are interconnected wirelessly, then the infusion devices may designate the infusing device having the longest infusion duration as the master infusion device. If communication with the master infusion device is lost, then the infusion devices may designate the infusion device having the next longest infusion duration as the new master infusion device. Designating the master infusion device when an MMS is not present will also be discussed in further detail below.

Figure 67:
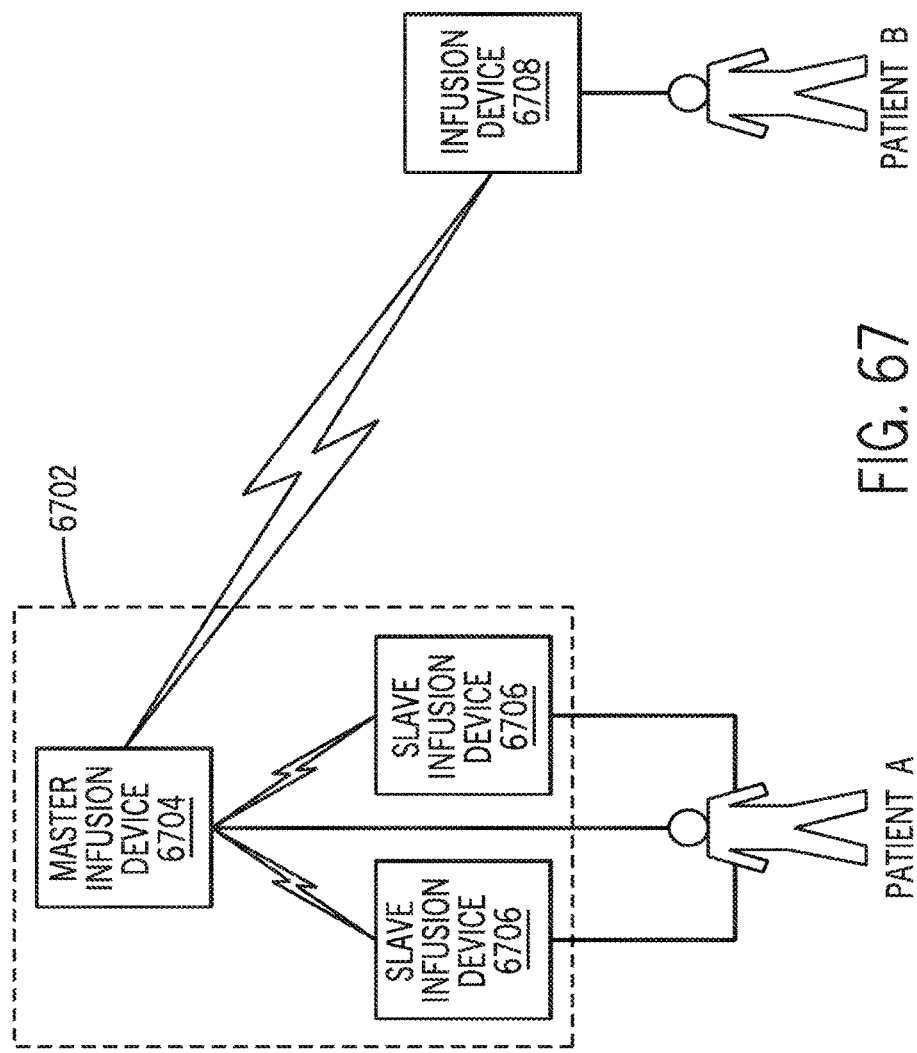
FIG. 67 depicts interconnected infusion devices respectively associated with patients.

FIG. 67 depicts interconnected infusion devices respectively associated with patients. As seen in FIG. 67, a set of ganged together infusion devices 6702 are associated with a first patient (Patient A). The ganged infusion devices 6704 and 6706 of the set of infusion devices 6702 are in wireless signal communication with each other. One of the infusion devices 6704 has been designated the master infusion device, and two of the infusion devices 6706 have been designated as slave infusion devices. Another infusion device 6708 is associated with another patient (Patient B). As seen in FIG. 67, the master infusion device 6704 may be in the vicinity of the other infusion device 6708 and thus in signal communication with the other infusion device. As explained in further detail below, however, the other infusion device 6708 may not be available to be ganged with the set of ganged infusion devices 6702 since it is associated with a different patient (i.e., Patient B vs. Patient A).

Figure 68:
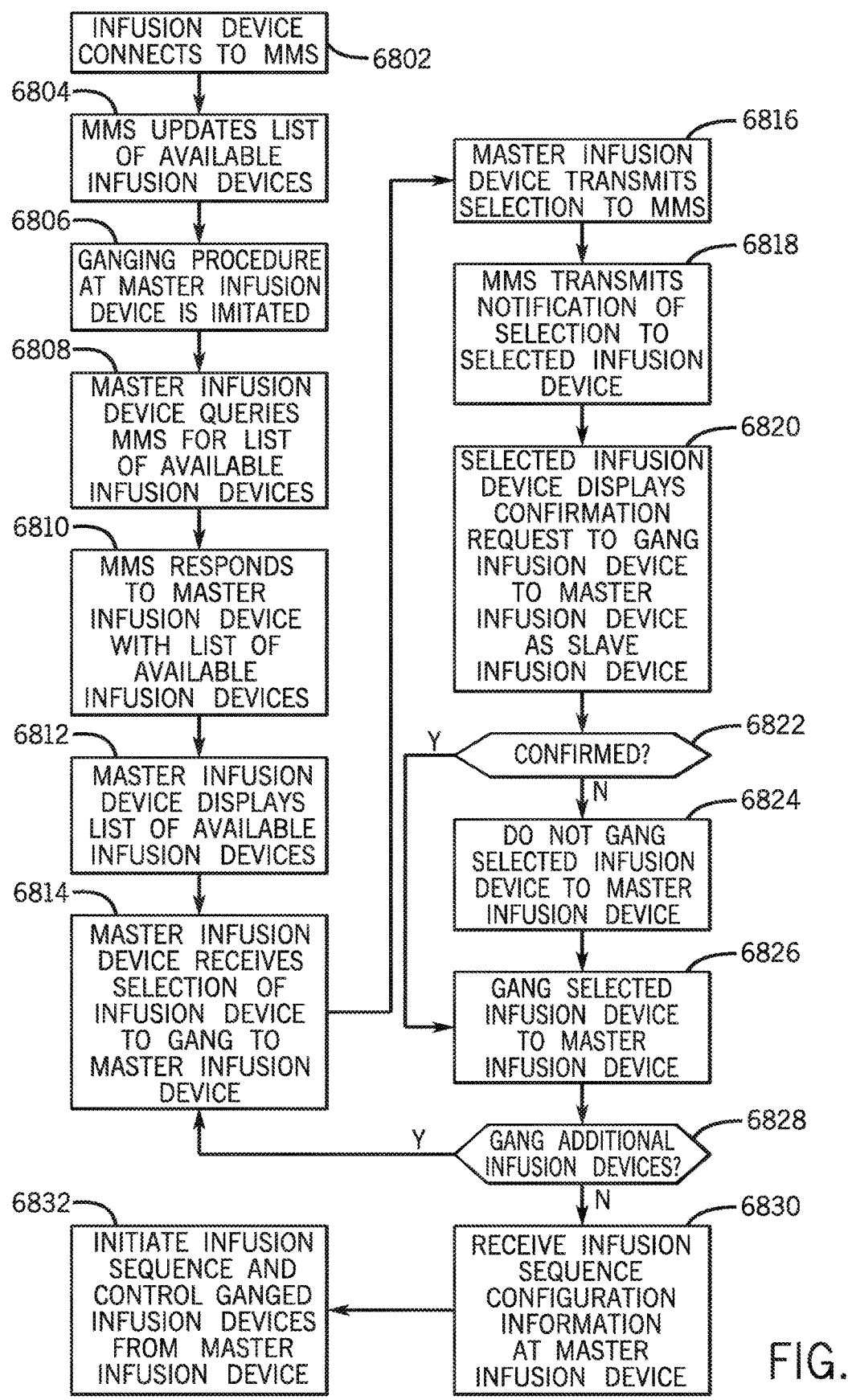
FIG. 68 depicts a flowchart of example method steps for ganging together infusion devices via a medication management system.

FIG. 68 depicts a flowchart of example method steps for ganging together infusion devices via a medication management system. An infusion device connects to an MMS (block 6802). In response to connecting to the infusion device, the MMS updates a list of infusion devices (block 6804). The list of infusion devices maintained at the MMS may identify the patient each infusion device is respectively associated with (e.g., using a unique identifier respectively associated with each patient). The MMS may also query an infusion device to determine which patient the infusion device is associated with. A caregiver initiates the ganging procedure at one of the infusion devices connected to the MMS (block 6806). The infusion device at which the ganging process is initiated may be designated as the master infusion device.

The master infusion device then queries the MMS for a list of infusion devices available to be ganged to the master infusion device (block 6808). In response to the query, the MMS responds to the master infusion device with the list of available infusion devices (block 6810). The MMS may generate the list of available infusion devices based on the patient the master infusion device is associated with. The list of available infusion devices may, for example, only include infusion devices currently associated with the patient or, additionally or alternatively, infusion devices that have not yet been assigned to a patient and thus available to be associated with the patient the master infusion device is associated with. The master infusion device displays the list of available infusion devices (block 6812), e.g., at a display screen for review by the caregiver. The master infusion device receives from the caregiver a selection of one of the available infusion devices to gang to the master infusion device (block 6814). The master infusion device then transmits the selection to the MMS (block 6816), and the MMS in turn transmits a notification of the selection to the selected infusion device (block 6818).

In response to receipt of the notification, the selected infusion device displays (e.g., at a display screen) a confirmation request for the caregiver to confirm the selected infusion device should be ganged to the master infusion device as a slave infusion device (block 6820). If the caregiver does not confirm that the selected infusion device should be ganged to the master infusion device (block 6822: N), then the selected infusion device is not ganged to the master infusion device (block 6924). If, however, the caregiver does confirm that the selected infusion device should be ganged to the master infusion device (block 6822: Y), then the selected infusion device is ganged to the master infusion device (block 6826). The caregiver may gang multiple infusion devices to the master infusion devices. Accordingly, if the caregiver wishes to gang additional infusion devices to the master infusion device (block 6828: Y), the caregiver may repeat the steps above to gang additional infusion devices to the master infusion device. If the caregiver does not wish to gang additional infusion devices to the master infusion device (block 6828: N), or once the caregiver has ganged the desired number of infusion devices to the master infusion device, the caregiver may provide the infusion sequence configuration information to the master infusion device (block 6830). Once the caregiver has configured and confirmed the inter-device infusion sequence, the caregiver may initiate the infusion sequence and the master infusion device controls the infusion sequence across the ganged infusion devices (block 6832).

Figure 69:
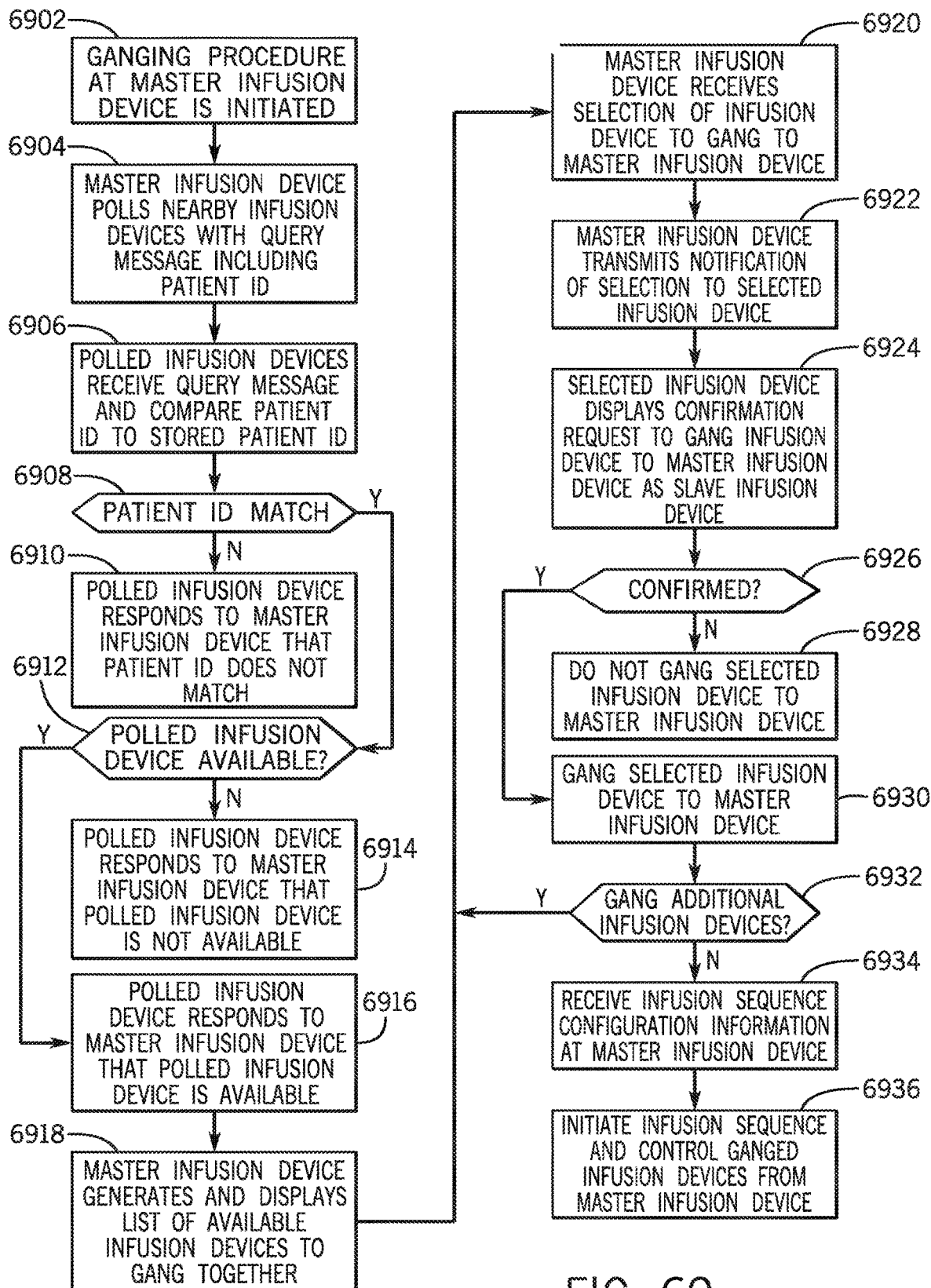
FIG. 69 depicts a flowchart of example method steps for ganging together infusion devices via direct communications.

FIG. 69 depicts a flowchart of example method steps for ganging together infusion devices via direct communications. A caregiver initiates the ganging procedure at an infusion device configured to exchange direct communications (e.g., wired or wireless) with other infusion devices. (block 6902). The infusion device at which the ganging process is initiated may likewise be designated as the master infusion device. The master infusion device polls nearby infusion devices with a query message that may include a unique identifier (ID) for the patient associated with the master infusion device (block 6904). The patient ID may indicate the patient an infusion device is associated with, and in infusion device may store the patient ID. Nearby infusion devices may include infusion devices mounted at the same interconnecting device as the master infusion device as well as infusion devices within a broadcast range of the master infusion device. Accordingly the master infusion device may poll nearby infusion devices with a query message transmitted via a wired or wireless communication.

A polled infusion device may receive the query message from the master infusion device and compare the patient ID included in the query message with its stored patient ID (block 6906). If the patient IDs do not match (block 6908: N), then the polled infusion device may transmit a response to the master infusion device indicating that the patient IDs do not match (block 6910) and that the polled infusion device is thus unavailable to be ganged to the master infusion device. If, however, the patient IDs do match (block 6908: Y), then the polled infusion device may assess whether it is available to be ganged to the master infusion device. If the polled infusion device is not available to be ganged to the master infusion device (block 6912: N), then the polled infusion device may respond to the master infusion device that it is currently unavailable. Alternatively the polled infusion device may simply not respond to the master infusion device if it is currently unavailable. If, however, the polled infusion device is available (block 6912: Y), then the polled infusion device may respond to the master infusion device indicating that it is available to be ganged to the master infusion device (block 6916). The polled infusion device may also respond to the master infusion device indicating that is available to be ganged to the master infusion device if the polled infusion device is not currently associated with a patient.

Multiple infusion devices may respond to the master infusion device indicating they are available to be ganged to the master infusion device. Once the master infusion device has received response from the polled infusion devices, the master infusion device generates and displays a list of infusion devices that are available to be ganged together (block 6918). The master infusion device then receives from the caregiver a selection of one of the infusion devices to gang to the master infusion device (block 6920). The master infusion device then transmits a notification of the selection to the selected infusion device (block 6922).

In response to receipt of the notification, the selected infusion device displays (e.g., at a display screen) a confirmation request for the caregiver to confirm the selected infusion device should be ganged to the master infusion device as a slave infusion device (block 6924). If the caregiver does not confirm that the selected infusion device should be ganged to the master infusion device (block 6926: N), then the selected infusion device is not ganged to the master infusion device (block 6928). If, however, the caregiver does confirm that the selected infusion device should be ganged to the master infusion device (block 6926: Y), then the selected infusion device is ganged to the master infusion device (block 6930). The caregiver may gang multiple infusion devices to the master infusion devices. Accordingly, if the caregiver wishes to gang additional infusion devices to the master infusion device (block 6932: Y), the caregiver may repeat the steps above to gang additional infusion devices to the master infusion device. If the caregiver does not wish to gang additional infusion devices to the master infusion device (block 6932: N), or once the caregiver has ganged the desired number of infusion devices to the master infusion device, the caregiver may provide the infusion sequence configuration information to the master infusion device (block 6934). Once the caregiver has configured and confirmed the inter-device infusion sequence, the caregiver may initiate the infusion sequence and the master infusion device controls the infusion sequence across the ganged infusion devices (block 6936).

Figure 70:
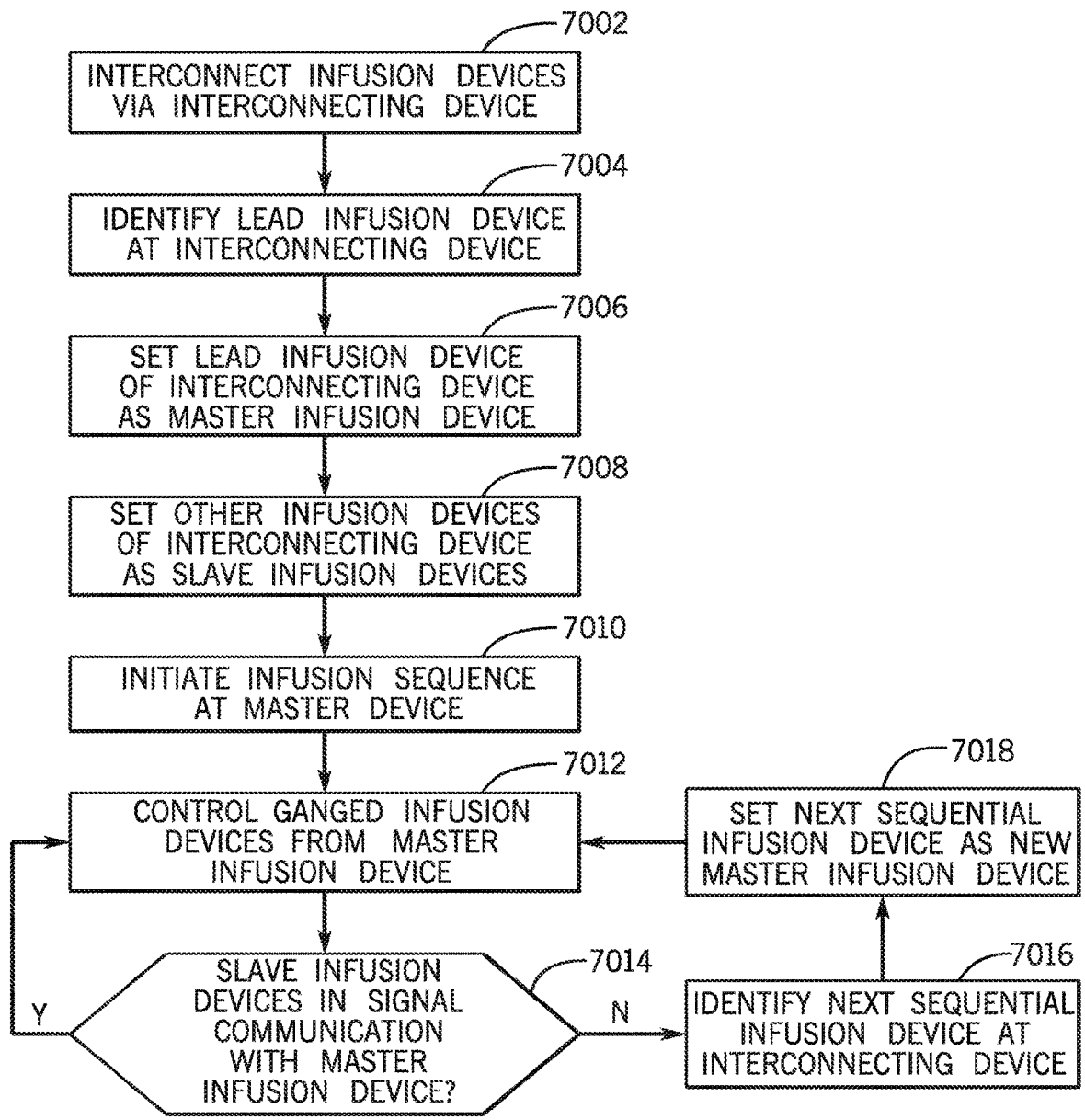
FIG. 70 depicts a flowchart of example method steps for designating a master infusion device for infusion devices ganged together via an interconnecting device.

FIG. 70 depicts a flowchart of example method steps for designating a master infusion device for infusion devices ganged together via an interconnecting device. A set of infusion devices may be interconnected via an interconnecting device (block 7002). The lead infusion device at the interconnecting device may be identified (block 7004), e.g., the top-most or left-most infusion device mounted at the interconnecting device. The lead infusion device may be set as the master infusion device (block 7006) and one or more of the other infusion devices mounted at the interconnecting device may be designated as slave infusion devices to gang those infusion devices with the master infusion device (block 7008). The master infusion device may initiate an infusion sequence involving the ganged infusion devices (block 7010) and control the ganged infusion devices during the infusion sequence (block 7012).

While the slave infusion devices remain in signal communication with the master infusion device (block 7014: Y), the master infusion device may continue to control the ganged infusion devices during the infusion sequence (block 7012). If, however, the slave infusion devices lose the connection to the master infusion device and are no longer in signal communication with the master infusion device (block 7014: N), then the next sequential infusion device at the interconnecting device (e.g., the next top-most) may be identified (block 7016) and designated as the new master infusion device (block 7018). The new master infusion device may take over controlling the ganged infusion devices during the infusion sequence (block 7012).

Figure 71:
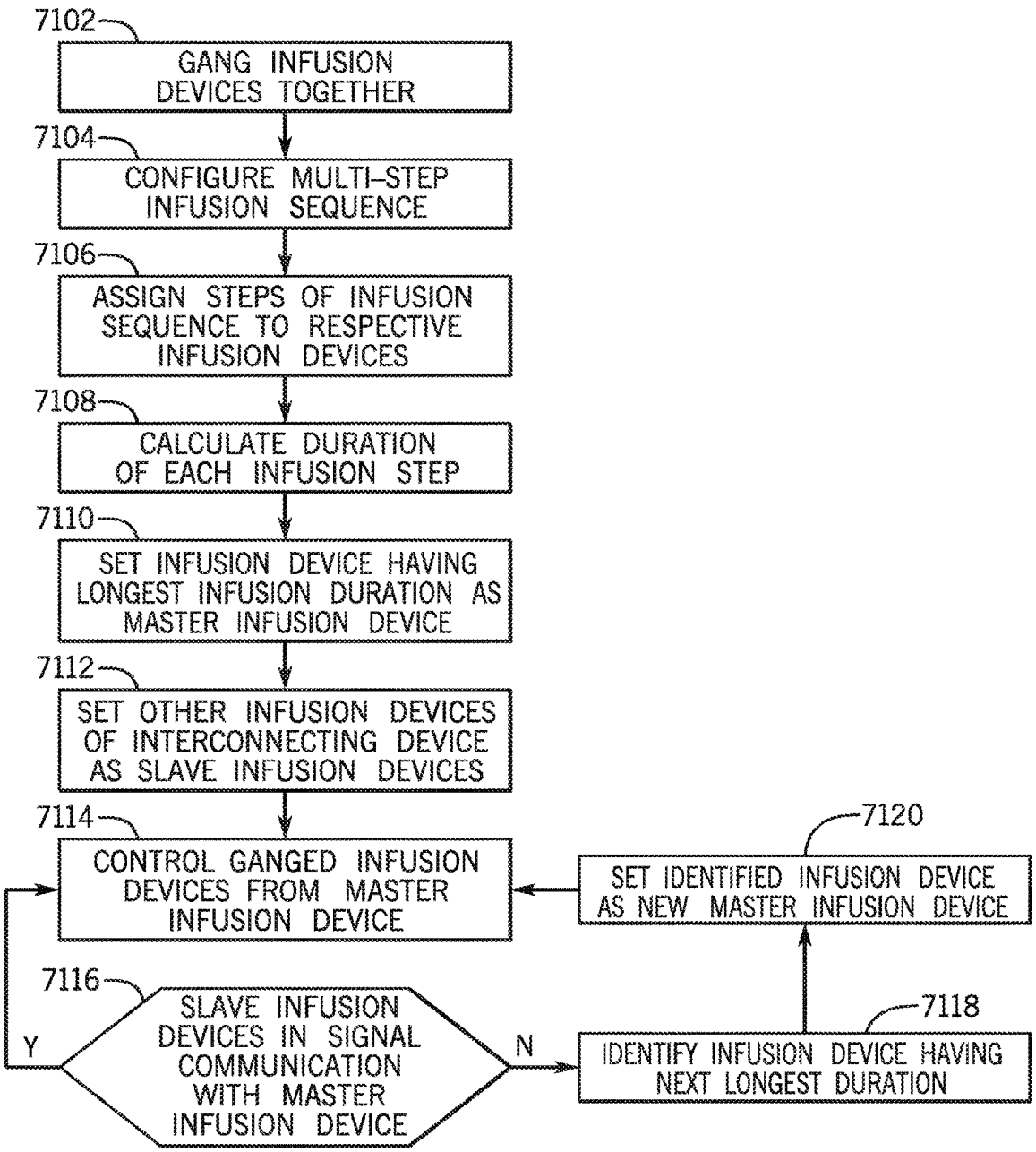
FIG. 71 depicts a flowchart of example method steps for designating a master infusion device for infusion devices ganged together via wireless communications.

FIG. 71 depicts a flowchart of example method steps for designating a master infusion device for infusion devices ganged together via wireless communications. A set of infusion devices in wireless signal communication with each other may be ganged together (block 7102), and a caregiver may configure a multi-step infusion sequence for the ganged infusion devices (block 7104). The caregiver may assign various steps of the multi-step infusion sequence to various infusion devices that have been ganged together (block 7106). The duration of each step may be calculate (block 7108), and the infusion device having the longest infusion duration may be designated as the master infusion device (block 7110). The other infusion devices may be designated as slave infusion devices for the master infusion device (block 7112).

During the infusion sequence, the master infusion device may control the slave infusion devices (block 7114). While the slave infusion devices remain in signal communication with the master infusion device (block 7116: Y), the master infusion device may continue to control the ganged infusion devices during the multi-step infusion sequence. If, however, the slave infusion devices lose the connection to the master infusion device and are no longer in signal communication with the master infusion device (block 7116: N), then the infusion device having the next longest infusion duration is identified (block 7118) and designated as the new master infusion device (block 7120). The new master infusion device may take over controlling the ganged infusion devices during the infusion sequence (block 7114).

It will be appreciated with the benefit of this disclosure that various combinations of the steps described above may be employed where the ganged together infusion devices include infusion devices that are in signal communication both wirelessly and via an interconnecting device. As an example, the ganged together infusion devices include infusion devices mounted at an interconnecting device as well as infusion devices that exchange communications wirelessly. In this example, the infusion devices at the interconnecting device may take precedence over the infusion devices ganged together wirelessly such that the lead infusion device at the interconnecting device may be designated the master infusion device. If the connection to the master infusion device is lost, the new master infusion device may be designated from the next sequential infusion device at the interconnecting device until connection with all infusion devices at the interconnecting device has been lost at which point, the new master infusion device may be the wirelessly communicating infusion device having the longest duration. If the set of ganged together infusion devices includes multiple interconnecting devices and connection to all infusion devices at one of the interconnecting devices has been lost, then the lead infusion device at the next sequential interconnecting device may be designated as the new master infusion device and so forth.

Figure 72A:
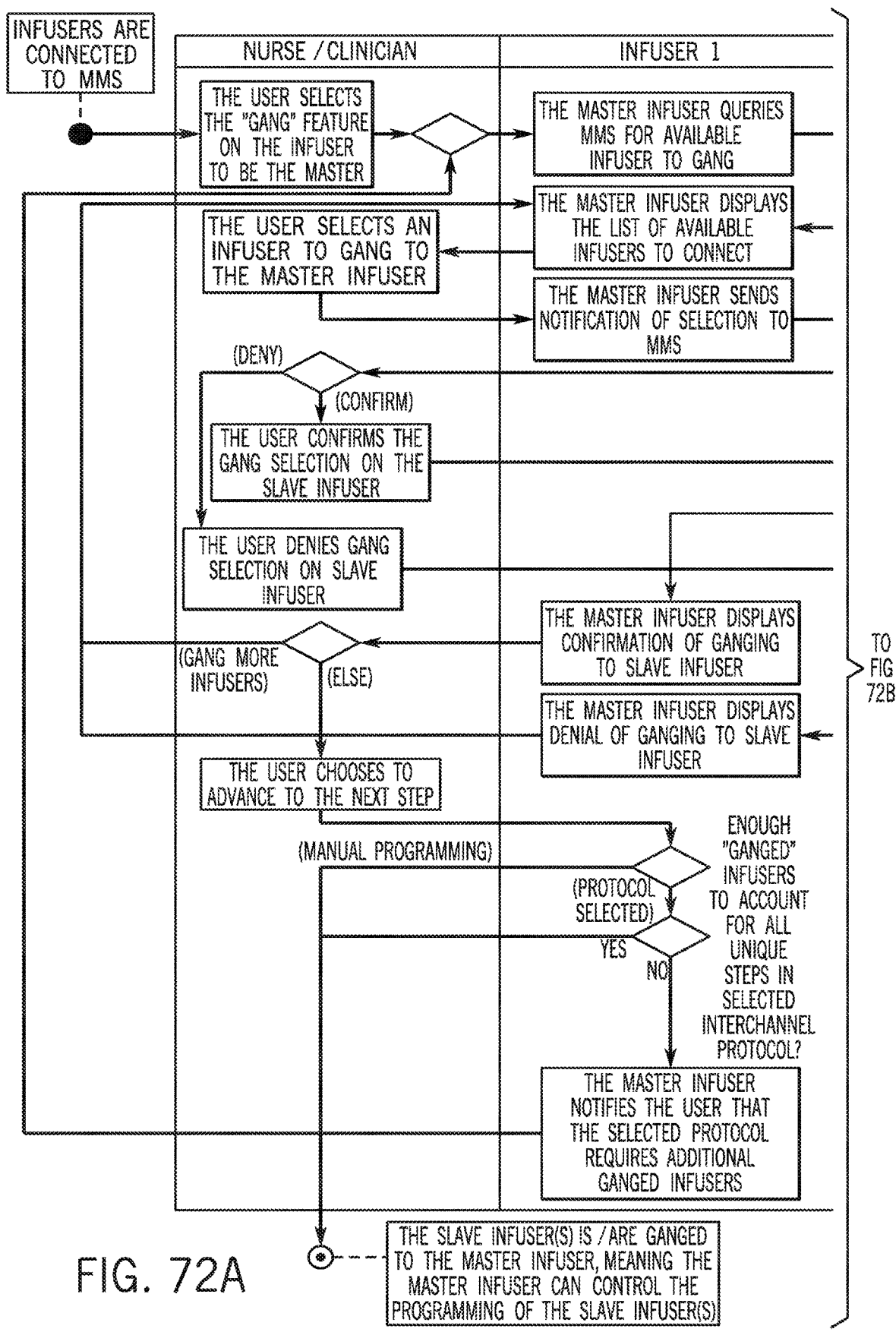
FIGS. 72A-72B depict example steps of another method for ganging together infusion devices that are interconnected via a medication management system.
Figure 72B:
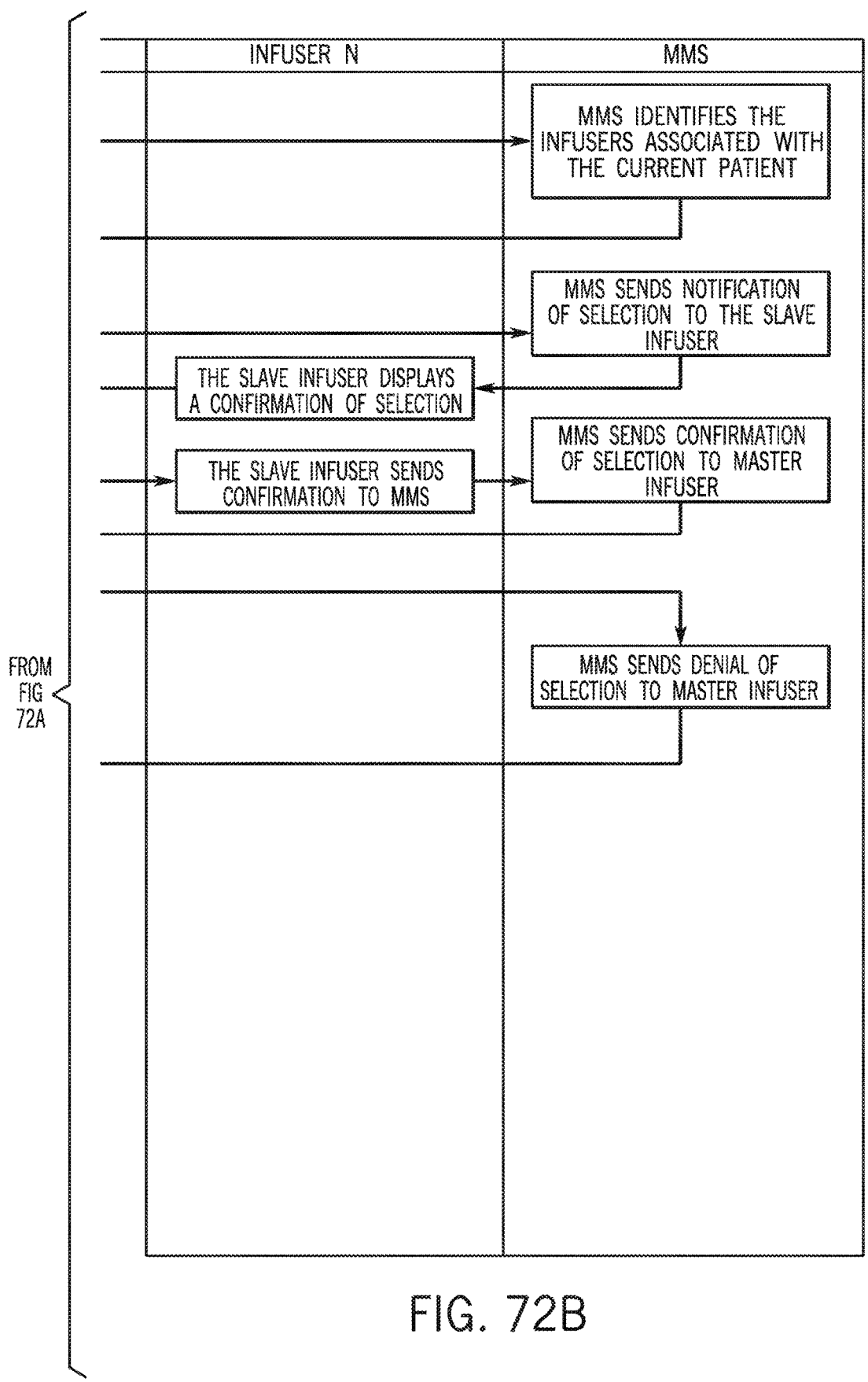

FIGS. 72A-72B depict another flowchart of example method steps for ganging together infusion devices that are interconnected via a medication management system.

Interconnecting infusion devices wirelessly, via an interconnecting device, or via a medication management system provides various advantages when performing infusions at a patient. Some example advantages include limiting the total infusion rate across each infusion device associated with a patient, tracking accumulated air across the infusion devices associated with a patient, choosing a connecting site for an infusion device and checking drug compatibility across the same connection site, and checking for duplicate drug selections across each infusion device associated with a patient. With respect to limiting the infusion rate, inter-device communication allows a caregiver or care facility (e.g., a hospital) to limit the total infusion rate across each infusion device associated with the patient to an infusion rate determined by the caregiver or care facility. The total infusion rate may be limited across each channel on a dual-channel infusion device or across each respective channel of multiple infusion devices. Potentially unsafe infusion rates may thus be identified and tracked. With respect to tracking accumulated air, the inter-device communication allows a caregiver or care facility to track the air that has been accumulated across all infusion device types associated with a patient, e.g., LVP, syringe, and PCA infusion device types. The interconnected infusion devices may provide an alarm when the accumulated air reaches an air accumulation threshold which may be set by the caregiver or care facility. A caregiver may also select a connection site for the infusion devices and initiate a drug compatibility check. As described above, a caregiver may be notified of any potential drug incompatibilities at a common connection site which the caregiver may override if needed. A caregiver may likewise initiate a duplicate drug selection check across infusion devices associated with a patient and receive notification of any duplicate drugs selected to be infused at the patient and again override if needed.

The drug duplication and compatibility checks may happen in the background as the caregiver continues programming the infusion sequence thus preventing delays in therapy in the case where there is no duplicate. When connected via an MMS, the duplicate drug check may be accomplished in various ways, e.g., 1) if the drug is being programmed for an inter-channel sequence then the infusion device checks the selected drug against the other selected drugs for all other steps in the therapy; 2) the infusion device sends a status message with the selected medication to the MMS which checks if the selected drug is programmed on other channels for the patient, and the MMS will respond with the results of the duplication check; 3) the infusion device sends the selected drug to the other infusers connected via an interconnecting device and the other infusion devices will respond with the results of the duplication check; 4) the infusion device polls nearby infusers wirelessly to check if they are associated to the same patient and, if so, the infusion device sends the selected drug to the other infusion devices associated with the patient. The other infusion devices may then respond with the results of the duplication check.

Similar techniques may be utilized to check for drug compatibility. An infusion device may likewise check for potential drug incompatibility in various ways, e.g., 1) the infusion device may send its currently programmed clinical care area (CCA) to the other infusion devices. If the other infusion devices are in the same CCA, the infusion device may send the programmed drug to the other infusion devices which may issue a response indicating that no compatibility issues exist or respond with the incompatible drug name; 2) the infusion device sends its currently programmed CCA to the other infusion devices, and if the other infusion devices are not in the same CCA, the infusion device sends a list of incompatible drugs for the programmed drug to the other infusion devices which issue a response indicating no compatibility issues exist or respond with the incompatible drug name; 3) the infusion device requests the drugs with which the other infusion devices are programmed and the first infusion device checks for compatibility against its drug library.

With respect to tracking accumulated air across each infusion device associated with a patient, if an MMS is present, the MMS may be configured to receive periodic status messages that include accumulated air values from infusion devices during an ongoing infusion. The MMS may aggregate the accumulated air values from the infusion devices associated with the patient and send the aggregated value to each infusion device in a response to the periodic status message or as a separate message. If one of the infusion devices associated with the patient detects accumulated air that exceeds the threshold for accumulated air, that infusion device will provide a notification or alarm. The infusion device may continue infusing based on criticality of the substance being infused or other drug library rules. The other associated infusion devices may continue infusing until they also detect accumulated air, at which point they will also provide a notification or alarm. The caregiver may then attend to the alarming infusion devices, which may include dismissing the alarm message, resetting the accumulated air value, or removing air from the infusion device. Once the caregiver resets the accumulated air value, the MMS may be notified via the status message and may disseminate the reset value to the associated infusion devices. If the MMS connection is lost, then the infusion devices may continue operating on the most recently received aggregate accumulated air value, adding to the value as it tracks air, if any. Each infusion device may provide a notification or alarm individually if it exceeds the accumulated air threshold. When the MMS connection is reestablished, the infusion devices may send their current accumulated air values to the MMS which may sum the accumulated air across all infusion devices from the previous aggregate value and disseminate that value to the associated infusion devices. The infusion devices may also be configured to connect locally to the other associated infusion devices to continue tracking the aggregate accumulated air. This may occur whether the MMS was originally present or not. If connected via an interconnecting device, the top-most infusion device may designated as the master infusion device as described above and may be responsible for computing the aggregate accumulated air value. If the infusion devices utilize point-to-point wireless communication, the infusion device having the longest infusion duration remaining may be designated the master infusion device and likewise be responsible for computing the accumulated air value. If the infusion devices were communicating locally and a connection to an MMS is established, the master infusion device may send its aggregated value to the MMS and the infusion devices which lost connection to the master infusion device, if any, may also send their accumulated air values. The MMS may then disseminate the new aggregate accumulated air value.

Limiting the total infusion rate across each infusion device associated with a patient may function in a fashion similar to that of tracking the accumulated air. The total infusion rate may be set by the caregiver, the care facility, or the CCA. If an MMS is present, the MMS may track the total infusion rate. If, however, an MMS is not present, then the infusion devices may communicate with one another to designate a master infusion device, and the master infusion device may track the total infusion rate.

Figure 73:
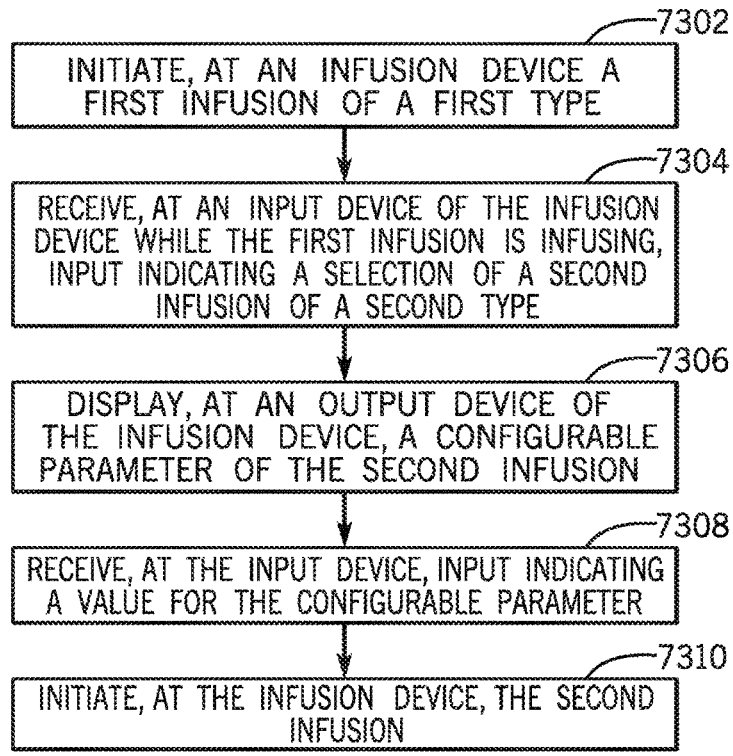
FIG. 73 depicts a flowchart of example method steps for configuring an infusion at an infusion device.

FIG. 73 depicts a flowchart of example method steps for configuring an infusion at an infusion device. A first infusion of a first type may be initiated at an infusion device (block 7302). While the first infusion is infusing, the infusion device may receive, at an input device, input indicating a selection of a second infusion of a second type (block 7304). The infusion device may display, at an output device, a configurable parameter of the second infusion (block 7306). The infusion device may then receive, at the input device, input indicating a value for the configurable parameter (block 7308). The infusion device may then initiate the second infusion.

Figure 74:
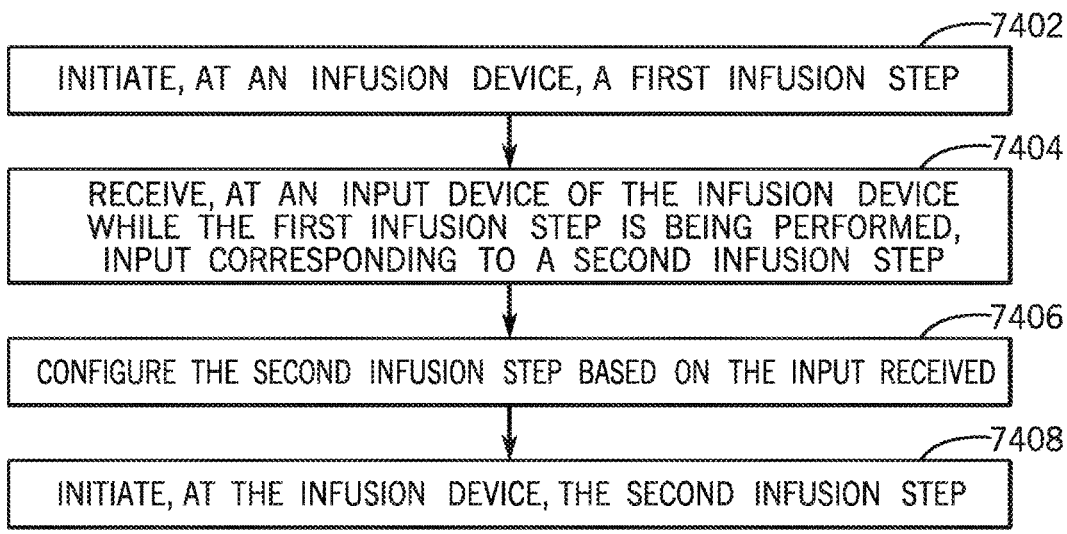
FIG. 74 depicts a flowchart of example method steps for configuring a sequence of infusion steps at an infusion device.

FIG. 74 depicts a flowchart of example method steps for configuring a sequence of infusion steps at an infusion device. An infusion device may initiate a first infusion step of an infusion (block 7402). While the first infusion step is being performed, the infusion device may receive, at an input device, input corresponding to a second infusion step (block 7404). The second infusion step may be configured based on the input received (block 7406), and the infusion device may initiate the second infusion step (block 7408).

Figure 75:
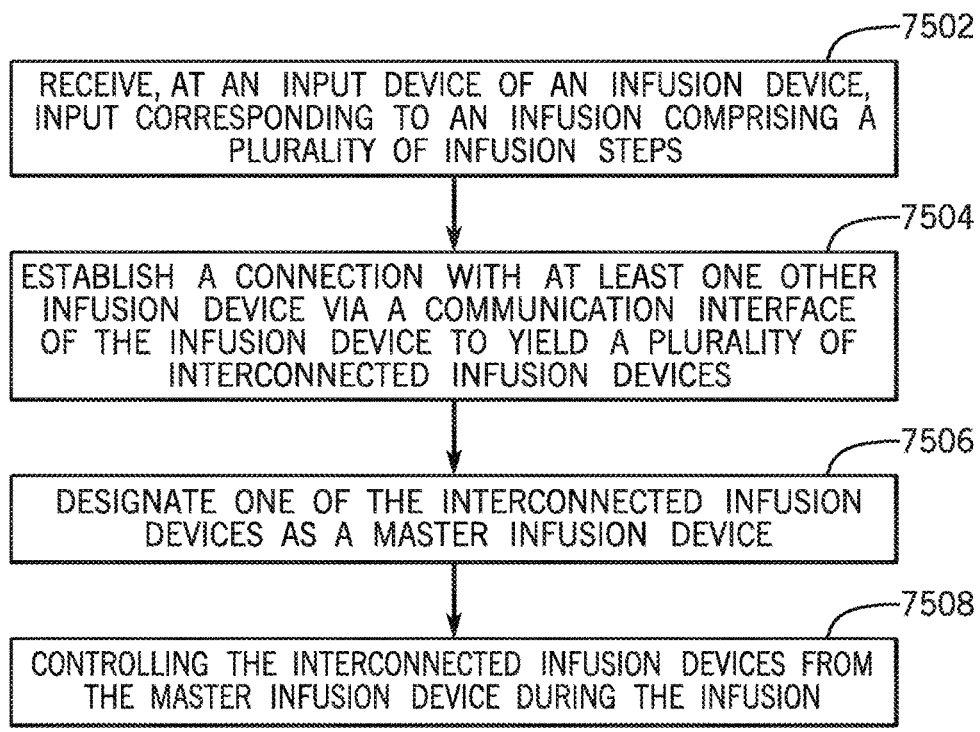
FIG. 75 depicts a flowchart of example method steps for interconnecting multiple infusion devices and controlling the interconnected infusion devices from a master infusion device during an infusion.

FIG. 75 depicts a flowchart of example method steps for interconnecting multiple infusion devices and controlling the interconnected infusion devices from a master infusion device during an infusion. An infusion device may receive, via an input device, input corresponding to an infusion comprising a plurality of infusion steps (block 7502). The infusion device may establish a connection with at least one other infusion device via a communication interface to yield a plurality of interconnected infusion devices (block 7504). One of the interconnected infusion devices may be designated as a master infusion device (block 7506). During the infusion, the interconnected infusion devices may be controlled from the infusion device designated as the master infusion device (block 7508).

While the disclosure has been described with respect to specific examples including presently illustrative modes of carrying out the disclosure, a person having ordinary skill in the art, after review of the entirety disclosed herein, will appreciate that there are numerous variations and permutations of the above-described systems and techniques that fall within the spirit and scope of the disclosure.

What is claimed is:

1. A method of performing an infusion comprising:
receiving, at an input device of one of a plurality of infusion devices, input corresponding to an infusion comprising a plurality of infusion steps;
establishing a wireless connection between at least two of the plurality of infusion devices to yield a plurality of interconnected infusion devices;
designating one of the plurality of interconnected infusion devices as a master infusion device;
controlling the plurality of interconnected infusion devices from the master infusion device during the infusion;
determining, during the infusion, that the wireless connection to the master infusion device has been lost;
designating another one of the plurality of interconnected infusion devices as a new master infusion device; and
controlling the plurality of interconnected infusion devices from the new master infusion device during the infusion.

2. The method of claim 1, wherein:
a first one of the plurality of interconnected infusion devices is configured to perform a first infusion step of the infusion; and
a second one of the plurality of interconnected infusion devices is configured to perform a second infusion step of the infusion.

3. The method of claim 1, wherein:
the interconnected infusion device designated as the master infusion device is the interconnected infusion device configured to perform an infusion step of the infusion that has a longest infusion duration.

4. The method of claim 3, wherein:
the interconnected infusion device designated as the new master infusion device is the interconnected infusion device configured to perform a remaining infusion step of the infusion that has the longest duration of one or more remaining infusion steps of the infusion.

5. The method of claim 3, wherein:
the plurality of interconnected infusion devices are interconnected in series at an interconnecting device; and
the interconnected infusion device designated as the master infusion device is the interconnected infusion device that is next in the series at the interconnecting device.

6. The method of claim 1, wherein:
the plurality of interconnected infusion devices are connected in series via an interconnecting device; and
the interconnected infusion device designated as the master infusion device is the interconnected infusion device that is first in the series at the interconnecting device.

7. The method of claim 6, wherein:
the interconnecting device is one of a backplane, a rack, or a dock.

8. The method of claim 1, further comprising:
polling one of the plurality of infusion devices from another one of the plurality of infusion devices; and
determining whether the other infusion device is available to perform at least one of the plurality of infusion steps based on the poll.

9. The method of claim 8, wherein:
the polling comprises transmitting a message to the other infusion device that identifies a patient.

10. The method of claim 1, further comprising:
performing, before initiating the infusion, a safety check based on one or more substances the plurality of interconnected infusion devices are configured to infuse during the infusion.

11. The method of claim 10, wherein:
the safety check comprises at least one of a duplicability check and a compatibility check.

12. The method of claim 1, further comprising:
tracking a total amount of air that the plurality of interconnected infusion devices accumulate during the infusion; and providing a notification responsive to determining that the total amount of air that has been accumulated exceeds an accumulated air threshold.

\* \* \* \* \*